US006790640B2

(12) United States Patent
Craft et al.

(10) Patent No.: US 6,790,640 B2
(45) Date of Patent: Sep. 14, 2004

(54) METHOD OF INCREASING CONVERSION OF A FATTY ACID TO ITS CORRESPONDING DICARBOXYLIC ACID

(75) Inventors: David L. Craft, Ft. Thomas, KY (US); C. Ron Wilson, Loveland, OH (US); Dudley Eirich, Milford, OH (US); Yeyan Zhang, Mason, OH (US)

(73) Assignee: Cognis Corporation, Ambler, PA (US)

( * ) Notice: Subject to any disclaimer, the term of this patent is extended or adjusted under 35 U.S.C. 154(b) by 0 days.

(21) Appl. No.: 10/400,902

(22) Filed: Mar. 31, 2003

(65) Prior Publication Data

US 2003/0175896 A1 Sep. 18, 2003

Related U.S. Application Data

(62) Division of application No. 09/911,781, filed on Jul. 24, 2001, now Pat. No. 6,673,613.

(60) Provisional application No. 60/220,850, filed on Jul. 26, 2000.

(51) Int. Cl.[7] .................................................. C12P 21/02

(52) U.S. Cl. ...................................................... 435/69.1

(58) Field of Search ......................................... 435/69.1

(56) References Cited

U.S. PATENT DOCUMENTS 6,331,420 B1 * 12/2001 Wilson et al.

FOREIGN PATENT DOCUMENTS

WO WO-00/20566 * 4/2000

OTHER PUBLICATIONS

Seghezzi et al, Gene, 1991, vol. 106, pp. 51–60.*

* cited by examiner

*Primary Examiner*—Terry McKelvey
(74) *Attorney, Agent, or Firm*—Aaron R. Ettelman

(57) ABSTRACT

A nucleic acid sequence including a CYP promoter operably linked to nucleic acid encoding a heterologous protein is provided to increase transcription of the nucleic acid. Expression vectors and host cells containing the nucleic acid sequence are also provided. The methods and compositions described herein are especially useful in the production of polycarboxylic acids by yeast cells.

7 Claims, 19 Drawing Sheets

```
gacctgtgac gcttccggtg tcttgccacc agtctccaag ttgaccgacg cccaagtcat 60
gtaccacttt atttccggtt acacttccaa gatggctggt actgaagaag gtgtcacgga 120
accacaagct actttctccg cttgtttcgg tcaaccattc ttggtgttgc acccaatgaa 180
gtacgctcaa caattgtctg acaagatctc gcaacacaag gctaacgcct ggttgttgaa 240
caccggttgg gttggttctt ctgctgctag aggtggtaag agatgctcat tgaagtacac 300
cagagccatt ttggacgcta tccactctgg tgaattgtcc aaggttgaat acgaaacttt 360
cccagtcttc aacttgaatg tcccaacctc ctgtccaggt gtcccaagtg aaatcttgaa 420
cccaaccaag gcctggaccg gaaggtgttg actccttcaa caaggaaatc aagtctttgg 480
ctggtaagtt tgctgaaaac ttcaagacct atgctgacca agctaccgct gaagtgagag 540
ctgcaggtcc agaagcttaa agatatttat tcattattta gtttgcctat ttatttctca 600
ttacccatca tcattcaaca ctatatataa agttacttcg gatatcattg taatcgtgcg 660
tgtcgcaatt ggatgatttg gaactgcgct tgaaacggat tcatgcacga agcggagata 720
aaagattacg taatttatct cctgagacaa ttttagccgt gttcacacgc ccttctttgt 780
tctgagcgaa ggataaataa ttagacttcc acagctcatt ctaatttccg tcacgcgaat 840
attgaagggg ggtacatgtg gccgctgaat gtgggggcag taaacgcagt ctctcctctc 900
ccaggaatag tgcaacggag gaaggataac ggatagaaag cggaatgcga ggaaaatttt 960
gaacgcgcaa gaaaagcaat atccgggcta ccaggttttg agccagggaa cacactccta 1020
tttctgctca atgactgaac atagaaaaaa caccaagacg caatgaaacg cacatggaca 1080
tttagacctc cccacatgtg atagtttgtc ttaacagaaa agtataataa gaacccatgc 1140
cgtccctttt ctttcgccgc ttcaactttt ttttttttat cttacacaca tcacgaccat 1200
gactgtacac gatattatcg ccacatactt caccaaatgg tacgtgatag taccactcgc 1260
tttgattgct tatagagtcc tcgactactt ctatggcaga tacttgatgt acaagcttgg 1320
tgctaaacca tttttccaga aacagacaga cggctgtttc ggattcaaag ctccgcttga 1380
attgttgaag aagaagagcg acggtaccct catagacttc acactccagc gtatccacga 1440
tctcgatcgt cccgatatcc caactttcac attcccggtc ttttccatca accttgtcaa 1500
taccttgag ccggagaaca tcaaggccat cttggccact cagttcaacg atttctcctt 1560
gggtaccaga cactcgcact ttgctccttt gttgggtgat ggtatcttta cgttggatgg 1620
cgccggctgg aagcacagca gatctatgtt gagaccacag tttgccagag aacagatttc 1680
ccacgtcaag ttgttggagc cacacgttca ggtgttcttc aaacacgtca gaaaggcaca 1740
gggcaagact tttgacatcc aggaattgtt tttcagattg accgtcgact ccgccaccga 1800
gtttttgttt ggtgaatccg ttgagtcctt gagagatgaa tctatcggca tgtccatcaa 1860
tgcgcttgac tttgacggca aggctggctt tgctgatgct tttaactatt cgcagaatta 1920
tttggcttcg agagcggtta tgcaacaatt gtactgggtg ttgaacggga aaaagtttaa 1980
ggagtgcaac gctaaagtgc acaagtttgc tgactactac gtcaacaagg ctttggactt 2040
gacgcctgaa caattggaaa agcaggatgg ttatgtgttt ttgtacgaat tggtcaagca 2100
aaccagagac aagcaagtgt tgagagacca attgttgaac atcatggttg ctggtagaga 2160
caccaccgcc ggtttgttgt cgtttgtttt ctttgaattg gccagaaacc cagaagttac 2220
caacaagttg agagaagaaa ttgaggacaa gtttggactc ggtgagaatg ctagtgttga 2280
agacatttcc tttgagtcgt tgaagtcctg tgaatacttg aaggctgttc tcaacgaaac 2340
cttgagattg tacccatccg tgccacagaa tttcagagtt gccaccaaga acactaccct 2400
cccaagaggt ggtggtaagg acgggttgtc tcctgttttg gtgagaaagg gtcagaccgt 2460
tatttacggt gtctacgcag cccacagaaa cccagctgtt tacggtaagg acgctcttga 2520
gtttagacca gagagatggt ttgagccaga gacaaagaag cttggctggg ccttcctccc 2580
attcaacggt ggtccaagaa tctgtttggg acagcagttt gccttgacag aagcttcgta 2640
tgtcactgtc aggttgctcc aggagtttgc acacttgtct atggacccag acaccgaata 2700
tccacctaag aaaatgtcgc atttgaccat gtcgcttttc gacggtgcca atattgagat 2760
gtattagagg gtcatgtgtt attttgattg tttagtttgt aattactgat taggttaatt 2820
catggattgt tatttattga taggggtttg cgcgtgttgc attcacttgg gatcgttcca 2880
ggttgatgtt tccttccatc ctgtcgagtc aaaaggagtt ttgttttgta actccggacg 2940
```

FIG. 1A

```
atgttttaaa tagaaggtcg atctccatgt gattgttttg actgttactg tgattatgta 3000
atctgcggac gttatacaag catgtgattg tggttttgca gccttttgca cgacaaatga 3060
tcgtcagacg attacgtaat ctttgttaga ggggtaaaaa aaaacaaaat ggcagccaga 3120
atttcaaaca ttctgcaaac aatgcaaaaa atgggaaact ccaacagaca aaaaaaaaaa 3180
ctccgcagca ctccgaaccc acagaacaat ggggcgccag aattattgac tattgtgact 3240
tttttacgct aacgctcatt gcagtgtagt gcgtcttaca cggggtattg ctttctacaa 3300
tgcaagggca cagttgaagg tttgcaccta acgttgcccc gtgtcaactc aatttgacga 3360
gtaacttcct aagctcgaat tatgcagctc gtgcgtcaac ctatgtgcag gaaagaaaaa 3420
atccaaaaaa atcgaaaatg cgactttcga ttttgaataa accaaaaaga aaaatgtcgc 3480
acttttttct cgctctcgct ctctcgaccc aaatcacaac aaatcctcgc gcgcagtatt 3540
tcgacgaaac cacaacaaat aaaaaaaaca aattctacac cacttctttt tcttcaccag 3600
tcaacaaaaa acaacaaatt atacaccatt tcaacgattt ttgctcttat aaatgctata 3660
taatggttta attcaactca ggtatgttta ttttactgtt ttcagctcaa gtatgttcaa 3720
atactaacta cttttgatgt ttgtcgcttt tctagaatca aaacaacgcc cacaacacgc 3780
cgagcttgtc gaatagacgg tttgtttact cattagatgg tcccagatta cttttcaagc 3840
caaagtctct cgagttttgt ttgctgtttc cccaattcct aactatgaag ggtttttata 3900
aggtccaaag accccaaggc atagtttttt tggttccttc ttgtcgtg             3948
```

FIG. 1B

```
catcaagatc atctatgggg ataattacga cagcaacatt gcagaaagag cgttggtcac 60
aatcgaaaga gcctatggcg ttgccgtcgt tgaggcaaat gacagcacca acaataacga 120
tggtcccagt gaagagcctt cagaacagtc cattgttgac gcttaaggca cggataatta 180
cgtggggcaa aggaacgcgg aattagttat ggggggatca aaagcggaag atttgtgttg 240
cttgtgggtt ttttccttta tttttcatat gatttctttg cgcaagtaac atgtgccaat 300
ttagtttgtg attagcgtgc cccacaattg gcatcgtgga cgggcgtgtt ttgtcatacc 360
ccaagtctta actagctcca cagtctcgac ggtgtctcga cgatgtcttc ttccacccct 420
cccatgaatc attcaaagtt gttgggggat ctccaccaag ggcaccggag ttaatgctta 480
tgtttctccc actttggttg tgattggggt agtctagtga gttggagatt ttcttttttt 540
cgcaggtgtc tccgatatcg aaatttgatg aatatagaga gaagccagat cagcacagta 600
gattgccttt gtagttagag atgttgaaca gcaactagtt gaattacacg ccaccacttg 660
acagcaagtg cagtgagctg taaacgatgc agccagagtg tcaccaccaa ctgacgttgg 720
gtggagttgt tgttgttgtt gttggcaggg ccatattgct aaacgaagac aagtagcaca 780
aaacccaagc ttaagaacaa aaataaaaaa aattcatacg acaattccaa agccattgat 840
ttacataatc aacagtaaga cagaaaaaac tttcaacatt tcaaagttcc ctttttccta 900
ttacttcttt tttttcttct ttccttcttt ccttctgttt ttcttacttt atcagtcttt 960
tacttgtttt tgcaattcct catcctcctc ctactcctcc tcaccatggc tttagacaag 1020
ttagatttgt atgtcatcat aacattggtg gtcgctgtag ccgcctattt tgctaagaac 1080
cagttccttg atcagcccca ggacaccggg ttcctcaaca cggacagcgg aagcaactcc 1140
agagacgtct tgctgacatt gaagaagaat aataaaaaca cgttgttgtt gtttgggtcc 1200
cagacgggta cggcagaaga ttacgccaac aaattgtcca gagaattgca ctccagattt 1260
ggcttgaaaa cgatggttgc agatttcgct gattacgatt gggataactt cggagatatc 1320
accgaagaca tcttggtgtt tttcattgtt gccacctatg gtgagggtga acctaccgat 1380
aatgccgacg agttccacac ctggttgact gaagaagctg acactttgag taccttgaaa 1440
tacaccgtgt tcgggttggg taactccacg tacgagttct tcaatgccat tggtagaaag 1500
tttgacagat tgttgagcga gaaaggtggt gacaggtttg ctgaatacgc tgaaggtgat 1560
gacggtactg gcaccttgga cgaagatttc atggcctgga aggacaatgt ctttgacgcc 1620
ttgaagaatg atttgaactt tgaagaaaag gaattgaagt acgaaccaaa cgtgaaattg 1680
actgagagag acgacttgtc tgctgctgac tcccaagttt ccttgggtga gccaaacaag 1740
aagtacatca actccgaggg catcgacttg accaagggtc cattcgacca cacccaccca 1800
tacttggcca gaatcaccga gacgagagag ttgttcagct ccaaggacag acactgtatc 1860
cacgttgaat ttgacatttc tgaatcgaac ttgaaataca ccaccggtga ccatctagct 1920
atctggccat ccaactccga cgaaaacatt aagcaatttg ccaagtgttt cggattggaa 1980
gataaactcg acactgttat tgaattgaag gcgttggact ccacttacac catcccattc 2040
ccaaccccaa ttacctacgg tgctgtcatt agacaccatt tagaaatctc cggtccagtc 2100
tcgagacaat tctttttgtc aattgctggg tttgctcctg atgaagaaac aaagaaggct 2160
tttaccagac ttggtggtga caagcaagaa ttcgccgcca aggtcacccg cagaaagttc 2220
aacattgccg atgccttgtt atattcctcc aacaacgctc catggtccga tgttcctttt 2280
gaattcctta ttgaaaacgt tccacacttg actccacgtt actactccat ttcgtcttcg 2340
tcattgagtg aaaagcaact catcaacgtt actgcagttg ttgaagccga agaagaagct 2400
gatggcagac cagtcactgg tgttgtcacc aacttgttga agaacgttga aattgtgcaa 2460
aacaagactg gcgaaaagcc acttgtccac tacgatttga gcggcccaag aggcaagttc 2520
aacaagttca agttgccagt gcatgtgaga agatccaact ttaagttgcc aaagaactcc 2580
accaccccag ttatcttgat tggtccaggt actggtgttg ccccattgag aggttttgtc 2640
agagaaagag ttcaacaagt caagaatggt gtcaatgttg gcaagacttt gttgttttat 2700
ggttgcagaa actccaacga ggactttttg tacaagcaag aatgggccga gtacgcttct 2760
gttttgggtg aaaactttga gatgttcaat gccttctcca gacaagaccc atccaagaag 2820
gtttacgtcc aggataagat tttagaaaac agccaacttg tgcacgagtt gttgactgaa 2880
ggtgccatta tctacgtctg tggtgatgcc agtagaatgg ctagagacgt gcagaccaca 2940
atttccaaga ttgttgctaa aagcagagaa attagtgaag acaaggctgc tgaattggtc 3000
aagtcctgga aggtccaaaa tagataccaa gaagatgttt ggtagactca aacgaatctc 3060
```

FIG. 2A tctttctccc aacgcattta tgaatcttta ttctcattga agctttacat atgttctaca 3120
ctttattttt tttttttttt ttattattat attacgaaac ataggtcaac tatatatact 3180
tgattaaatg ttatagaaac aataactatt atctactcgt ctacttcttt ggcattgaca 3240
tcaacattac cgttcccatt accgttgccg ttggcaatgc cgggatattt agtacagtat 3300
ctccaatccg gatttgagct attgtagatc agctgcaagt cattctccac cttcaaccag 3360
tacttatact tcatctttga cttcaagtcc aagtcataaa tattacaagt tagcaagaac 3420
ttctggccat ccacgatata gacgttattc acgttattat gcgacgtatg gatgtggtta 3480
tccttattga acttctcaaa cttcaaaaac aaccccacgt cccgcaacgt cattatcaac 3540
gacaagttct ggctcacgtc gtcggagctc gtcaagttct caattagatc gttcttgtta 3600
ttgatcttct ggtactttct caattgctgg aacacattgt cctcgttgtt caaatagatc 3660
ttgaacaact ttttcaacgg gatcaacttc tcaatctggg ccaagatctc cgcccgggatc 3720
ttcagaaaca agtcctgcaa cccctggtcg atggtctccg ggtacaacaa gtccaagggg 3780
cagaagtgtc taggcacgtg tttcaactgg ttcaacgaac atgttcgaca gtagttcgag 3840
ttatagttat cgtacaacca ttttggtttg atttcgaaaa tgacggagct gatgccatca 3900
ttctcctggt tcctctcata gtacaactgg cacttcttcg agaggctcaa ttcctcgtag 3960
ttcccgtcca agatattcgg caacaagagc ccgtaccgct cacggagcat caagtcgtgg 4020
ccctggttgt tcaacttgtt gatgaagtcc gaggtcaaga caatcaactg gatgtcgatg 4080
atctggtgcg ggaacaagtt cttgcatttt agctcgatga agtcgtacaa ctcacacgtc 4140
gagatatact cctgttcctc cttcaagagc cggatccgca agagcttgtg cttcaagtag 4200
tcgttg 4206

FIG. 2B

```
tatatgatat atgatatatc ttcctgtgta attattattc gtattcgtta atacttacta 60
catttttttt tctttattta tgaagaaaag gagagttcgt aagttgagtt gagtagaata 120
ggctgttgtg catacgggga gcagaggaga gtatccgacg aggaggaact gggtgaaatt 180
tcatctatgc tgttgcgtcc tgtactgtac tgtaaatctt agatttccta gaggttgttc 240
tagcaaataa agtgtttcaa gatacaattt tacaggcaag ggtaaaggat caactgatta 300
gcggaagatt ggtgttgcct gtggggttct tttatttttc atatgatttc tttgcgcgag 360
taacatgtgc caatctagtt tatgattagc gtacctccac aattggcatc ttggacgggc 420
gtgttttgtc ttaccccaag ccttatttag ttccacagtc tcgacggtgt ctcgccgatg 480
tcttctccca cccctcgcag gaatcattcg aagttgttgg gggatctcct ccgcagttta 540
tgttcatgtc tttcccactt tggttgtgat tggggtagcg tagtgagttg gtgatttctt 600
tttttcgcag gtgtctccga tatcgaagtt tgatgaatat aggagccaga tcagcatggt 660
atattgcctt tgtagataga gatgttgaac aacaactagc tgaattacac accaccgcta 720
aacgatgcgc acagggtgtc accgccaact gacgttgggt ggagttgttg ttggcagggc 780
catattgcta aacgaagaga agtagcacaa aacccaaggt taagaacaat taaaaaaatt 840
catacgacaa ttccacagcc atttacataa tcaacagcga caaatgagac agaaaaaact 900
ttcaacattt caaagttccc tttttcctat tacttctttt tttctttcct tcctttcatt 960
tcctttcctt ctgcttttat tactttacca gtcttttgct tgtttttgca attcctcatc 1020
ctcctcctca ccatggcttt agacaagtta gatttgtatg tcatcataac attggtggtc 1080
gctgtggccg cctatttgc taagaaccag ttccttgatc agccccagga caccgggttc 1140
ctcaacacgg acagcggaag caactccaga gacgtcttgc tgacattgaa gaagaataat 1200
aaaaacacgt tgttgttgtt tgggtcccag accggtacgg cagaagatta cgccaacaaa 1260
ttgtcaagag aattgcactc cagatttggc ttgaaaacca tggttgcaga tttcgctgat 1320
tacgattggg ataacttcgg agatatcacc gaagatatct tggtgttttt catcgttgcc 1380
acctacggtg agggtgaacc taccgacaat gccgacgagt tccacacctg gttgactgaa 1440
gaagctgaca ctttgagtac tttgagatat accgtgttcg ggttgggtaa ctccacctac 1500
gagttcttca atgctattgg tagaaagttt gacagattgt tgagtgagaa aggtggtgac 1560
agatttgctg aatatgctga aggtgacgac ggcactggca ccttggacga agatttcatg 1620
gcctggaagg ataatgtctt tgacgccttg aagaatgact tgaactttga agaaaaggaa 1680
ttgaagtacg aaccaaacgt gaaattgact gagagagatg acttgtctgc tgccgactcc 1740
caagtttcct tgggtgagcc aaacaagaag tacatcaact ccgagggcat cgacttgacc 1800
aagggtccat tcgaccacac ccacccatac ttggccagga tcaccgagac cagagagttg 1860
ttcagctcca aggaaagaca ctgtattcac gttgaatttg acatttctga atcgaacttg 1920
aaatacacca ccggtgacca tctagccatc tggccatcca actccgacga aaacatcaag 1980
caatttgcca agtgtttcgg attggaagat aaactcgaca ctgttattga attgaaggca 2040
ttggactcca cttacaccat tccattccca actccaatta cttacggtgc tgtcattaga 2100
caccatttag aaatctccgg tccagtctcg agacaattct tttgtcgat tgctgggttt 2160
gctcctgatg aagaaacaaa gaagactttc accagacttg gtggtgacaa acaagaattc 2220
gccaccaagg ttacccgcag aaagttcaac attgccgatg ccttgttata ttcctccaac 2280
aacactccat ggtccgatgt tccttttgag ttccttattg aaaacatcca acacttgact 2340
ccacgttact actccatttc ttcttcgtcg ttgagtgaaa aacaactcat caatgttact 2400
gcagtcgttg aggccgaaga agaagccgat ggcagaccag tcactggtgt tgttaccaac 2460
ttgttgaaga acattgaaat tgcgcaaaac aagactggcg aaaagccact tgttcactac 2520
gatttgagcg gcccaagagg caagttcaac aagttcaagt tgccagtgca cgtgagaaga 2580
tccaacttta agttgccaaa gaactccacc accccagtta tcttgattgg tccaggtact 2640
ggtgttgccc cattgagagg tttcgttaga gaaagagttc aacaagtcaa gaatggtgtc 2700
aatgttggca agactttgtt gttttatggt tgcagaaact ccaacgagga ctttttgtac 2760
aagcaagaat gggccgagta cgcttctgtt ttgggtgaaa actttgagat gttcaatgcc 2820
ttctccagac aagacccatc caagaaggtt tacgtccagg ataagatttt agaaaacagc 2880
caacttgtgc acgaattgtt gaccgaaggt gccattatct acgtctgtgg tgacgccagt 2940
```

FIG. 3A

```
agaatggcca gagacgtcca gaccacgatc tccaagattg ttgccaaaag cagagaaatc 3000
agtgaagaca aggccgctga attggtcaag tcctggaaag tccaaaatag ataccaagaa 3060
gatgtttggt agactcaaac gaatctctct ttctcccaac gcatttatga atattctcat 3120
tgaagtttta catatgttct atatttcatt ttttttttat tatattacga aacataggtc 3180
aactatatat acttgattaa atgttataga aacaataatt attatctact cgtctacttc 3240
tttggcattg gcattggcat tggcattggc attgccgttg ccgttggtaa tgccgggata 3300
tttagtacag tatctccaat ccggatttga gctattgtaa atcagctgca agtcattctc 3360
caccttcaac cagtacttat acttcatctt tgacttcaag tccaagtcat aaatattaca 3420
agttagcaag aacttctggc catccacaat atagacgtta ttcacgttat tatgcgacgt 3480
atggatatgg ttatccttat tgaacttctc aaacttcaaa aacaacccca cgtcccgcaa 3540
cgtcattatc aacgacaagt tctgactcac gtcgtcggag ctcgtcaagt tctcaattag 3600
atcgttcttg ttattgatct tctggtactt tctcaactgc tggaacacat tgtcctcgtt 3660
gttcaaatag atcttgaaca acttcttcaa gggaatcaac ttttcgatct gggccaagat 3720
ttccgccggg atcttcagaa acaagtcctg caacccctgg tcgatggtct cggggtacaa 3780
caagtctaag gggcagaagt gtctaggcac gtgtttcaac tggttcaagg aacatgttcg 3840
acagtagttc gagttatagt tatcgtacaa ccactttggc ttgatttcga aaatgacgga 3900
gctgatccca tcattctcct ggttcctttc atagtacaac tggcatttct tcgagagact 3960
caactcctcg tagttcccgt ccaagatatt cggcaacaag agcccgtagc gctcacggag 4020
catcaagtcg tggccctggt tgttcaactt gttgatgaag tccgatgtca agacaatcaa 4080
ctggatgtcg atgatctggt gcggaaacaa gttcttgcac tttagctcga tgaagtcgta 4140
caact                                                             4145
```

FIG. 3B

```
         10         20         30         40         50         60
ACATACTTCA AGCAGTTTGG CGACATAGTG AACCTCAAGT TATCACGGAA CAAGACGACG

         70         80         90        100        110        120
GGCAAGAGCA AGCACTACGG GTTTATAGAG TTCACGTCGC CTGAAGTTGC CCAGATCGCG

        130        140        150        160        170        180
GCGGAGACGA TGAACAACTA CTTGTTGTTT GGACACTTGA TCAAATGTGA GGTTGTCAGC

        190        200        210        220        230        240
GAGCCGTTCA AGGACTTGTT CAAGGACTCG AAGAGGAAGT TCAAGGTGAT TCCCTGGAAG

        250        260        270        280        290        300
AAGATCGCGA AGGATAAGCA CGATAAGCCA AAGTCCGCGA AGGAGTGGGC GAAGTTGGTG

        310        320        330        340        350        360
GAGAAGTTCG AAGAGTCCAA GAAGAAGAAG CAGGAGGAGT TGAAGAGTAA AGGTATTGAT

        370        380        390        400        410        420
TTTGATTTGG CTGCTATATA AAGGAGATAA GAGAGGAGGA TGACAAGCGC AAACGAGCAT

        430        440        450        460        470        480
TCTGTTGATG TGTAAAGCAG GTATAGATAA TAGCGGATAA CGTAAAATAA GAGATCTCCA

        490        500        510        520        530        540
ACTTCCAACT TCCAACTTCC GACCCTCATC TTTTGGGGGA GAGGGATTGG TATGTAGTGG

        550        560        570        580        590        600
TGAGGGAGAG GAGGATATTT TGTTTTGCCT AATTGGGATA AATTATCCCA GTCAGTTGAA

        610        620        630        640        650        660
AGAGCGAGGC GTAAGCCATT TCTTTTTCTA ACTGCAAATA GCATACAGAT GCGATAGTTA

        670        680        690        700        710        720
ACGAAGAGAG AAATCAAGAG CAGGTGACTA CATACATAGA TAGTGACATT ATAATAACAT

        730        740        750        760        770        780
GGCGCATCAT TGGTTCTATG TAGCTGGCAG GGTTATTATC AAGCTTGAAT AGTTTAATAA

        790        800        810        820        830        840
AAATCGTACC ATGAATGTAT GCATAGAAGC AATAAGGAAG CCTGTGCCTG TGAGTAGTAG

        850        860        870        880        890        900
CAGTAGCGGG GGGAGACGCT AGTTTAGGGG TAAAATGTCA GCACATGAAC AGCAGTTGAA

        910        920        930        940        950        960
GTGGGTGCCA ATCAAGTAAG AACATCTTGT GAAAAATCAA AAGCAATGGT ATATGTGTTC

        970        980        990       1000       1010       1020
CTGCATACAG TGCTGGAGTC AACGAGCCAA AAAAAAAAAA GAAAGAAAGA GAGAAAAACT

       1030       1040       1050       1060       1070       1080
TATCGTATAA AAACCACACA AAAATTTCCC AATCCCAATT CCTTCATTCT TCTTCTTTTA

       1090       1100       1110        1120         1130
CTGATTTAAC CCACAGATAC ATACAATT ATG ACC GAC ACA GAC ACC ACG ACC ACC
                               M   T   D   T   D   T   T   T   T>

   1140        1150        1160        1170        1180
ATC TAC ACC CAC GAA GAG GTT GCC CAG CAC ACC ACC CAC GAC GAC TTG
 I   Y   T   H   E   E   V   A   Q   H   T   T   H   D   D   L>
```

FIG. 4A 1190 1200 1210 1220 1230
TGG GTT ATT CTC AAT GGT AAG GTC TAC AAC ATC TCC AAC TAT ATA GAC
W V I L N G K V Y N I S N Y I D>

1240 1250 1260 1270
GAG CAC CCA GGT GGT GAA GAA GTC ATT CTT GAT TGC GCC GGC ACA GAC
E H P G G E E V I L D C A G T D>

1280 1290 1300 1310 1320
GCC ACT GAA GCC TTT GAC GAC ATT GGC CAC TCC GAC GAG GCC CAC GAG
A T E A F D D I G H S D E A H E>

1330 1340 1350 1360 1370
ATC TTG GAA AAG TTG TAC ATT GGT AAC TTG AAG GGC GCT AAG ATT GTT
I L E K L Y I G N L K G A K I V>

1380 1390 1400 1410 1420
GAG GCC AAG CAC GCG CAG TCG TTC AGC ACG GAA GAA GAC TCG GGT ATC
E A K H A Q S F S T E E D S G I>

1430 1440 1450 1460 1470
AAC TTC CCA TTG ATT GCT GTT GGT GTG TTT TTG GCT GCT TTC GGT GTC
N F P L I A V G V F L A A F G V>

1480 1490 1500 1510 1520
TAC TAC TAC AAG ACC AAC TTT GCC TAAGC ATAACAAGCA GTACAGTTGA
Y Y Y K T N F A>

1530 1540 1550 1560 1570 1580
AGGACAGGGT AGAGGAGATG AGAAAAAACG GGAACCCAAC AAAGATTATT TTCACACATC 1590 1600 1610 1620 1630 1640
ACATGGAGGG GCTGATCCCA CTTTTTGACG TCAATATCCA CAGCACGAAG AAAGAAAGAA 1650 1660 1670 1680 1690 1700
AGAAAGAAAG TCTATGGAAG AGGAAATGGA TCACATTAGA GCTTTTCTTT ATGTAACATA 1710 1720 1730 1740 1750 1760
TATATATATA TAAACTAATA CAGATTTACA GATACACCAC ATCACCGCAG GGCTTATCAT 1770 1780 1790 1800 1810 1820
CTGATGGTGC CCAAAAAAAA AAATCCACTG TGGATGAGCC TAGTTAGGAG ATATCGGAGT 1830 1840 1850 1860 1870 1880
AGCTCATTCT TTTGATATCT AGGTCTTCCT CTCTTGGATT CTACGTTGGT ACTTGGTGCT 1890 1900 1910 1920 1930 1940
ACACGATGAG ATCACCAGGT GTCATTCTGG AGTTTGGTGG AAAGTGTGTT GATTTTTTTA 1950 1960 1970 1980 1990 2000
GTAAGCAAGA ATTTGTTGAG TTCTATTGGA TGTTCTGGTG CGGCCACTTC CATCCCCCCA 2010 2020 2030 2040 2050 2060
CCCCTTGTCT TGTCTTGTCT TGTCTTATTT TTTTGGGTCG GTTGGCGGAA GTAAGACGCA 2070 2080 2090 2100 2110 2120
CGCACAGGAG GAGCACGACG GATAAATATC CACTTTTTTC ACACGCGTCG ATTGACGGCT 2130 2140 2150 2160 2170 2180
TGTGTGAATT GTGGGGAATA CGGATAAGGG GGTATACCAC ACACACACAT ATCTAACATA 2190 2200 2210 2220 2230 2240
TCAGACCACT TTCTATAACA GATCTCATGA TCCCCTTGAG AGTTGATGCA AGTCTATGCT

FIG. 4B

```
      2250       2260       2270       2280       2290       2300
CCTGTGATAT TGCCCCCCCC CCCCCAAGGA AGGGCGGGGC ATGTTATCAG GGACCTGGAT

      2310       2320       2330       2340       2350       2360
GAACCCTTGA TGGCGGTGTG AGTAGATGCA AGAGAGGTTG TGCTTTGGAA GTAGCTGAAG

      2370       2380       2390       2400       2410       2420
GTGTAGGGAC ATCCGGTACT ATAGTTCTCT TGAAGGATCA TGCCAGCTCC CTTTCTGTGG

      2430       2440       2450       2460       2470       2480
CTCTCTGGAA GCTCTGCATC TTCTCTTCGT TGAAACAGCG TGGAGTTACG AAAGGTACCC

      2490       2500       2510       2520       2530       2540
TGTGGTGAGT TCAAACAAGA CATGGCTCTA CAAGCTGTCG AGGATAAAAG TAATTAAACA

      2550       2560       2570       2580       2590       2600
ACATGTATAT ATATTAATAA ACGGATCCGT GGTGCTAGAT TGTGGTAGAT GTTTAGTATC

      2610       2620       2630       2640       2650       2660
GTTTATCACC TCTAGTGAAA ACTAGCATTT GATTCCATTA GTCATCAGTA CTTGATGTTA

      2670       2680       2690       2700       2710
CATTCAACCA AATGAAGGTC GGTCCAAGAT CCAAAGAATT CAAAAAGCTT
```

FIG. 4C 10 20 30 40 50 60 70
TTAATTAAATGCACGAAGCGGAGATAAAAGATTACGTAATTTATCTCCTGAGACAATTTTAGCCGTGTTC 80 90 100 110 120 130 140
ACACGCCCTTCTTTGTTCTGAGCGAAGGATAAATAATTAGACTTCCACAGCTCATTCTAATTTCCGTCAC 150 160 170 180 190 200 210
GCGAATATTGAAGGGGGGTACATGTGGCCGCTGAATGTGGGGGCAGTAAACGCAGTCTCTCCTCTCCCAC 220 230 240 250 260 270 280
GAATAGTGCAACGGAGGAAGGATAACGGATAGAAAGCGGAATGCGAGGAAAATTTTGAACGCGCAAGAAA 290 300 310 320 330 340 350
AGCAATATCCGGGCTACCAGGTTTTGAGCCAGGGAACACACTCCTATTTCTGCTCAATGACTGAACATAG 360 370 380 390 400 410 420
AAAAAACACCAAGACGCAATGAAACGCACATGGACATTTAGACCTCCCCACATGTGATAGTTTGTCTTAA 430 440 450 460 470 480 490
CAGAAAAGTATAATAAGAACCCATGCCGTCCCTTTTCTTTCGCCGCTTCAACTTTTTTTTTTATATCTTA 500 510 520 530 540
CACACATCACGACC ATG GCT TTA GAC AAG TTA GAT TTG TAT GTC ATC ATA ACA TTG
M A L D K L D L Y V I I T L>

550 560 570 580 590 600
GTG GTC GCT GTG GCC GCC TAT TTT GCC AAG AAC CAG TTC CTT GAT CAG CCC CAG
V V A V A A Y F A K N Q F L D Q P Q>

610 620 630 640 650
GAC ACC GGG TTC CTC AAC ACG GAC AGC GGA AGC AAC TCC AGA GAC GTC TTG CTG
D T G F L N T D S G S N S R D V L X>

660 670 680 690 700
ACA TTG AAG AAG AAT AAT AAA AAC ACG TTG TTG TTG TTT GGG TCC CAC ACC GGT
T L K K N N K N T L L L F G S Q T G>

710 720 730 740 750 760
ACG GCA GAA GAT TAC GCC AAC AAA TTG TCA AGA GAA TTG CAC TCC AGA TTT GGC
T A E D Y A N K L S R E L H S R F G>

770 780 790 800 810
TTG AAA ACC ATG GTT GCA GAT TTC GCT GAT TAC GAT TGG GAT AAC TTC GGA GAT
L K T M V A D F A D Y D W D N F G D>

820 830 840 850 860 870
ATC ACC GAA GAT ATC TTG GTG TTT TTC ATC GTT GCC ACC TAC GGT GAG GGT GAA
I T E D I L V F F I V A T Y G E G E>

880 890 900 910 920
CCT ACC GAC AAT GCC GAC GAG TTC CAC ACC TGG TTG ACT GAA GAA GCT GAC ACT
P T D N A D E F H T W L T E E A D T>

930 940 950 960 970
TTG AGT ACT TTG AGA TAT ACC GTG TTC GGG TTG GGT AAC TCC ACC TAC GAG TTC
L S T L R Y T V F G L G N S T Y E F>

FIG. 5A

```
980          990          1000         1010         1020         1030
TTC AAT GCT ATT GGT AGA AAG TTT GAC AGA TTG TTG AGT GAG AAA GGT GGT GAC
 F   N   A   I   G   R   K   F   D   R   L   L   S   E   K   G   G   D>

     1040         1050         1060         1070         1080
AGA TTT GCT GAA TAT GCT GAA GGT GAC GAC GGC ACT GGC ACC TTG GAC GAA GAT
 R   F   A   E   Y   A   E   G   D   D   G   T   G   T   L   D   E   D>

 1090         1100         1110         1120         1130         1140
TTC ATG GCC TGG AAG GAT AAT GTC TTT GAC GCC TTG AAG AAT GAC TTG AAC TTT
 F   M   A   W   K   D   N   V   F   D   A   L   K   N   D   L   N   F>

       1150         1160         1170         1180         1190
GAA GAA AAG GAA TTG AAG TAC GAA CCA AAC GTG AAA TTG ACT GAG AGA GAT GAC
 E   E   K   E   L   K   Y   E   P   N   V   K   L   T   E   R   D   D>

  1200         1210         1220         1230         1240
TTG TCT GCT GCC GAC TCC CAA GTT TCC TTG GGT GAG CCA AAC AAG AAG TAC ATC
 L   S   A   A   D   S   Q   V   S   L   G   E   P   N   K   K   Y   I>

1250         1260         1270         1280         1290         1300
AAC TCC GAG GGC ATC GAC TTG ACC AAG GGT CCA TTC GAC CAC ACC CAC CCA TAC
 N   S   E   G   I   D   L   T   K   G   P   F   D   H   T   H   P   Y>

     1310         1320         1330         1340         1350
TTG GCC AGG ATC ACC GAG ACC AGA GAG TTG TTC AGC TCC AAG GAA AGA CAC TGT
 L   A   R   I   T   E   T   R   E   L   F   S   S   K   E   R   H   C>

 1360         1370         1380         1390         1400         1410
ATT CAC GTT GAA TTT GAC ATT TCT GAA TCG AAC TTG AAA TAC ACC ACC GGT GAC
 I   H   V   E   F   D   I   S   E   S   N   L   K   Y   T   T   G   D>

       1420         1430         1440         1450         1460
CAT CTA GCC ATC TGG CCA TCC AAC TCC GAC GAA AAC ATC AAG CAA TTT GCC AAG
 H   L   A   I   W   P   S   N   S   D   E   N   I   K   Q   F   A   K>

  1470         1480         1490         1500         1510
TGT TTC GGA TTG GAA GAT AAA CTC GAC ACT GTT ATT GAA TTG AAG GCA TTG GAC
 C   F   G   L   E   D   K   L   D   T   V   I   E   L   K   A   L   D>

1520         1530         1540         1550         1560         1570
TCC ACT TAC ACC ATT CCA TTC CCA ACT CCA ATT ACT TAC GGT GCT GTC ATT AGA
 S   T   Y   T   I   P   F   P   T   P   I   T   Y   G   A   V   I   R>

     1580         1590         1600         1610         1620
CAC CAT TTA GAA ATC TCC GGT CCA GTC TCG AGA CAA TTC TTT TTG TCG ATT GCT
 H   H   L   E   I   S   G   P   V   S   R   Q   F   F   L   S   I   A>

 1630         1640         1650         1660         1670         1680
GGG TTT GCT CCT GAT GAA GAA ACA AAG AAG ACT TTC ACC AGA CTT GGT GGT GAC
 G   F   A   P   D   E   E   T   K   K   T   F   T   R   L   G   G   D>

       1690         1700         1710         1720         1730
AAA CAA GAA TTC GCC ACC AAG GTT ACC CGC AGA AAG TTC AAC ATT GCC GAT GCC
 K   Q   E   F   A   T   K   V   T   R   R   K   F   N   I   A   D   A>

```

```
TTG TTA TAT TCC TCC AAC AAC ACT CCA TGG TCC GAT GTT CCT TTT GAG TTC CTT
 L   L   Y   S   S   N   N   T   P   W   S   D   V   P   F   E   F   L>

1790      1800            1810          1820          1830           1840
 ATT GAA AAC ATC CAA CAC TTG ACT CCA CGT TAC TAC TCC ATT TCT TCT TCG TCG
  I   E   N   I   Q   H   L   T   P   R   Y   Y   S   I   S   S   S   S>

       1850         1860          1870          1880          1890
 TTG AGT GAA AAA CAA CTC ATC AAT GTT ACT GCA GTC GTT GAG GCC GAA GAA GAA
  L   S   E   K   Q   L   I   N   V   T   A   V   V   E   A   E   E   E>

  1900         1910          1920          1930          1940          1950
 GCC GAT GGC AGA CCA GTC ACT GGT GTT GTT ACC AAC TTG TTG AAG AAC ATT GAA
  A   D   G   R   P   V   T   G   V   V   T   N   L   L   K   N   I   E>

         1960         1970          1980          1990          2000
 ATT GCG CAA AAC AAG ACT GGC GAA AAG CCA CTT GTT CAC TAC GAT TTG AGC GGC
  I   A   Q   N   K   T   G   E   K   P   L   V   H   Y   D   L   S   G>

    2010         2020          2030          2040          2050
 CCA AGA GGT AAG TTC AAC AAG TTC AAG TTG CCA GTG CAC GTG AGA AGA TCC AAC
  P   R   G   K   F   N   K   F   K   L   P   V   H   V   R   R   S   N>

2060      2070            2080          2090          2100           2110
 TTT AAG TTG CCA AAG AAC TCC ACC ACC CCA GTT ATC TTG ATT GGT CCA GGT ACT
  F   K   L   P   K   N   S   T   T   P   V   I   L   I   G   P   G   T>

       2120         2130          2140          2150          2160
 GGT GTT GCC CCA TTG AGA GGT TTC GTT AGA GAA AGA GTT CAA CAA GTC AAG AAT
  G   V   A   P   L   R   G   F   V   R   E   R   V   Q   Q   V   K   N>

  2170         2180          2190          2200          2210          2220
 GGT GTC AAT GTT GGC AAG ACT TTG TTG TTT TAT GGT TGC AGA AAC TCC AAC GAG
  G   V   N   V   G   K   T   L   L   F   Y   G   C   R   N   S   N   E>

         2230         2240          2250          2260          2270
 GAC TTT TTG TAC AAG CAA GAA TGG GCC GAG TAC GCT TCT GTT TTG GGT GAA AAC
  D   F   L   Y   K   Q   E   W   A   E   Y   A   S   V   L   G   E   N>

    2280         2290          2300          2310          2320
 TTT GAG ATG TTC AAT GCC TTC TCT AGA CAA GAC CCA TCC AAG AAG GTT TAC GTC
  F   E   M   F   N   A   F   S   R   Q   D   P   S   K   K   V   Y   V>

2330      2340            2350          2360          2370           2380
 CAG GAT AAG ATT TTA GAA AAC AGC CAA CTT GTG CAC GAA TTG TTG ACC GAA GGT
  Q   D   K   I   L   E   N   S   Q   L   V   H   E   L   L   T   E   G>

       2390         2400          2410          2420          2430
 GCC ATT ATC TAC GTC TGT GGT GAC GCC AGT AGA ATG GCC AGA GAC GTC CAG ACC
  A   I   I   Y   V   C   G   D   A   S   R   M   A   R   D   V   Q   T>

  2440         2450          2460          2470          2480          2490
 ACG ATC TCC AAG ATT GTT GCC AAA AGC AGA GAA ATC AGT GAA GAC AAG GCC GCT
  T   I   S   K   I   V   A   K   S   R   E   I   S   E   D   K   A   A>

         2500         2510          2520          2530          2540
 GAA TTG GTC AAG TCC TGG AAA GTC CAA AAT AGA TAC CAA GAA GAT GTT TGG
  E   L   V   K   S   W   K   V   Q   N   R   Y   Q   E   D   V   W>
```

FIG. 5C

```
         2550      2560      2570      2580      2590
TAGACTCAAACGAATCTCTCTTTCTCCCAACGCATTTATGAATATTCTC

         2600      2610      2620      2630      2640      2650      2660
ATTGAAGTTTTACATATGTTCTATATTTCATTTTTTTTTTTTATTATATTACGAAACATAGGTCAACTAT

         2670      2680      2690      2700      2710      2720      2730
ATATACTTGATTAAATGTTATAGAAACAATAATTATTATCTACTCGTCTACTTCTTTGGCATTGGCATTG

         2740      2750      2760      2770      2780      2790      2800
GCATTGGCATTGGCATTGCCGTTGCCGTTGGTAATGCCGGGATATTTAGTACAGTATCTCCAATCCGGAT

         2810      2820      2830      2840      2850      2860      2870
TTGAGCTATTGTAAATCAGCTGCAAGTCATTCTCCACCTTCAACCAGTACTTATACTTCATCTTTGACTT

         2880      2890      2900      2910      2920      2930      2940
CAAGTCCAAGTCATAAATATTACAAGTTAGCAAGAACTTCTGGCCATCCACAATATAGACGGTTATTCAC

         2950      2960      2970      2980      2990      3000      3010
GTTATTATGCGACGTATGGATATGGTTATCCTTATTGAACTTCTCAAACTTCAAAAACAACCCCACGTCC

         3020      3030      3040
CGCAACGTCATTATCAACGACATTAATTAA
```

FIG. 5D 3908 nucleotides

LacZα fragment: bases 1-571
M13 reverse priming site: bases 205-221
Multiple cloning site: bases 234-357
T7 promoter/priming site: bases 364-383
M13 Forward (-20) priming site: bases 391-406
M13 Forward (-40) priming site: bases 411-426
f1 origin: bases 548-962
Kanamycin resistance ORF: bases 1296-2090
Ampicillin resistance ORF: bases 2108-2968
ColE1 origin: bases 3113-3786

10 20 30 40 50 60 70 80 90 100
GGTACCGAGC TCACGAGTTT TGGGATTTTC GAGTTTGGAT TGTTTCCTTT GTTGATTGAA TTGACGAAAC CAGAGGTTTT CAAGACAGAT AAGATTGGGT 110 120 130 140 150 160 170 180 190 200
TTATCAAAAC GCAGTTTGAA ATATTCCAGT TGGTTTCCAA GATATCTTGA AGAAGATTGA CGATTTGAAA TTTCAAGAAG TGGAGAAGAT CTGGTTTGGA 210 220 230 240 250 260 270 280 290 300
TTGTTGGAGA ATTTCAAGAA TCTCAAGATT TACTCTAACG ACGGGTACAA CGAGAATTGT ATTGAATTGA TCAAGAACAT GATCTTGGTG TTACAGAACA 310 320 330 340 350 360 370 380 390 400
TCAAGTTCTT GGACCAGACT GAGAATGCCA CAGATATACA AGGCGTCATG TGATAAAATG GATGAGATTT ATCCCACAAT TGAAGAAAGA GTTTATGGAA 410 420 430 440 450 460 470 480 490 500
AGTGGTCAAC CAGAAGCTAA ACAGGAAGAA GCAAACGAAG AGGTGAAACA AGAAGAAGAA GGTAAATAAG TATTTTGTAT TATATAACAA ACAAAGTAAG 510 520 530 540 550 560 570 580 590 600
GAATAGAGAT TTATACAATA AATTGCCATA CTAGTCACGT GAGATATCTC ATCCATTCCC CAACTCCCAA GAAAAAAAAA AAGTGAAAAA AAAAATCAAA 610 620 630 640 650 660 670 680 690 700
CCCAAAGATC AACCTCCCCA TCATCATCGT CATCAAACCC CCAGCTCAAT TCGCAATGGT TAGCACAAAA ACATACACAG AAAGGGCATC AGCACACCCC
M V S T K T Y T E R A S A H P>

710 720 730 740 750 760 770 780 790 800
TCCAAGGTTG CCCAACGTTT ATTCCGCTTA ATGGAGTCCA AAAAGACCAA CCTCTGCGCC TCGATCGACG TCACCACAAC CGCCGAGTTC CTTTCGCTCA
S K V A Q R L F R L M E S K K T N L C A S I D V T T T A E F L S L>

810 820 830 840 850 860 870 880 890 900
TCGACAAGCT CGGTCCCCAC ATCTGTCTCG TGAAGACGCA CATCGATATC ATCTCAGACT TCAGCTACGA GGGCACGATT GAGCCGTTGC TTGTGCTTGC
I D K L G P H I C L V K T H I D I I S D F S Y E G T I E P L L V L A>

910 920 930 940 950 960 970 980 990 1000
AGAGCGCCAC GGGTTCTTGA TATTCGAGGA CAGGAAGTTT GCTGATATCG GAAACACCGT GATGTTGCAG TACACCTCGG GGGTATACCG GATCGCGGCG
E R H G F L I F E D R K F A D I G N T V M L Q Y T S G V Y R I A A>

1010 1020 1030 1040 1050 1060 1070 1080 1090 1100
TGGAGTGACA TCACGAACGC GCACGGAGTG ACTGGGAAGG GCGTCGTTGA AGGGTTGAAA CGCGGTGCGG AGGGGGTAGA AAAGGAAAGG CGCGTGTTGA
W S D I T N A H G V T G K G V V E G L K R G A E G V E K E R G V L>

1110 1120 1130 1140 1150 1160 1170 1180 1190 1200
TGTTGGCGGA GTTGTCGAGT AAAGGCTCGT TGGCGCATGG TGAATATACC CGTGAGACGA TCGAGATTGC GAAGAGTGAT CGGGAGTTCG TGATTGGGTT
M L A E L S S K G S L A H G E Y T R E T I E I A K S D R E F V I G F>

1210 1220 1230 1240 1250 1260 1270 1280 1290 1300
CATCGCGCAG CGGGACATGG GGGGTAGAGA AGAAGGGTTT GATTGGATCA TCATGACGCC TGGTGTGGGG TTGGATGATA AAGGCGATGC GTTGGGCCAG
I A Q R D M G G R E E G F D W I I M T P G V G L D D K G D A L G Q>

1310 1320 1330 1340 1350 1360 1370 1380 1390 1400
CAGTATAGGA CTGTTGATGA GGTGGTTCTG ACTGGTACGG ATGTGATTAT TGTCGGGAGA GGGTTGTTTG GAAAAGGAAG AGACCCTGAG GTGGAGGGAA
Q Y R T V D E V V L T G T D V I I V G R G L F G K G R D P E V E G>

1410 1420 1430 1440 1450 1460 1470 1480 1490 1500
AGAGATACAG GGATGCTGGA TGGAAGGCAT ACTTGAAGAG AACTGGTCAG TTAGAATAAA TATTGTAATA AATAGGTCTA TATACATACA CTAAGCTTCT
K R Y R D A G W K A Y L K R T G Q L E *>

1510 1520 1530 1540 1550 1560 1570 1580 1590 1600
AGGACGTCAT TGTAGTCTTC GAAGTTGTCT GCTAGTTTAG TTCTCATCAT TTCGAAAACC AATAACGCAA TGGATGTAGC AGGGATGGTG GTTAGTGCGT 1610 1620 1630 1640 1650 1660 1670 1680 1690 1700
TCCTCACAAA CCCAGAGTAC GCCCCCTCAA ACCACGTCAC ATTCGCCCTT TGCTTCATCC GCATCACTTG CTTGAAGGTA TCCACGTACG AGTTGTAATA

1710
CACCTTGAAC AA

FIG. 8

ATGCACGAAGCGGAGATAAAAGATTACGTAATTTATCTCCTGAGACAATTTTAGCCGTGTTCACACGCCCTTCTTT
GTTCTGAGCGAAGGATAAATAATTAGACTTCCACAGCTCATTCTAATTTCCGTCAGGGAATATTGAAGGGGGGTA
CATGTGGCCGCTGAATGTGGGGGCAGTAAACGCAGTCTCTCCTCTCCCAGGAATAGTGCAACGGAGGAAGGATAAC
GGATAGAAAGCGGAATGCGAGGAAAATTTTGAACGCGCAAGAAAAGCAATATCCGGGCTACCAGGTTTTGAGCCAG
GGAACACACTCCTATTTCTGCTCAATGACTGAACATAGAAAAAACACCAAGACGCAATGAAACGCACATGGACATT
TAGACCTCCCCACATGTGATAGTTTGTCTTAACAGAAAAGTATAATAAGAACCCATGCCGTCCCTTTTCTTTCGCC
GCTTCAACTTTTTTTTTTTATCTTACACACATCACGACCATGATTGAACAACTCCTAGAATATTGGTATGTCGTT
GTGCCAGTGTTGTACATCATCAAACAACTCCTTGCATACACAAAGACTCGCGTCTTGATGAAAAAGTTGGGTGCTG
CTCCAGTCACAAACAAGTTGTACGACAACGCTTTCGGTATCGTCAATGGATGGAAGGCTCTCCAGTTCAAGAAAGA
GGGCAGGGCTCAAGAGTACAACGATTACAAGTTTGACCACTCCAAGAACCCAAGCGTGGGCACCTACGTCAGTATT
CTTTTCGGCACCAGGATCGTCGTGACCAAAGATCCAGAGAATATCAAAGCTATTTTGGCAACCCAGTTTGGTGATT
TTTCTTTGGGCAAGAGGCACACTCTTTTTAAGCCTTTGTTAGGTGATGGGATCTTCACATTGGACGGCGAAGGCTG
GAAGCACAGCAGAGCCATGTTGAGACCACAGTTTGCCAGAGAACAAGTTGCTCATGTGACGTCGTTGGAACCACAC
TTCCAGTTGTTGAAGAAGCATATTCTTAAGCACAAGGGTGAATACTTTGATATCCAGGAATTGTTCTTTAGATTTA
CCGTTGATTCGGCCACGGAGTTCTTATTTGGTGAGTCCGTGCACTCCTTAAAGGACGAATCTATTGGTATCAACCA
AGACGATATAGATTTTGCTGGTAGAAAGGACTTTGCTGAGTCGTTCAACAAAGCCCAGGAATACTTGGCTATTAGA
ACCTTGGTGCAGACGTTCTACTGGTTGGTCAACAACAAGGAGTTTAGAGACTGTACCAAGCTGGTGCACAAGTTCA
CCAACTACTATGTTCAGAAAGCTTTGGATGCTAGCCCAGAAGAGCTTGAAAAGCAAAGTGGGTATGTGTTCTTGTA
CGAGCTTGTCAAGCAGACAAGAGACCCCAATGTGTTGCGTGACCAGTCTTTGAACATCTTGTTGGCCGGAAGAGAC
ACCACTGCTGGGTTGTTGTCGTTTGCTGTCTTTGAGTTGGCCAGACACCCAGAGATCTGGGCCAAGTTGAGAGAGG
AAATTGAACAACAGTTTGGTCTTGGAGAAGACTCTCGTGTTGAAGAGATTACCTTTGAGAGCTTGAAGAGATGTGA
GTACTTGAAAGCGTTCCTTAATGAAACCTTGCGTATTTACCCAAGTGTCCCAAGAAACTTCAGAATCGCCACCAAG
AACACGACATTGCCAAGGGGCGGTGGTTCAGACGGTACCTCGCCAATCTTGATCCAAAAGGGAGAAGCTGTGTCGT
ATGGTATCAACTCTACTCATTTGGACCCTGTCTATTACGGCCCTGATGCTGCTGAGTTCAGACCAGAGAGATGGTT
TGAGCCATCAACCAAAAAGCTCGGCTGGGCTTACTTGCCATTCAACGGTGGTCCAAGAATCTGTTTGGGTCAGCAG
TTTGCCTTGACGGAAGCTGGCTATGTGTTGGTTAGATTGGTGCAAGAGTTCTCCCACGTTAGGCTGGACCCAGACG
AGGTGTACCCGCCAAAGAGGTTGACCAACTTGACCATGTTGTTTGCAGGATGGTGCTATTGTCAAGTTTGACTAGCG
GCGTGGTGAATGCGTTTGATTTTGTAGTTTCTGTTTGCAGTAATGAGATAACTATTCAGATAAGGCGAGTGGATGT
ACGTTTTGTAAGAGTTTCCTTACAACCTTGGTGGGGTGTGTGAGGTTGAGGTTGCATCTTGGGGAGATTACACCTT
TTGCAGCTCTCCGTATACACTTGTACTCTTTGTAACCTCTATCAATCATGTGGGGGGGGGGTTCATTGTTTGGCC
ATGGTGGTGCATGTTAAATCCGCCAACTACCCAATCTCACATGAAACTCAAGCACACTAAAAAAAAAAAAGATGTT
GGGGGAAAACTTTGGTTTCCCTTCTTAGTAATTAAACACTCTCACTCTCACTCTCACTCTCTCCACTCAGACAAAC
CAACCACCTGGGCTGCAGACAACCAGAAAAAAAAAGAACAAAATCCAGATAGAAAAACAAAGGGCTGGACAACCAT
AAATAAACAATCTAGGGTCTACTCCATCTTCCACTGTTCTTCTTCTTCAGACTTAGCTAACAAACAACTCACTTC
ACCATGGATTACGCAGGCATCACGCGTGGCTCCATCAGAGGCGAGGCCTTGAAGAAACTCGCAGAATTGACCATCC
AGAACCAGCCATCCAGCTTGAAAGAAATCAACACCGGCATCCAGAAGGACGACTTTGCCAAGTT

FIG. 11

SEQUENCE LISTING

<160> NUMBER OF SEQ ID NOS: 34

<210> SEQ ID NO 1
<211> LENGTH: 3948
<212> TYPE: DNA
<213> ORGANISM: Candida tropicalis
<400> SEQUENCE: 1

```
gacctgtgac gcttccggtg tcttgccacc agtctccaag ttgaccgacg cccaagtcat     60
gtaccacttt atttccggtt acacttccaa gatggctggt actgaagaag gtgtcacgga    120
accacaagct actttctccg cttgtttcgg tcaaccattc ttggtgttgc acccaatgaa    180
gtacgctcaa caattgtctg acaagatctc gcaacacaag gctaacgcct ggttgttgaa    240
caccggttgg gttggttctt ctgctgctag aggtggtaag agatgctcat tgaagtacac    300
cagagccatt ttggacgcta tccactctgg tgaattgtcc aaggttgaat acgaaacttt    360
cccagtcttc aacttgaatg tcccaacctc ctgtccaggt gtcccaagtg aaatcttgaa    420
cccaaccaag gcctggaccg gaaggtgttg actccttcaa caaggaaatc aagtctttgg    480
ctggtaagtt tgctgaaaac ttcaagacct atgctgacca agctaccgct gaagtgagag    540
ctgcaggtcc agaagcttaa agatatttat tcattattta gtttgcctat ttatttctca    600
ttacccatca tcattcaaca ctatatataa agttacttcg gatatcattg taatcgtgcg    660
tgtcgcaatt ggatgatttg gaactgcgct tgaaacggat tcatgcacga agcggagata    720
aaagattacg taatttatct cctgagacaa ttttagccgt gttcacacgc ccttctttgt    780
tctgagcgaa ggataaataa ttagacttcc acagctcatt ctaatttccg tcacgcgaat    840
attgaagggg ggtacatgtg gccgctgaat gtgggggcag taaacgcagt ctctcctctc    900
ccaggaatag tgcaacggag gaaggataac ggatagaaag cggaatgcga ggaaaatttt    960
gaacgcgcaa gaaaagcaat atccgggcta ccaggttttg agccagggaa cacactccta   1020
tttctgctca atgactgaac atagaaaaaa caccaagacg caatgaaacg cacatggaca   1080
tttagacctc cccacatgtg atagtttgtc ttaacagaaa agtataataa gaacccatgc   1140
cgtccctttt ctttcgccgc ttcaactttt ttttttttat cttacacaca tcacgaccat   1200
gactgtacac gatattatcg ccacatactt caccaaatgg tacgtgatag taccactcgc   1260
tttgattgct tatagagtcc tcgactactt ctatggcaga tacttgatgt acaagcttgg   1320
tgctaaacca tttttccaga aacagacaga cggctgtttc ggattcaaag ctccgcttga   1380
attgttgaag aagaagagcg acggtaccct catagacttc acactccagc gtatccacga   1440
tctcgatcgt cccgatatcc caactttcac attcccggtc ttttccatca accttgtcaa   1500
tacccttgag ccggagaaca tcaaggccat cttggccact cagttcaacg atttctcctt   1560
gggtaccaga cactcgcact ttgctccttt gttgggtgat ggtatcttta cgttggatgg   1620
cgccggctgg aagcacagca gatctatgtt gagaccacag tttgccagag aacagatttc   1680
ccacgtcaag ttgttggagc cacacgttca ggtgttcttc aaacacgtca gaaaggcaca   1740
gggcaagact tttgacatcc aggaattgtt tttcagattg accgtcgact ccgccaccga   1800
gtttttgttt ggtgaatccg ttgagtcctt gagagatgaa tctatcggca tgtccatcaa   1860
tgcgcttgac tttgacggca aggctggctt tgctgatgct tttaactatt cgcagaatta   1920
tttggcttcg agagcggtta tgcaacaatt gtactgggtg ttgaacggga aaaagtttaa   1980
ggagtgcaac gctaaagtgc acaagtttgc tgactactac gtcaacaagg ctttggactt   2040
```

-continued

```
gacgcctgaa caattggaaa agcaggatgg ttatgtgttt ttgtacgaat tggtcaagca   2100

aaccagagac aagcaagtgt tgagagacca attgttgaac atcatggttg ctggtagaga   2160

caccaccgcc ggtttgttgt cgtttgtttt ctttgaattg gccagaaacc cagaagttac   2220

caacaagttg agagaagaaa ttgaggacaa gtttggactc ggtgagaatg ctagtgttga   2280

agacatttcc tttgagtcgt tgaagtcctg tgaatacttg aaggctgttc tcaacgaaac   2340

cttgagattg tacccatccg tgccacagaa tttcagagtt gccaccaaga acactaccct   2400

cccaagaggt ggtggtaagg acgggttgtc tcctgttttg gtgagaaagg gtcagaccgt   2460

tatttacggt gtctacgcag cccacagaaa cccagctgtt tacggtaagg acgctcttga   2520

gtttagacca gagagatggt ttgagccaga gacaaagaag cttggctggg ccttcctccc   2580

attcaacggt ggtccaagaa tctgtttggg acagcagttt gccttgacag aagcttcgta   2640

tgtcactgtc aggttgctcc aggagtttgc acacttgtct atggacccag acaccgaata   2700

tccacctaag aaaatgtcgc atttgaccat gtcgcttttc gacggtgcca atattgagat   2760

gtattagagg gtcatgtgtt attttgattg tttagtttgt aattactgat taggttaatt   2820

catggattgt tatttattga taggggtttg cgcgtgttgc attcacttgg gatcgttcca   2880

ggttgatgtt tccttccatc ctgtcgagtc aaaaggagtt ttgtttttgta actccggacg   2940

atgttttaaa tagaaggtcg atctccatgt gattgttttg actgttactg tgattatgta   3000

atctgcggac gttatacaag catgtgattg tggttttgca gccttttgca cgacaaatga   3060

tcgtcagacg attacgtaat ctttgttaga ggggtaaaaa aaaacaaaat ggcagccaga   3120

atttcaaaca ttctgcaaac aatgcaaaaa atgggaaact ccaacagaca aaaaaaaaaa   3180

ctccgcagca ctccgaaccc acagaacaat ggggcgccag aattattgac tattgtgact   3240

tttttacgct aacgctcatt gcagtgtagt gcgtcttaca cggggtattg ctttctacaa   3300

tgcaagggca cagttgaagg tttgcaccta acgttgcccc gtgtcaactc aatttgacga   3360

gtaacttcct aagctcgaat tatgcagctc gtgcgtcaac ctatgtgcag gaaagaaaaa   3420

atccaaaaaa atcgaaaatg cgactttcga ttttgaataa accaaaaaga aaaatgtcgc   3480

acttttttct cgctctcgct ctctcgaccc aaatcacaac aaatcctcgc gcgcagtatt   3540

tcgacgaaac cacaacaaat aaaaaaaaca aattctacac cacttctttt tcttcaccag   3600

tcaacaaaaa acaacaaatt atacaccatt tcaacgattt ttgctcttat aaatgctata   3660

taatggttta attcaactca ggtatgttta ttttactgtt ttcagctcaa gtatgttcaa   3720

atactaacta cttttgatgt ttgtcgcttt tctagaatca aaacaacgcc cacaacacgc   3780

cgagcttgtc gaatagacgg tttgtttact cattagatgg tcccagatta cttttcaagc   3840

caaagtctct cgagttttgt ttgctgtttc cccaattcct aactatgaag ggtttttata   3900

aggtccaaag accccaaggc atagtttttt tggttccttc ttgtcgtg                3948
```

<210> SEQ ID NO 2
<211> LENGTH: 4206
<212> TYPE: DNA
<213> ORGANISM: Candida tropicalis

<400> SEQUENCE: 2

```
catcaagatc atctatgggg ataattacga cagcaacatt gcagaaagag cgttggtcac     60

aatcgaaaga gcctatggcg ttgccgtcgt tgaggcaaat gacagcacca acaataacga    120

tggtcccagt gaagagcctt cagaacagtc cattgttgac gcttaaggca cggataatta    180
```

-continued

```
cgtggggcaa aggaacgcgg aattagttat ggggggatca aaagcggaag atttgtgttg    240
cttgtgggtt ttttccttta tttttcatat gatttctttg cgcaagtaac atgtgccaat    300
ttagtttgtg attagcgtgc cccacaattg gcatcgtgga cgggcgtgtt ttgtcatacc    360
ccaagtctta actagctcca cagtctcgac ggtgtctcga cgatgtcttc ttccacccct    420
cccatgaatc attcaaagtt gttgggggat ctccaccaag ggcaccggag ttaatgctta    480
tgtttctccc actttggttg tgattggggt agtctagtga gttggagatt ttcttttttt    540
cgcaggtgtc tccgatatcg aaatttgatg aatatagaga gaagccagat cagcacagta    600
gattgccttt gtagttagag atgttgaaca gcaactagtt gaattacacg ccaccacttg    660
acagcaagtg cagtgagctg taaacgatgc agccagagtg tcaccaccaa ctgacgttgg    720
gtggagttgt tgttgttgtt gttggcaggg ccatattgct aaacgaagac aagtagcaca    780
aaacccaagc ttaagaacaa aaataaaaaa aattcatacg acaattccaa agccattgat    840
ttacataatc aacagtaaga cagaaaaaac tttcaacatt tcaaagttcc ctttttccta    900
ttacttcttt tttttcttct ttccttcttt ccttctgttt ttcttacttt atcagtcttt    960
tacttgtttt tgcaattcct catcctcctc ctactcctcc tcaccatggc tttagacaag   1020
ttagatttgt atgtcatcat aacattggtg gtcgctgtag ccgcctattt tgctaagaac   1080
cagttccttg atcagcccca ggacaccggg ttcctcaaca cggacagcgg aagcaactcc   1140
agagacgtct tgctgacatt gaagaagaat aataaaaaca cgttgttgtt gtttgggtcc   1200
cagacgggta cggcagaaga ttacgccaac aaattgtcca gagaattgca ctccagattt   1260
ggcttgaaaa cgatggttgc agatttcgct gattacgatt gggataactt cggagatatc   1320
accgaagaca tcttggtgtt tttcattgtt gccacctatg gtgagggtga acctaccgat   1380
aatgccgacg agttccacac ctggttgact gaagaagctg acactttgag taccttgaaa   1440
tacaccgtgt tcgggttggg taactccacg tacgagttct tcaatgccat tggtagaaag   1500
tttgacagat tgttgagcga gaaaggtggt gacaggtttg ctgaatacgc tgaaggtgat   1560
gacggtactg gcaccttgga cgaagatttc atggcctgga aggacaatgt ctttgacgcc   1620
ttgaagaatg atttgaactt tgaagaaaag gaattgaagt acgaaccaaa cgtgaaattg   1680
actgagagag acgacttgtc tgctgctgac tcccaagttt ccttgggtga gccaaacaag   1740
aagtacatca actccgaggg catcgacttg accaagggtc cattcgacca cacccaccca   1800
tacttggcca gaatcaccga gacgagagag ttgttcagct ccaaggacag acactgtatc   1860
cacgttgaat ttgacatttc tgaatcgaac ttgaaataca ccaccggtga ccatctagct   1920
atctggccat ccaactccga cgaaaacatt aagcaatttg ccaagtgttt cggattggaa   1980
gataaactcg acactgttat tgaattgaag gcgttggact ccacttacac catcccattc   2040
ccaaccccaa ttacctacgg tgctgtcatt agacaccatt tagaaatctc cggtccagtc   2100
tcgagacaat tctttttgtc aattgctggg tttgctcctg atgaagaaac aaagaaggct   2160
tttaccagac ttggtggtga caagcaagaa ttcgccgcca aggtcacccg cagaaagttc   2220
aacattgccg atgccttgtt atattcctcc aacaacgctc catggtccga tgttcctttt   2280
gaattcctta ttgaaaacgt tccacacttg actccacgtt actactccat ttcgtcttcg   2340
tcattgagtg aaaagcaact catcaacgtt actgcagttg ttgaagccga agaagaagct   2400
gatggcagac cagtcactgg tgttgtcacc aacttgttga agaacgttga aattgtgcaa   2460
aacaagactg gcgaaaagcc acttgtccac tacgatttga gcggcccaag aggcaagttc   2520
aacaagttca agttgccagt gcatgtgaga agatccaact ttaagttgcc aaagaactcc   2580
```

-continued

```
accaccccag ttatcttgat tggtccaggt actggtgttg ccccattgag aggttttgtc   2640
agagaaagag ttcaacaagt caagaatggt gtcaatgttg gcaagacttt gttgttttat   2700
ggttgcagaa actccaacga ggactttttg tacaagcaag aatgggccga gtacgcttct   2760
gttttgggtg aaaactttga gatgttcaat gccttctcca gacaagaccc atccaagaag   2820
gtttacgtcc aggataagat tttagaaaac agccaacttg tgcacgagtt gttgactgaa   2880
ggtgccatta tctacgtctg tggtgatgcc agtagaatgg ctagagacgt gcagaccaca   2940
atttccaaga ttgttgctaa aagcagagaa attagtgaag acaaggctgc tgaattggtc   3000
aagtcctgga aggtccaaaa tagataccaa gaagatgttt ggtagactca aacgaatctc   3060
tctttctccc aacgcattta tgaatcttta ttctcattga agctttacat atgttctaca   3120
ctttattttt tttttttttt ttattattat attacgaaac ataggtcaac tatatatact   3180
tgattaaatg ttatagaaac aataactatt atctactcgt ctacttcttt ggcattgaca   3240
tcaacattac cgttcccatt accgttgccg ttggcaatgc cgggatattt agtacagtat   3300
ctccaatccg gatttgagct attgtagatc agctgcaagt cattctccac cttcaaccag   3360
tacttatact tcatctttga cttcaagtcc aagtcataaa tattacaagt tagcaagaac   3420
ttctggccat ccacgatata gacgttattc acgttattat gcgacgtatg gatgtggtta   3480
tccttattga acttctcaaa cttcaaaaac aaccccacgt cccgcaacgt cattatcaac   3540
gacaagttct ggctcacgtc gtcggagctc gtcaagttct caattagatc gttcttgtta   3600
ttgatcttct ggtactttct caattgctgg aacacattgt cctcgttgtt caaatagatc   3660
ttgaacaact ttttcaacgg gatcaacttc tcaatctggg ccaagatctc cgccgggatc   3720
ttcagaaaca agtcctgcaa cccctggtcg atggtctccg ggtacaacaa gtccaagggg   3780
cagaagtgtc taggcacgtg tttcaactgg ttcaacgaac atgttcgaca gtagttcgag   3840
ttatagttat cgtacaacca ttttggtttg atttcgaaaa tgacggagct gatgccatca   3900
ttctcctggt tcctctcata gtacaactgg cacttcttcg agaggctcaa ttcctcgtag   3960
ttcccgtcca agatattcgg caacaagagc ccgtaccgct cacggagcat caagtcgtgg   4020
ccctggttgt tcaacttgtt gatgaagtcc gaggtcaaga caatcaactg gatgtcgatg   4080
atctggtgcg ggaacaagtt cttgcatttt agctcgatga agtcgtacaa ctcacacgtc   4140
gagatatact cctgttcctc cttcaagagc cggatccgca agagcttgtg cttcaagtag   4200
tcgttg                                                              4206
```

<210> SEQ ID NO 3
<211> LENGTH: 4145
<212> TYPE: DNA
<213> ORGANISM: Candida tropicalis

<400> SEQUENCE: 3

```
tatatgatat atgatatatc ttcctgtgta attattattc gtattcgtta atacttacta     60
catttttttt tctttattta tgaagaaaag gagagttcgt aagttgagtt gagtagaata    120
ggctgttgtg catacgggga gcagaggaga gtatccgacg aggaggaact gggtgaaatt    180
tcatctatgc tgttgcgtcc tgtactgtac tgtaaatctt agatttccta gaggttgttc    240
tagcaaataa agtgtttcaa gatacaattt tacaggcaag ggtaaaggat caactgatta    300
gcggaagatt ggtgttgcct gtggggttct tttatttttc atatgatttc tttgcgcgag    360
taacatgtgc caatctagtt tatgattagc gtacctccac aattggcatc ttggacgggc    420
```

-continued

```
gtgttttgtc ttaccccaag ccttatttag ttccacagtc tcgacggtgt ctcgccgatg    480
tcttctccca cccctcgcag gaatcattcg aagttgttgg gggatctcct ccgcagttta    540
tgttcatgtc tttcccactt tggttgtgat tggggtagcg tagtgagttg gtgattttct    600
tttttcgcag gtgtctccga tatcgaagtt tgatgaatat aggagccaga tcagcatggt    660
atattgcctt tgtagataga gatgttgaac aacaactagc tgaattacac accaccgcta    720
aacgatgcgc acagggtgtc accgccaact gacgttgggt ggagttgttg ttggcagggc    780
catattgcta aacgaagaga agtagcacaa aacccaaggt taagaacaat taaaaaaatt    840
catacgacaa ttccacagcc atttacataa tcaacagcga caaatgagac agaaaaaact    900
ttcaacattt caaagttccc tttttcctat tacttctttt tttctttcct tcctttcatt    960
tcctttcctt ctgcttttat tactttacca gtcttttgct tgtttttgca attcctcatc   1020
ctcctcctca ccatggcttt agacaagtta gatttgtatg tcatcataac attggtggtc   1080
gctgtggccg cctattttgc taagaaccag ttccttgatc agccccagga caccgggttc   1140
ctcaacacgg acagcggaag caactccaga gacgtcttgc tgacattgaa gaagaataat   1200
aaaaacacgt tgttgttgtt tgggtcccag accggtacgg cagaagatta cgccaacaaa   1260
ttgtcaagag aattgcactc cagatttggc ttgaaaacca tggttgcaga tttcgctgat   1320
tacgattggg ataacttcgg agatatcacc gaagatatct tggtgttttt catcgttgcc   1380
acctacggtg agggtgaacc taccgacaat gccgacgagt tccacacctg gttgactgaa   1440
gaagctgaca ctttgagtac tttgagatat accgtgttcg ggttgggtaa ctccacctac   1500
gagttcttca atgctattgg tagaaagttt gacagattgt tgagtgagaa aggtggtgac   1560
agatttgctg aatatgctga aggtgacgac ggcactggca ccttggacga agatttcatg   1620
gcctggaagg ataatgtctt tgacgccttg aagaatgact tgaactttga agaaaaggaa   1680
ttgaagtacg aaccaaacgt gaaattgact gagagagatg acttgtctgc tgccgactcc   1740
caagtttcct tgggtgagcc aaacaagaag tacatcaact ccgagggcat cgacttgacc   1800
aagggtccat tcgaccacac ccacccatac ttggccagga tcaccgagac cagagagttg   1860
ttcagctcca aggaaagaca ctgtattcac gttgaatttg acatttctga atcgaacttg   1920
aaatacacca ccggtgacca tctagccatc tggccatcca actccgacga aaacatcaag   1980
caatttgcca agtgtttcgg attggaagat aaactcgaca ctgttattga attgaaggca   2040
ttggactcca cttacaccat tccattccca actccaatta cttacggtgc tgtcattaga   2100
caccatttag aaatctccgg tccagtctcg agacaattct tttgtcgat  tgctgggttt   2160
gctcctgatg aagaaacaaa gaagactttc accagacttg gtggtgacaa acaagaattc   2220
gccaccaagg ttacccgcag aaagttcaac attgccgatg ccttgttata ttcctccaac   2280
aacactccat ggtccgatgt tccttttgag ttccttattg aaaacatcca acacttgact   2340
ccacgttact actccatttc ttcttcgtcg ttgagtgaaa aacaactcat caatgttact   2400
gcagtcgttg aggccgaaga agaagccgat ggcagaccag tcactggtgt tgttaccaac   2460
ttgttgaaga acattgaaat tgcgcaaaac aagactggcg aaaagccact tgttcactac   2520
gatttgagcg gcccaagagg caagttcaac aagttcaagt tgccagtgca cgtgagaaga   2580
tccaacttta agttgccaaa gaactccacc accccagtta tcttgattgg tccaggtact   2640
ggtgttgccc cattgagagg tttcgttaga gaaagagttc aacaagtcaa gaatggtgtc   2700
aatgttggca agactttgtt gttttatggt tgcagaaact ccaacgagga ctttttgtac   2760
```

-continued

```
aagcaagaat gggccgagta cgcttctgtt ttgggtgaaa actttgagat gttcaatgcc   2820
ttctctagac aagacccatc caagaaggtt tacgtccagg ataagatttt agaaaacagc   2880
caacttgtgc acgaattgtt gaccgaaggt gccattatct acgtctgtgg tgacgccagt   2940
agaatggcca gagacgtcca gaccacgatc tccaagattg ttgccaaaag cagagaaatc   3000
agtgaagaca aggccgctga attggtcaag tcctggaaag tccaaaatag ataccaagaa   3060
gatgtttggt agactcaaac gaatctctct ttctcccaac gcatttatga atattctcat   3120
tgaagtttta catatgttct atatttcatt ttttttttat tatattacga aacataggtc   3180
aactatatat acttgattaa atgttataga aacaataatt attatctact cgtctacttc   3240
tttggcattg gcattggcat tggcattggc attgccgttg ccgttggtaa tgccgggata   3300
tttagtacag tatctccaat ccggatttga gctattgtaa atcagctgca agtcattctc   3360
caccttcaac cagtacttat acttcatctt tgacttcaag tccaagtcat aaatattaca   3420
agttagcaag aacttctggc catccacaat atagacgtta ttcacgttat tatgcgacgt   3480
atggatatgg ttatccttat tgaacttctc aaacttcaaa aacaacccca cgtcccgcaa   3540
cgtcattatc aacgacaagt tctgactcac gtcgtcggag ctcgtcaagt tctcaattag   3600
atcgttcttg ttattgatct tctggtactt tctcaactgc tggaacacat tgtcctcgtt   3660
gttcaaatag atcttgaaca acttcttcaa gggaatcaac ttttcgatct gggccaagat   3720
ttccgccggg atcttcagaa acaagtcctg caacccctgg tcgatggtct cggggtacaa   3780
caagtctaag gggcagaagt gtctaggcac gtgtttcaac tggttcaagg aacatgttcg   3840
acagtagttc gagttatagt tatcgtacaa ccactttggc ttgatttcga aaatgacgga   3900
gctgatccca tcattctcct ggttcctttc atagtacaac tggcatttct tcgagagact   3960
caactcctcg tagttcccgt ccaagatatt cggcaacaag agcccgtagc gctcacggag   4020
catcaagtcg tggccctggt tgttcaactt gttgatgaag tccgatgtca agacaatcaa   4080
ctggatgtcg atgatctggt gcggaaacaa gttcttgcac tttagctcga tgaagtcgta   4140
caact                                                               4145
```

```
<210> SEQ ID NO 4
<211> LENGTH: 2710
<212> TYPE: DNA
<213> ORGANISM: Candida tropicalis

<400> SEQUENCE: 4

acatacttca agcagtttgg cgacatagtg aacctcaagt tatcacggaa caagacgacg     60
ggcaagagca agcactacgg gtttatagag ttcacgtcgc ctgaagttgc ccagatcgcg    120
gcggagacga tgaacaacta cttgttgttt ggacacttga tcaaatgtga ggttgtcagc    180
gagccgttca aggacttgtt caaggactcg aagaggaagt tcaaggtgat tccctggaag    240
aagatcgcga aggataagca cgataagcca aagtccgcga aggagtgggc gaagttggtg    300
gagaagttcg aagagtccaa gaagaagaag caggaggagt tgaagagtaa aggtattgat    360
tttgatttgg ctgctatata aaggagataa gagaggagga tgacaagcgc aaacgagcat    420
tctgttgatg tgtaaagcag gtatagataa tagcggataa cgtaaaataa gagatctcca    480
acttccaact tccaacttcc gaccctcatc ttttgggggga gagggattgg tatgtagtgg   540
tgagggagag gaggatattt tgttttgcct aattgggata aattatccca gtcagttgaa    600
agagcgaggc gtaagccatt tctttttcta actgcaaata gcatacagat gcgatagtta    660
```

-continued

```
acgaagagag aaatcaagag caggtgacta catacataga tagtgacatt ataataacat    720

ggcgcatcat tggttctatg tagctggcag ggttattatc aagcttgaat agtttaataa    780

aaatcgtacc atgaatgtat gcatagaagc aataaggaag cctgtgcctg tgagtagtag    840

cagtagcggg gggagacgct agtttagggg taaaatgtca gcacatgaac agcagttgaa    900

gtgggtgcca atcaagtaag aacatcttgt gaaaaatcaa aagcaatggt atatgtgttc    960

ctgcatacag tgctggagtc aacgagccaa aaaaaaaaaa gaaagaaaga gagaaaaact   1020

tatcgtataa aaaccacaca aaaatttccc aatcccaatt ccttcattct tcttctttta   1080

ctgatttaac ccacagatac atacaattat gaccgacaca gacaccacga ccaccatcta   1140

cacccacgaa gaggttgccc agcacaccac ccacgacgac ttgtgggtta ttctcaatgg   1200

taaggtctac aacatctcca actatataga cgagcaccca ggtggtgaag aagtcattct   1260

tgattgcgcc ggcacagacg ccactgaagc ctttgacgac attggccact ccgacgaggc   1320

ccacgagatc ttggaaaagt tgtacattgg taacttgaag ggcgctaaga ttgttgaggc   1380

caagcacgcg cagtcgttca gcacggaaga agactcgggt atcaacttcc cattgattgc   1440

tgttggtgtg tttttggctg ctttcggtgt ctactactac aagaccaact ttgcctaagc   1500

ataacaagca gtacagttga aggacagggt agaggagatg agaaaaaacg ggaacccaac   1560

aaagattatt ttcacacatc acatggaggg gctgatccca ctttttgacg tcaatatcca   1620

cagcacgaag aaagaaagaa agaaagaaag tctatggaag aggaaatgga tcacattaga   1680

gcttttcttt atgtaacata tatatatata taaactaata cagatttaca gatacaccac   1740

atcaccgcag ggcttatcat ctgatggtgc ccaaaaaaaa aaatccactg tggatgagcc   1800

tagttaggag atatcggagt agctcattct tttgatatct aggtcttcct ctcttggatt   1860

ctacgttggt acttggtgct acacgatgag atcaccaggt gtcattctgg agtttggtgg   1920

aaagtgtgtt gattttttta gtaagcaaga atttgttgag ttctattgga tgttctggtg   1980

cggccacttc catcccccca ccccttgtct tgtcttgtct tgtcttattt ttttgggtcg   2040

gttggcggaa gtaagacgca cgcacaggag gagcacgacg gataaatatc cactttttttc  2100

acacgcgtcg attgacggct tgtgtgaatt gtggggaata cggataaggg ggtataccac   2160

acacacacat atctaacata tcagaccact ttctataaca gatctcatga tccccttgag   2220

agttgatgca agtctatgct cctgtgatat tgcccccccc cccccaagga agggcggggc   2280

atgttatcag ggacctggat gaacccttga tggcggtgtg agtagatgca agagaggttg   2340

tgctttggaa gtagctgaag gtgtagggac atccggtact atagttctct tgaaggatca   2400

tgccagctcc ctttctgtgg ctctctggaa gctctgcatc ttctcttcgt tgaaacagcg   2460

tggagttacg aaaggtaccc tgtggtgagt tcaaacaaga catggctcta caagctgtcg   2520

aggataaaag taattaaaca acatgtatat atattaataa acggatccgt ggtgctagat   2580

tgtggtagat gtttagtatc gtttatcacc tctagtgaaa actagcattt gattccatta   2640

gtcatcagta cttgatgtta cattcaacca aatgaaggtc ggtccaagat ccaaagaatt   2700

caaaaagctt                                                          2710
```

<210> SEQ ID NO 5
<211> LENGTH: 129
<212> TYPE: PRT
<213> ORGANISM: Candida tropicalis

<400> SEQUENCE: 5

Met Thr Asp Thr Asp Thr Thr Thr Thr Ile Tyr Thr His Glu Glu Val

-continued

```
1               5                   10                  15

Ala Gln His Thr Thr His Asp Asp Leu Trp Val Ile Leu Asn Gly Lys
            20                  25                  30

Val Tyr Asn Ile Ser Asn Tyr Ile Asp Glu His Pro Gly Gly Glu Glu
        35                  40                  45

Val Ile Leu Asp Cys Ala Gly Thr Asp Ala Thr Glu Ala Phe Asp Asp
    50                  55                  60

Ile Gly His Ser Asp Glu Ala His Glu Ile Leu Glu Lys Leu Tyr Ile
65                  70                  75                  80

Gly Asn Leu Lys Gly Ala Lys Ile Val Glu Ala Lys His Ala Gln Ser
                85                  90                  95

Phe Ser Thr Glu Glu Asp Ser Gly Ile Asn Phe Pro Leu Ile Ala Val
            100                 105                 110

Gly Val Phe Leu Ala Ala Phe Gly Val Tyr Tyr Tyr Lys Thr Asn Phe
        115                 120                 125

Ala
```

<210> SEQ ID NO 6
<211> LENGTH: 32
<212> TYPE: DNA
<213> ORGANISM: Primer

<400> SEQUENCE: 6
ccttaattaa atgcacgaag cggagataaa ag 32

<210> SEQ ID NO 7
<211> LENGTH: 21
<212> TYPE: DNA
<213> ORGANISM: Primer

<400> SEQUENCE: 7
gtctaaagcc atggtcgtga t 21

<210> SEQ ID NO 8
<211> LENGTH: 22
<212> TYPE: DNA
<213> ORGANISM: Primer

<400> SEQUENCE: 8
aacatggctt tagacaagtt ag 22

<210> SEQ ID NO 9
<211> LENGTH: 32
<212> TYPE: DNA
<213> ORGANISM: Primer

<400> SEQUENCE: 9
ccttaattaa tgtcgttgat aatgacgttg cg 32

<210> SEQ ID NO 10
<211> LENGTH: 3037
<212> TYPE: DNA
<213> ORGANISM: Candida tropicalis

<400> SEQUENCE: 10
ttaattaaat gcacgaagcg gagataaaag attacgtaat ttatctcctg agacaatttt 60
agccgtgttc acacgccctt ctttgttctg agcgaaggat aaataattag acttccacag 120
ctcattctaa tttccgtcac gcgaatattg aagggggta catgtggccg ctgaatgtgg 180

-continued

```
gggcagtaaa cgcagtctct cctctcccag gaatagtgca acggaggaag gataacggat    240

agaaagcgga atgcgaggaa aattttgaac gcgcaagaaa agcaatatcc gggctaccag    300

gttttgagcc agggaacaca ctcctatttc tgctcaatga ctgaacatag aaaaaacacc    360

aagacgcaat gaaacgcaca tggacattta gacctcccca catgtgatag tttgtcttaa    420

cagaaaagta taataagaac ccatgccgtc ccttttcttt cgccgcttca actttttttt    480

ttatatctta cacacatcac gaccatggct ttagacaagt tagatttgta tgtcatcata    540

acattggtgg tcgctgtggc cgcctatttt gccaagaacc agttccttga tcagccccag    600

gacaccgggt tcctcaacac ggacagcgga agcaactcca gagacgtctt gctgacattg    660

aagaagaata ataaaaacac gttgttgttg tttgggtccc agaccggtac ggcagaagat    720

tacgccaaca aattgtcaag agaattgcac tccagatttg gcttgaaaac catggttgca    780

gatttcgctg attacgattg ggataacttc ggagatatca ccgaagatat cttggtgttt    840

ttcatcgttg ccacctacgg tgagggtgaa cctaccgaca atgccgacga gttccacacc    900

tggttgactg aagaagctga cactttgagt actttgagat ataccgtgtt cgggttgggt    960

aactccacct acgagttctt caatgctatt ggtagaaagt ttgacagatt gttgagtgag   1020

aaaggtggtg acagatttgc tgaatatgct gaaggtgacg acggcactgg caccttggac   1080

gaagatttca tggcctggaa ggataatgtc tttgacgcct tgaagaatga cttgaacttt   1140

gaagaaaagg aattgaagta cgaaccaaac gtgaaattga ctgagagaga tgacttgtct   1200

gctgccgact cccaagtttc cttgggtgag ccaaacaaga agtacatcaa ctccgagggc   1260

atcgacttga ccaagggtcc attcgaccac acccacccat acttggccag gatcaccgag   1320

accagagagt tgttcagctc caaggaaaga cactgtattc acgttgaatt tgacatttct   1380

gaatcgaact tgaaatacac caccggtgac catctagcca tctggccatc caactccgac   1440

gaaaacatca agcaatttgc caagtgtttc ggattggaag ataaactcga cactgttatt   1500

gaattgaagg cattggactc cacttacacc attccattcc caactccaat tacttacggt   1560

gctgtcatta gacaccattt agaaatctcc ggtccagtct cgagacaatt ctttttgtcg   1620

attgctgggt ttgctcctga tgaagaaaca aagaagactt tcaccagact tggtggtgac   1680

aaacaagaat tcgccaccaa ggttacccgc agaaagttca acattgccga tgccttgtta   1740

tattcctcca acaacactcc atggtccgat gttccttttg agttccttat tgaaaacatc   1800

caacacttga ctccacgtta ctactccatt tcttcttcgt cgttgagtga aaaacaactc   1860

atcaatgtta ctgcagtcgt tgaggccgaa gaagaagccg atggcagacc agtcactggt   1920

gttgttacca acttgttgaa gaacattgaa attgcgcaaa acaagactgg cgaaaagcca   1980

cttgttcact acgatttgag cggcccaaga ggtaagttca acaagttcaa gttgccagtg   2040

cacgtgagaa gatccaactt taagttgcca aagaactcca ccaccccagt tatcttgatt   2100

ggtccaggta ctggtgttgc cccattgaga ggtttcgtta gagaaagagt tcaacaagtc   2160

aagaatggtg tcaatgttgg caagactttg ttgttttatg gttgcagaaa ctccaacgag   2220

gactttttgt acaagcaaga atgggccgag tacgcttctg ttttgggtga aaactttgag   2280

atgttcaatg ccttctctag acaagaccca tccaagaagg tttacgtcca ggataagatt   2340

ttagaaaaca gccaacttgt gcacgaattg ttgaccgaag gtgccattat ctacgtctgt   2400

ggtgacgcca gtagaatggc cagagacgtc cagaccacga tctccaagat tgttgccaaa   2460

agcagagaaa tcagtgaaga caaggccgct gaattggtca agtcctggaa agtccaaaat   2520

agataccaag aagatgtttg gtagactcaa acgaatctct ctttctccca acgcatttat   2580
```

-continued

```
gaatattctc attgaagttt tacatatgtt ctatatttca ttttttttt attatattac   2640

gaaacatagg tcaactatat atacttgatt aaatgttata gaaacaataa ttattatcta   2700

ctcgtctact tctttggcat tggcattggc attggcattg gcattgccgt tgccgttggt   2760

aatgccggga tatttagtac agtatctcca atccggattt gagctattgt aaatcagctg   2820

caagtcattc tccaccttca accagtactt atacttcatc tttgacttca agtccaagtc   2880

ataaatatta caagttagca agaacttctg gccatccaca atatagacgt tattcacgtt   2940

attatgcgac gtatggatat ggttatcctt attgaacttc tcaaacttca aaaacaaccc   3000

cacgtcccgc aacgtcatta tcaacgacat taattaa                             3037
```

<210> SEQ ID NO 11
<211> LENGTH: 679
<212> TYPE: PRT
<213> ORGANISM: Candida tropicalis
<220> FEATURE:
<221> NAME/KEY: MISC_FEATURE
<222> LOCATION: (50)..(50)
<223> OTHER INFORMATION: Xaa=leucine or serine

<400> SEQUENCE: 11

```
Met Ala Leu Asp Lys Leu Asp Leu Tyr Val Ile Ile Thr Leu Val Val
1               5                   10                  15

Ala Val Ala Ala Tyr Phe Ala Lys Asn Gln Phe Leu Asp Gln Pro Gln
            20                  25                  30

Asp Thr Gly Phe Leu Asn Thr Asp Ser Gly Ser Asn Ser Arg Asp Val
        35                  40                  45

Leu Xaa Thr Leu Lys Lys Asn Asn Lys Asn Thr Leu Leu Leu Phe Gly
    50                  55                  60

Ser Gln Thr Gly Thr Ala Glu Asp Tyr Ala Asn Lys Leu Ser Arg Glu
65                  70                  75                  80

Leu His Ser Arg Phe Gly Leu Lys Thr Met Val Ala Asp Phe Ala Asp
                85                  90                  95

Tyr Asp Trp Asp Asn Phe Gly Asp Ile Thr Glu Asp Ile Leu Val Phe
            100                 105                 110

Phe Ile Val Ala Thr Tyr Gly Glu Gly Glu Pro Thr Asp Asn Ala Asp
        115                 120                 125

Glu Phe His Thr Trp Leu Thr Glu Glu Ala Asp Thr Leu Ser Thr Leu
    130                 135                 140

Arg Tyr Thr Val Phe Gly Leu Gly Asn Ser Thr Tyr Glu Phe Phe Asn
145                 150                 155                 160

Ala Ile Gly Arg Lys Phe Asp Arg Leu Leu Ser Glu Lys Gly Gly Asp
                165                 170                 175

Arg Phe Ala Glu Tyr Ala Glu Gly Asp Asp Gly Thr Gly Thr Leu Asp
            180                 185                 190

Glu Asp Phe Met Ala Trp Lys Asp Asn Val Phe Asp Ala Leu Lys Asn
        195                 200                 205

Asp Leu Asn Phe Glu Glu Lys Glu Leu Lys Tyr Glu Pro Asn Val Lys
    210                 215                 220

Leu Thr Glu Arg Asp Asp Leu Ser Ala Ala Asp Ser Gln Val Ser Leu
225                 230                 235                 240

Gly Glu Pro Asn Lys Lys Tyr Ile Asn Ser Glu Gly Ile Asp Leu Thr
                245                 250                 255

Lys Gly Pro Phe Asp His Thr His Pro Tyr Leu Ala Arg Ile Thr Glu
            260                 265                 270
```

-continued

```
Thr Arg Glu Leu Phe Ser Ser Lys Glu Arg His Cys Ile His Val Glu
        275                 280                 285

Phe Asp Ile Ser Glu Ser Asn Leu Lys Tyr Thr Thr Gly Asp His Leu
    290                 295                 300

Ala Ile Trp Pro Ser Asn Ser Asp Glu Asn Ile Lys Gln Phe Ala Lys
305                 310                 315                 320

Cys Phe Gly Leu Glu Asp Lys Leu Asp Thr Val Ile Glu Leu Lys Ala
                325                 330                 335

Leu Asp Ser Thr Tyr Thr Ile Pro Phe Pro Thr Pro Ile Thr Tyr Gly
            340                 345                 350

Ala Val Ile Arg His His Leu Glu Ile Ser Gly Pro Val Ser Arg Gln
        355                 360                 365

Phe Phe Leu Ser Ile Ala Gly Phe Ala Pro Asp Glu Glu Thr Lys Lys
    370                 375                 380

Thr Phe Thr Arg Leu Gly Gly Asp Lys Gln Glu Phe Ala Thr Lys Val
385                 390                 395                 400

Thr Arg Arg Lys Phe Asn Ile Ala Asp Ala Leu Leu Tyr Ser Ser Asn
                405                 410                 415

Asn Thr Pro Trp Ser Asp Val Pro Phe Glu Phe Leu Ile Glu Asn Ile
            420                 425                 430

Gln His Leu Thr Pro Arg Tyr Tyr Ser Ile Ser Ser Ser Ser Leu Ser
        435                 440                 445

Glu Lys Gln Leu Ile Asn Val Thr Ala Val Val Glu Ala Glu Glu Glu
    450                 455                 460

Ala Asp Gly Arg Pro Val Thr Gly Val Val Thr Asn Leu Leu Lys Asn
465                 470                 475                 480

Ile Glu Ile Ala Gln Asn Lys Thr Gly Glu Lys Pro Leu Val His Tyr
                485                 490                 495

Asp Leu Ser Gly Pro Arg Gly Lys Phe Asn Lys Phe Lys Leu Pro Val
            500                 505                 510

His Val Arg Arg Ser Asn Phe Lys Leu Pro Lys Asn Ser Thr Thr Pro
        515                 520                 525

Val Ile Leu Ile Gly Pro Gly Thr Gly Val Ala Pro Leu Arg Gly Phe
    530                 535                 540

Val Arg Glu Arg Val Gln Gln Val Lys Asn Gly Val Asn Val Gly Lys
545                 550                 555                 560

Thr Leu Leu Phe Tyr Gly Cys Arg Asn Ser Asn Glu Asp Phe Leu Tyr
                565                 570                 575

Lys Gln Glu Trp Ala Glu Tyr Ala Ser Val Leu Gly Glu Asn Phe Glu
            580                 585                 590

Met Phe Asn Ala Phe Ser Arg Gln Asp Pro Ser Lys Lys Val Tyr Val
        595                 600                 605

Gln Asp Lys Ile Leu Glu Asn Ser Gln Leu Val His Glu Leu Leu Thr
    610                 615                 620

Glu Gly Ala Ile Ile Tyr Val Cys Gly Asp Ala Ser Arg Met Ala Arg
625                 630                 635                 640

Asp Val Gln Thr Thr Ile Ser Lys Ile Val Ala Lys Ser Arg Glu Ile
                645                 650                 655

Ser Glu Asp Lys Ala Ala Glu Leu Val Lys Ser Trp Lys Val Gln Asn
            660                 665                 670

Arg Tyr Gln Glu Asp Val Trp
        675
```

-continued

<210> SEQ ID NO 12
<211> LENGTH: 23
<212> TYPE: DNA
<213> ORGANISM: Primer

<400> SEQUENCE: 12
cacaccaccc acgacgactt gtg 23

<210> SEQ ID NO 13
<211> LENGTH: 21
<212> TYPE: DNA
<213> ORGANISM: Primer

<400> SEQUENCE: 13
cttccgtgct gaacgactgc g 21

<210> SEQ ID NO 14
<211> LENGTH: 46
<212> TYPE: DNA
<213> ORGANISM: Primer

<400> SEQUENCE: 14
taatacgact cactataggg aggcacacca cccacgacga cttgtg 46

<210> SEQ ID NO 15
<211> LENGTH: 42
<212> TYPE: DNA
<213> ORGANISM: Primer

<400> SEQUENCE: 15
cttccgtgct gaacgactgc gaatcttagc gcccttcaag tt 42

<210> SEQ ID NO 16
<211> LENGTH: 39
<212> TYPE: DNA
<213> ORGANISM: Primer

<400> SEQUENCE: 16
ataagaatgc ggccgctgaa cgagaaccac atccaggag 39

<210> SEQ ID NO 17
<211> LENGTH: 33
<212> TYPE: DNA
<213> ORGANISM: Primer

<400> SEQUENCE: 17
ccttaattaa ggataaccac atccatacgt cgc 33

<210> SEQ ID NO 18
<211> LENGTH: 24
<212> TYPE: DNA
<213> ORGANISM: Primer

<400> SEQUENCE: 18
tgtgtcggtc atggtcgtga tgtg 24

<210> SEQ ID NO 19
<211> LENGTH: 24
<212> TYPE: DNA
<213> ORGANISM: Primer

<400> SEQUENCE: 19
cacatcacga ccatgaccga caca 24

-continued

<210> SEQ ID NO 20
<211> LENGTH: 30
<212> TYPE: DNA
<213> ORGANISM: Primer

<400> SEQUENCE: 20
cccttaatta agggggggatg gaagtggccg 30

<210> SEQ ID NO 21
<211> LENGTH: 33
<212> TYPE: DNA
<213> ORGANISM: Primer

<400> SEQUENCE: 21
aggcgcgccg gagtccaaaa agaccaacct ctg 33

<210> SEQ ID NO 22
<211> LENGTH: 34
<212> TYPE: DNA
<213> ORGANISM: Primer

<400> SEQUENCE: 22
ccttaattaa tacgtggata ccttcaagca agtg 34

<210> SEQ ID NO 23
<211> LENGTH: 1712
<212> TYPE: DNA
<213> ORGANISM: Candida tropicalis

<400> SEQUENCE: 23
ggtaccgagc tcacgagttt tgggattttc gagtttggat tgtttccttt gttgattgaa 60
ttgacgaaac cagaggtttt caagacagat aagattgggt ttatcaaaac gcagtttgaa 120
atattccagt tggtttccaa gatatcttga agaagattga cgatttgaaa tttgaagaag 180
tggagaagat ctggtttgga ttgttggaga atttcaagaa tctcaagatt tactctaacg 240
acgggtacaa cgagaattgt attgaattga tcaagaacat gatcttggtg ttacagaaca 300
tcaagttctt ggaccagact gagaatgcca cagatataca aggcgtcatg tgataaaatg 360
gatgagattt atcccacaat tgaagaaaga gtttatggaa agtggtcaac cagaagctaa 420
acaggaagaa gcaaacgaag aggtgaaaca agaagaagaa ggtaaataag tattttgtat 480
tatataacaa acaaagtaag gaatacagat ttatacaata aattgccata ctagtcacgt 540
gagatatctc atccattccc caactcccaa gaaaaaaaaa aagtgaaaaa aaaaatcaaa 600
cccaaagatc aacctcccca tcatcatcgt catcaaaccc ccagctcaat tcgcaatggt 660
tagcacaaaa acatacacag aaagggcatc agcacacccc tccaaggttg cccaacgttt 720
attccgctta atggagtcca aaaagaccaa cctctgcgcc tcgatcgacg tgaccacaac 780
cgccgagttc ctttcgctca tcgacaagct cggtccccac atctgtctcg tgaagacgca 840
catcgatatc atctcagact tcagctacga gggcacgatt gagccgttgc ttgtgcttgc 900
agagcgccac gggttcttga tattcgagga caggaagttt gctgatatcg gaaacaccgt 960
gatgttgcag tacacctcgg gggtataccg gatcgcggcg tggagtgaca tcacgaacgc 1020
gcacggagtg actgggaagg gcgtcgttga agggttgaaa cgcggtgcgg agggggtaga 1080
aaaggaaagg ggcgtgttga tgttggcgga gttgtcgagt aaaggctcgt tggcgcatgg 1140
tgaatatacc cgtgagacga tcgagattgc gaagagtgat cgggagttcg tgattgggtt 1200

-continued

```
catcgcgcag cgggacatgg ggggtagaga agaagggttt gattggatca tcatgacgcc   1260

tggtgtgggg ttggatgata aaggcgatgc gttgggccag cagtatagga ctgttgatga   1320

ggtggttctg actggtaccg atgtgattat tgtcgggaga gggttgtttg gaaaaggaag   1380

agaccctgag gtggagggaa agagatacag ggatgctgga tggaaggcat acttgaagag   1440

aactggtcag ttagaataaa tattgtaata aataggtcta tatacataca ctaagcttct   1500

aggacgtcat tgtagtcttc gaagttgtct gctagtttag ttctcatgat ttcgaaaacc   1560

aataacgcaa tggatgtagc agggatggtg gttagtgcgt tcctgacaaa cccagagtac   1620

gccgcctcaa accacgtcac attcgccctt tgcttcatcc gcatcacttg cttgaaggta   1680

tccacgtacg agttgtaata caccttgaag aa                                 1712


<210> SEQ ID NO 24
<211> LENGTH: 267
<212> TYPE: PRT
<213> ORGANISM: Candida tropicalis

<400> SEQUENCE: 24

Met Val Ser Thr Lys Thr Tyr Thr Glu Arg Ala Ser Ala His Pro Ser
1               5                   10                  15

Lys Val Ala Gln Arg Leu Phe Arg Leu Met Glu Ser Lys Lys Thr Asn
            20                  25                  30

Leu Cys Ala Ser Ile Asp Val Thr Thr Thr Ala Glu Phe Leu Ser Leu
        35                  40                  45

Ile Asp Lys Leu Gly Pro His Ile Cys Leu Val Lys Thr His Ile Asp
    50                  55                  60

Ile Ile Ser Asp Phe Ser Tyr Glu Gly Thr Ile Glu Pro Leu Leu Val
65                  70                  75                  80

Leu Ala Glu Arg His Gly Phe Leu Ile Phe Glu Asp Arg Lys Phe Ala
                85                  90                  95

Asp Ile Gly Asn Thr Val Met Leu Gln Tyr Thr Ser Gly Val Tyr Arg
            100                 105                 110

Ile Ala Ala Trp Ser Asp Ile Thr Asn Ala His Gly Val Thr Gly Lys
        115                 120                 125

Gly Val Val Glu Gly Leu Lys Arg Gly Ala Glu Gly Val Glu Lys Glu
    130                 135                 140

Arg Gly Val Leu Met Leu Ala Glu Leu Ser Ser Lys Gly Ser Leu Ala
145                 150                 155                 160

His Gly Glu Tyr Thr Arg Glu Thr Ile Glu Ile Ala Lys Ser Asp Arg
                165                 170                 175

Glu Phe Val Ile Gly Phe Ile Ala Gln Arg Asp Met Gly Gly Arg Glu
            180                 185                 190

Glu Gly Phe Asp Trp Ile Ile Met Thr Pro Gly Val Gly Leu Asp Asp
        195                 200                 205

Lys Gly Asp Ala Leu Gly Gln Gln Tyr Arg Thr Val Asp Glu Val Val
    210                 215                 220

Leu Thr Gly Thr Asp Val Ile Ile Val Gly Arg Gly Leu Phe Gly Lys
225                 230                 235                 240

Gly Arg Asp Pro Glu Val Glu Gly Lys Arg Tyr Arg Asp Ala Gly Trp
                245                 250                 255

Lys Ala Tyr Leu Lys Arg Thr Gly Gln Leu Glu
            260                 265


<210> SEQ ID NO 25
```

-continued

<211> LENGTH: 35
<212> TYPE: DNA
<213> ORGANISM: Primer

<400> SEQUENCE: 25
ccttaattaa gctcacgagt tttgggattt tcgag 35

<210> SEQ ID NO 26
<211> LENGTH: 35
<212> TYPE: DNA
<213> ORGANISM: Primer

<400> SEQUENCE: 26
gggtttaaac cgcagaggtt ggtctttttg gactc 35

<210> SEQ ID NO 27
<211> LENGTH: 4399
<212> TYPE: DNA
<213> ORGANISM: vector

<400> SEQUENCE: 27
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccgggggc 420
gcgccggagt ccaaaaagac caacctctgc gcctcgatcg acgtgaccac aaccgccgag 480
ttcctttcgc tcatcgacaa gctcggtccc cacatctgtc tcgtgaagac gcacatcgat 540
atcatctcag acttcagcta cgagggcacg attgagccgt tgcttgtgct tgcagagcgc 600
cacgggttct tgatattcga ggacaggaag tttgctgata tcggaaacac cgtgatgttg 660
cagtacacct cgggggtata ccggatcgcg gcgtggagtg acatcacgaa cgcgcacgga 720
gtgactggga agggcgtcgt tgaagggttg aaacgcggtg cggagggggt agaaaaggaa 780
aggggcgtgt tgatgttggc ggagttgtcg agtaaaggct cgttggcgca tggtgaatat 840
acccgtgaga cgatcgagat tgcgaagagt gatcgggagt tcgtgattgg gttcatcgcg 900
cagcgggaca tgggggggtag agaagaaggg tttgattgga tcatcatgac gcctggtgtg 960
gggttggatg ataaaggcga tgcgttgggc cagcagtata ggactgttga tgaggtggtt 1020
ctgactggta ccgatgtgat tattgtcggg agagggttgt ttggaaaagg aagagaccct 1080
gaggtggagg gaaagagata cagggatgct ggatggaagg catacttgaa gagaactggt 1140
cagttagaat aaatattgta ataaatagt ctatatacat acactaagct tctaggacgt 1200
cattgtagtc ttcgaagttg tctgctagtt tagttctcat gatttcgaaa accaataacg 1260
caatggatgt agcagggatg gtggttagtg cgttcctgac aaacccagag tacgccgcct 1320
caaaccacgt cacattcgcc ctttgcttca tccgcatcac ttgcttgaag gtatccacgt 1380
attaattaag ctcacgagtt ttgggatttt cgagtttgga ttgtttcctt tgttgattga 1440
attgacgaaa ccagaggttt tcaagacaga taagattggg tttatcaaaa cgcagtttga 1500
aatattccag ttggtttcca agatatcttg aagaagattg acgatttgaa atttgaagaa 1560
gtggagaaga tctggtttgg attgttggag aatttcaaga atctcaagat ttactctaac 1620

-continued

```
gacgggtaca acgagaattg tattgaattg atcaagaaca tgatcttggt gttacagaac   1680
atcaagttct tggaccagac tgagaatgcc acagatatac aaggcgtcat gtgataaaat   1740
ggatgagatt tatcccacaa ttgaagaaag agtttatgga aagtggtcaa ccagaagcta   1800
aacaggaaga agcaaacgaa gaggtgaaac aagaagaaga aggtaaataa gtattttgta   1860
ttatataaca aacaaagtaa ggaatacaga tttatacaat aaattgccat actagtcacg   1920
tgagatatct catccattcc ccaactccca agaaaaaaaa aaagtgaaaa aaaaaatcaa   1980
acccaaagat caacctcccc atcatcatcg tcatcaaacc cccagctcaa ttcgcaatgg   2040
ttagcacaaa aacatacaca gaaagggcat cagcacaccc ctccaaggtt gcccaacgtt   2100
tattccgctt aatggagtcc aaaaagacca acctctgcgg tttaaacctg caggcatgca   2160
agcttggcgt aatcatggtc atagctgttt cctgtgtgaa attgttatcc gctcacaatt   2220
ccacacaaca tacgagccgg aagcataaag tgtaaagcct ggggtgccta atgagtgagc   2280
taactcacat taattgcgtt gcgctcactg cccgctttcc agtcgggaaa cctgtcgtgc   2340
cagctgcatt aatgaatcgg ccaacgcgcg gggagaggcg gtttgcgtat tgggcgctct   2400
tccgcttcct cgctcactga ctcgctgcgc tcggtcgttc ggctgcggcg agcggtatca   2460
gctcactcaa aggcggtaat acggttatcc acagaatcag gggataacgc aggaaagaac   2520
atgtgagcaa aaggccagca aaaggccagg aaccgtaaaa aggccgcgtt gctggcgttt   2580
ttccataggc tccgcccccc tgacgagcat cacaaaaatc gacgctcaag tcagaggtgg   2640
cgaaacccga caggactata aagataccag gcgtttcccc ctggaagctc cctcgtgcgc   2700
tctcctgttc cgaccctgcc gcttaccgga tacctgtccg cctttctccc ttcgggaagc   2760
gtggcgcttt ctcatagctc acgctgtagg tatctcagtt cggtgtaggt cgttcgctcc   2820
aagctgggct gtgtgcacga accccccgtt cagcccgacc gctgcgcctt atccggtaac   2880
tatcgtcttg agtccaaccc ggtaagacac gacttatcgc cactggcagc agccactggt   2940
aacaggatta gcagagcgag gtatgtaggc ggtgctacag agttcttgaa gtggtggcct   3000
aactacggct acactagaag gacagtattt ggtatctgcg ctctgctgaa gccagttacc   3060
ttcggaaaaa gagttggtag ctcttgatcc ggcaaacaaa ccaccgctgg tagcggtggt   3120
ttttttgttt gcaagcagca gattacgcgc agaaaaaaag gatctcaaga agatcctttg   3180
atcttttcta cggggtctga cgctcagtgg aacgaaaact cacgttaagg gattttggtc   3240
atgagattat caaaaaggat cttcacctag atccttttaa attaaaaatg aagttttaaa   3300
tcaatctaaa gtatatatga gtaaacttgg tctgacagtt accaatgctt aatcagtgag   3360
gcacctatct cagcgatctg tctatttcgt tcatccatag ttgcctgact ccccgtcgtg   3420
tagataacta cgatacggga gggcttacca tctggcccca gtgctgcaat gataccgcga   3480
gacccacgct caccggctcc agatttatca gcaataaacc agccagccgg aagggccgag   3540
cgcagaagtg gtcctgcaac tttatccgcc tccatccagt ctattaattg ttgccgggaa   3600
gctagagtaa gtagttcgcc agttaatagt ttgcgcaacg ttgttgccat tgctacaggc   3660
atcgtggtgt cacgctcgtc gtttggtatg gcttcattca gctccggttc ccaacgatca   3720
aggcgagtta catgatcccc catgttgtgc aaaaaagcgg ttagctcctt cggtcctccg   3780
atcgttgtca gaagtaagtt ggccgcagtg ttatcactca tggttatggc agcactgcat   3840
aattctctta ctgtcatgcc atccgtaaga tgcttttctg tgactggtga gtactcaacc   3900
aagtcattct gagaatagtg tatgcggcga ccgagttgct cttgcccggc gtcaatacgg   3960
```

-continued gataataccg cgccacatag cagaacttta aaagtgctca tcattggaaa acgttcttcg 4020
gggcgaaaac tctcaaggat cttaccgctg ttgagatcca gttcgatgta acccactcgt 4080
gcacccaact gatcttcagc atcttttact ttcaccagcg tttctgggtg agcaaaaaca 4140
ggaaggcaaa atgccgcaaa aaagggaata agggcgacac ggaaatgttg aatactcata 4200
ctcttccttt ttcaatatta ttgaagcatt tatcagggtt attgtctcat gagcggatac 4260
atatttgaat gtatttagaa aaataaacaa ataggggttc cgcgcacatt tccccgaaaa 4320
gtgccacctg acgtctaaga aaccattatt atcatgacat taacctataa aaataggcgt 4380
atcacgaggc cctttcgtc 4399

<210> SEQ ID NO 28
<211> LENGTH: 32
<212> TYPE: DNA
<213> ORGANISM: Primer

<400> SEQUENCE: 28
ggagttgttc aatcatggtc gtgatgtgtg ta 32

<210> SEQ ID NO 29
<211> LENGTH: 32
<212> TYPE: DNA
<213> ORGANISM: Primer

<400> SEQUENCE: 29
tacacacatc acgaccatga ttgaacaact cc 32

<210> SEQ ID NO 30
<211> LENGTH: 34
<212> TYPE: DNA
<213> ORGANISM: Primer

<400> SEQUENCE: 30
ccttaattaa ggcagacaac aacttggcaa agtc 34

<210> SEQ ID NO 31
<211> LENGTH: 2724
<212> TYPE: DNA
<213> ORGANISM: Candida tropicalis

<400> SEQUENCE: 31
atgcacgaag cggagataaa agattacgta atttatctcc tgagacaatt ttagccgtgt 60
tcacacgccc ttctttgttc tgagcgaagg ataaataatt agacttccac agctcattct 120
aatttccgtc acgcgaatat tgaagggggg tacatgtggc cgctgaatgt gggggcagta 180
aacgcagtct ctcctctccc aggaatagtg caacggagga aggataacgg atagaaagcg 240
gaatgcgagg aaaattttga acgcgcaaga aaagcaatat ccgggctacc aggttttgag 300
ccagggaaca cactcctatt tctgctcaat gactgaacat agaaaaaaca ccaagacgca 360
atgaaacgca catggacatt tagacctccc cacatgtgat agtttgtctt aacagaaaag 420
tataataaga acccatgccg tcccttttct ttcgccgctt caactttttt ttttttatct 480
tacacacatc acgaccatga ttgaacaact cctagaatat tggtatgtcg ttgtgccagt 540
gttgtacatc atcaaacaac tccttgcata cacaaagact cgcgtcttga tgaaaaagtt 600
gggtgctgct ccagtcacaa acaagttgta cgacaacgct ttcggtatcg tcaatggatg 660
gaaggctctc cagttcaaga aagagggcag ggctcaagag tacaacgatt acaagtttga 720
ccactccaag aacccaagcg tgggcaccta cgtcagtatt cttttcggca ccaggatcgt 780

-continued

```
cgtgaccaaa gatccagaga atatcaaagc tattttggca acccagtttg gtgatttttc    840

tttgggcaag aggcacactc tttttaagcc tttgttaggt gatgggatct tcacattgga    900

cggcgaaggc tggaagcaca gcagagccat gttgagacca cagtttgcca gagaacaagt    960

tgctcatgtg acgtcgttgg aaccacactt ccagttgttg aagaagcata ttcttaagca   1020

caagggtgaa tactttgata tccaggaatt gttctttaga tttaccgttg attcggccac   1080

ggagttctta tttggtgagt ccgtgcactc cttaaaggac gaatctattg gtatcaacca   1140

agacgatata gattttgctg gtagaaagga ctttgctgag tcgttcaaca aagcccagga   1200

atacttggct attagaacct tggtgcagac gttctactgg ttggtcaaca acaaggagtt   1260

tagagactgt accaagctgg tgcacaagtt caccaactac tatgttcaga aagctttgga   1320

tgctagccca gaagagcttg aaaagcaaag tgggtatgtg ttcttgtacg agcttgtcaa   1380

gcagacaaga gaccccaatg tgttgcgtga ccagtctttg aacatcttgt tggccggaag   1440

agacaccact gctgggttgt tgtcgtttgc tgtctttgag ttggccagac acccagagat   1500

ctgggccaag ttgagagagg aaattgaaca acagtttggt cttggagaag actctcgtgt   1560

tgaagagatt acctttgaga gcttgaagag atgtgagtac ttgaaagcgt tccttaatga   1620

aaccttgcgt atttacccaa gtgtcccaag aaacttcaga atcgccacca agaacacgac   1680

attgccaagg ggcggtggtt cagacggtac ctcgccaatc ttgatccaaa agggagaagc   1740

tgtgtcgtat ggtatcaact ctactcattt ggaccctgtc tattacggcc ctgatgctgc   1800

tgagttcaga ccagagagat ggtttgagcc atcaaccaaa aagctcggct gggcttactt   1860

gccattcaac ggtggtccaa gaatctgttt gggtcagcag tttgccttga cggaagctgg   1920

ctatgtgttg gttagattgg tgcaagagtt ctcccacgtt aggctggacc cagacgaggt   1980

gtacccgcca aagaggttga ccaacttgac catgtgtttg caggatggtg ctattgtcaa   2040

gtttgactag cggcgtggtg aatgcgtttg attttgtagt ttctgtttgc agtaatgaga   2100

taactattca gataaggcga gtggatgtac gttttgtaag agtttcctta caaccttggt   2160

ggggtgtgtg aggttgaggt tgcatcttgg ggagattaca ccttttgcag ctctccgtat   2220

acacttgtac tctttgtaac ctctatcaat catgtggggg gggggttca ttgtttggcc    2280

atggtggtgc atgttaaatc cgccaactac ccaatctcac atgaaactca agcacactaa   2340

aaaaaaaaaa gatgttgggg gaaaactttg gtttcccttc ttagtaatta aacactctca   2400

ctctcactct cactctctcc actcagacaa accaaccacc tgggctgcag acaaccagaa   2460

aaaaaaagaa caaaatccag atagaaaaac aaagggctgg acaaccataa ataaacaatc   2520

tagggtctac tccatcttcc actgtttctt cttcttcaga cttagctaac aaacaactca   2580

cttcaccatg gattacgcag gcatcacgcg tggctccatc agaggcgagg ccttgaagaa   2640

actcgcagaa ttgaccatcc agaaccagcc atccagcttg aaagaaatca acaccggcat   2700

ccagaaggac gactttgcca agtt                                           2724

<210> SEQ ID NO 32
<211> LENGTH: 517
<212> TYPE: PRT
<213> ORGANISM: Candida tropicalis

<400> SEQUENCE: 32

Met Ile Glu Gln Leu Leu Glu Tyr Trp Tyr Val Val Val Pro Val Leu
1               5                   10                  15

Tyr Ile Ile Lys Gln Leu Leu Ala Tyr Thr Lys Thr Arg Val Leu Met
```

-continued

```
            20                  25                  30

Lys Lys Leu Gly Ala Ala Pro Val Thr Asn Lys Leu Tyr Asp Asn Ala
        35                  40                  45

Phe Gly Ile Val Asn Gly Trp Lys Ala Leu Gln Phe Lys Lys Glu Gly
    50                  55                  60

Arg Ala Gln Glu Tyr Asn Asp Tyr Lys Phe Asp His Ser Lys Asn Pro
65                  70                  75                  80

Ser Val Gly Thr Tyr Val Ser Ile Leu Phe Gly Thr Arg Ile Val Val
                85                  90                  95

Thr Lys Asp Pro Glu Asn Ile Lys Ala Ile Leu Ala Thr Gln Phe Gly
            100                 105                 110

Asp Phe Ser Leu Gly Lys Arg His Thr Leu Phe Lys Pro Leu Leu Gly
        115                 120                 125

Asp Gly Ile Phe Thr Leu Asp Gly Glu Gly Trp Lys His Ser Arg Ala
    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
                165                 170                 175

Gly Glu Tyr Phe Asp Ile Gln Glu Leu Phe Phe Arg Phe Thr Val Asp
            180                 185                 190

Ser Ala Thr Glu Phe Leu Phe Gly Glu Ser Val His Ser Leu Lys Asp
        195                 200                 205

Glu Ser Ile Gly Ile Asn Gln Asp Asp Ile Asp Phe Ala Gly Arg Lys
    210                 215                 220

Asp Phe Ala Glu Ser Phe Asn Lys Ala Gln Glu Tyr Leu Ala Ile Arg
225                 230                 235                 240

Thr Leu Val Gln Thr Phe Tyr Trp Leu Val Asn Asn Lys Glu Phe Arg
                245                 250                 255

Asp Cys Thr Lys Leu Val His Lys Phe Thr Asn Tyr Tyr Val Gln Lys
            260                 265                 270

Ala Leu Asp Ala Ser Pro Glu Glu Leu Glu Lys Gln Ser Gly Tyr Val
        275                 280                 285

Phe Leu Tyr Glu Leu Val Lys Gln Thr Arg Asp Pro Asn Val Leu Arg
    290                 295                 300

Asp Gln Ser Leu Asn Ile Leu Leu Ala Gly Arg Asp Thr Thr Ala Gly
305                 310                 315                 320

Leu Leu Ser Phe Ala Val Phe Glu Leu Ala Arg His Pro Glu Ile Trp
                325                 330                 335

Ala Lys Leu Arg Glu Glu Ile Glu Gln Gln Phe Gly Leu Gly Glu Asp
            340                 345                 350

Ser Arg Val Glu Glu Ile Thr Phe Glu Ser Leu Lys Arg Cys Glu Tyr
        355                 360                 365

Leu Lys Ala Phe Leu Asn Glu Thr Leu Arg Ile Tyr Pro Ser Val Pro
    370                 375                 380

Arg Asn Phe Arg Ile Ala Thr Lys Asn Thr Thr Leu Pro Arg Gly Gly
385                 390                 395                 400

Gly Ser Asp Gly Thr Ser Pro Ile Leu Ile Gln Lys Gly Glu Ala Val
                405                 410                 415

Ser Tyr Gly Ile Asn Ser Thr His Leu Asp Pro Val Tyr Tyr Gly Pro
            420                 425                 430

Asp Ala Ala Glu Phe Arg Pro Glu Arg Trp Phe Glu Pro Ser Thr Lys
        435                 440                 445
```

-continued

```
Lys Leu Gly Trp Ala Tyr Leu Pro Phe Asn Gly Gly Pro Arg Ile Cys
    450                 455                 460

Leu Gly Gln Gln Phe Ala Leu Thr Glu Ala Gly Tyr Val Leu Val Arg
465                 470                 475                 480

Leu Val Gln Glu Phe Ser His Val Arg Leu Asp Pro Asp Glu Val Tyr
                485                 490                 495

Pro Pro Lys Arg Leu Thr Asn Leu Thr Met Cys Leu Gln Asp Gly Ala
            500                 505                 510

Ile Val Lys Phe Asp
        515


<210> SEQ ID NO 33
<211> LENGTH: 222
<212> TYPE: DNA
<213> ORGANISM: vector

<400> SEQUENCE: 33

caggaaacag ctatgaccat gattacgcca agcttggtac cgagctcgga tccactagta      60

acggccgcca gtgtgctgga attcgccctt aagggcgaat tctgcagata tccatcacac     120

tggcggccgc tcgagcatgc atctagaggg cccaattcgc cctatagtga gtcgtattac     180

aattcactgg ccgtcgtttt acaacgtcgt gactgggaaa ac                        222


<210> SEQ ID NO 34
<211> LENGTH: 222
<212> TYPE: DNA
<213> ORGANISM: vector

<400> SEQUENCE: 34

gtcctttgtc gatactggta ctaatgcggt tcgaaccatg gctcgagcct aggtgatcat      60

tgccggcggt cacacgacct taagccggaa ttcccgctta agacgtctat aggtagtgtg     120

accgccggcg agctcgtacg tagatctccc gggttaagcg ggatatcact cagcataatg     180

ttaagtgacc ggcagcaaaa tgttgcagca ctgacccttt tg                        222
```

METHOD OF INCREASING CONVERSION OF A FATTY ACID TO ITS CORRESPONDING DICARBOXYLIC ACID

CROSS REFERENCE TO RELATED APPLICATIONS

This application is a divisional application of U.S. Ser. No. 09/911,781, filed Jul. 24, 2001, now U.S. Pat. No. 6,673,613. U.S. Ser. No. 09/911,781 claims priority to U.S. Provisional Application Ser. No. 60/220,850 filed Jul. 26, 2000, the contents of which are hereby incorporated by reference.

STATEMENT REGARDING FEDERALLY SPONSORED RESEARCH OR DEVELOPMENT

This invention was funded, at least in part, under grants from the Department of Commerce, NIST-ATP Cooperative Agreement Number 70NANB8H4033 and the Department of Energy No. DE-FC36-95GO10099. The Government may therefore have certain rights in the invention.

BACKGROUND OF THE INVENTION

1. Field of the Invention

This invention relates to processes and compositions for improving dicarboxylic acid production in yeast by replacing the native promoter of a target gene with a heterologous promoter from a yeast gene having a desired level of activity.

2. Description of Related Art

Aliphatic dioic acids are versatile chemical intermediates useful as raw materials for the preparation of perfumes, polymers, adhesives and macrolid antibiotics. While several chemical routes to the synthesis of long-chain α, ω-dicarboxylic acids are available, the synthesis is not easy and most methods result in mixtures containing shorter chain lengths. As a result, extensive purification steps are necessary. While it is known that long-chain dioic acids can also be produced by microbial transformation of alkanes, fatty acids or esters thereof, chemical synthesis has remained the most commercially viable route, due to limitations with the current biological approaches.

Several strains of yeast are known to excrete α, ω-dicarboxylic acids as a byproduct when cultured on alkanes or fatty acids as the carbon source. In particular, yeast belonging to the Genus Candida, such as *C. albicans, C. cloacae, C. guillermondii, C. intermedia, C. lpolytica, C. maltosa, C. parapsilosis* and *C. zeylenoides* are known to produce such dicarboxylic acids (*Agr. Biol. Chem.* 35: 2033–2042 (1971)). Also, various strains of *C. tropicalis* are known to produce dicarboxylic acids ranging in chain lengths from $C_{11}$ through $C_{18}$ (Okino et al., B M Lawrence, B D Mookherjee and B J Willis (eds), in *Flavors and Fragrances: A World Perspective*. Proceedings of the $10^{th}$ International Conference of Essential Oils, Flavors and Fragrances, Elsevier Science Publishers BV Amsterdam (1988)), and are the basis of several patents as reviewed by Bühler and Schindler, in *Aliphatic Hydrocarbons in Biotechnology*, H. J. Rehm and G. Reed (eds), Vol. 169, Verlag Chemie, Weinheim (1984).

Studies of the biochemical processes by which yeasts metabolize alkanes and fatty acids have revealed three types of oxidation reactions: α-oxidation of alkanes to alcohols, ω-oxidation of fatty acids to α, ω-dicarboxylic acids and the degradative β-oxidation of fatty acids to $CO_2$ and water. The first two types of oxidations are catalyzed by microsomal enzymes while the last type takes place in the peroxisomes. In *C. tropicalis*, the first step in the ω-oxidation pathway is catalyzed by a membrane-bound enzyme complex (ω-hydroxylase complex) including a cytochrome P450 monooxygenase and a NADPH cytochrome reductase. This hydroxylase complex is responsible for the primary oxidation of the terminal methyl group in alkanes and fatty acids as described, e.g., in Gilewicz et al., *Can. J. Microbiol.* 25:201 (1979), incorporated herein by reference. The genes which encode the cytochrome P450 and NADPH reductase components of the complex have previously been identified as P450ALK and P450RED respectively, and have also been cloned and sequenced as described, e.g., in Sanglard et al., *Gene* 76:121–136 (1989), incorporated herein by reference. P450ALK has also been designated P450ALK1. More recently, ALK genes have been designated by the symbol CYP and RED genes have been designated by the symbol CPR. See, e.g., Nelson, *Pharmacogenetics* 6(1):1–42 (1996), which is incorporated herein by reference. See also Ohkuma et al., *DNA and Cell Biology* 14:163–173 (1995), Seghezzi et al., *DNA and Cell Biology*, 11:767–780 (1992) and Kargel et al., *Yeast* 12:333–348 (1996), each incorporated herein by reference. In addition, CPR genes are now also referred to as NCP genes. See, e.g., De Backer et al., *Antimicrobial Agents* and *Chemotherapy*, 45:1660 (2001). For example, P450ALK is also designated CYP52 according to the nomenclature of Nelson, supra. Fatty acids are ultimately formed from alkanes after two additional oxidation steps, catalyzed by alcohol oxidase as described, e.g., in Kemp et al., *Appl. Microbiol. and Biotechnol.* 28: 370–374 (1988), incorporated herein by reference, and aldehyde dehydrogenase. The fatty acids can be further oxidized through the same or similar pathway to the corresponding dicarboxylic acid. The ω-oxidation of fatty acids proceeds via the ω-hydroxy fatty acid and its aldehyde derivative, to the corresponding dicarboxylic acid without the requirement for CoA activation. However, both fatty acids and dicarboxylic acids can be degraded, after activation to the corresponding acyl-CoA ester through the β-oxidation pathway in the peroxisomes, leading to chain shortening. In mammalian systems, both fatty acid and dicarboxylic acid products of ω-oxidation are activated to their CoA-esters at equal rates and are substrates for both mitochondrial and peroxisomal β-oxidation (*J. Biochem.*, 102:225–234 (1987)). In yeast, β-oxidation takes place solely in the peroxisomes (*Agr. Biol. Chem.* 49:1821–1828 (1985)).

Cytochrome P450 monooxygenases (P450s) are terminal monooxidases of a multicomponent enzyme system including P450 and CPR (NCP). In some instances, a second electron carrier, cytochrome b5(CYTb5) and its associated reductase are involved as described below and in Morgan, et al., *Drug Metab. Disp.* 12:358–364 (1984). The P450s comprise a superfamily of proteins which exist widely in nature having been isolated from a variety of organisms as described e.g., in Nelson, supra. These organisms include various mammals, fish, invertebrates, plants, mollusk, crustaceans, lower eukaryotes and bacteria (Nelson, supra). First discovered in rodent liver microsomes as a carbon-monoxide binding pigment as described, e.g., in Garfinkel, *Arch. Biochem. Biophys.* 77:493–509 (1958), which is incorporated herein by reference, P450s were later named based on their absorption at 450 nm in a reduced-CO coupled difference spectrum as described, e.g., in Omura et al., *J. Biol. Chem.* 239:2370–2378 (1964), which is incorporated herein by reference.

Monooxygenation reactions catalyzed by cytochromes P450 in a eukaryotic membrane-bound system require the transfer of electrons from NADPH to P450 via NADPH-cytochrome P450 reductase (CPR) as described, e.g., in Taniguchi et al., *Arch. Biochem. Biophys.* 232:585 (1984), incorporated herein by reference. CPR is a flavoprotein of approximately 78,000 Da containing 1 mol of flavin adenine dinucleotide (FAD) and 1 mol of flavin mononucleotide (FMN) per mole of enzyme as described, e.g., in Potter et al., *J. Biol. Chem.* 258:6906 (1983), incorporated herein by reference. The FAD moiety of CPR is the site of electron entry into the enzyme, whereas FMN is the electron-donating site to P450 as described, e.g., in Vermilion et al., *J. Biol. Chem.* 253:8812 (1978), incorporated herein by reference. The overall reaction is as follows:

$$H^{+}+RH+NADPH+O_2 \rightarrow ROH+NADP^{+}+H_2O$$

Binding of a substrate to the catalytic site of P450 apparently results in a conformational change initiating electron transfer from CPR to P450. Subsequent to the transfer of the first electron, $O_2$ binds to the $Fe_2^{+}$-P450 substrate complex to form $Fe_3^{+}$-P450-substrate complex. This complex is then reduced by a second electron from CPR, or, in some cases, NADH via a second electron carrier, cytochrome b5 (CYTb5) and its associated NADH-cytochrome b5 reductase as described, e.g., in Guengerich et al., *Arch. Biochem. Biophys.* 205:365 (1980), incorporated herein by reference, and Morgan, supra. Most of the aforementioned studies implicate CYTb5 as being involved in the pathway only for the transfer of the second electron. One atom of this reactive oxygen is introduced into the substrate, while the other is reduced to water. The oxygenated substrate then dissociates, regenerating the oxidized form of the cytochrome P450 as described, e.g., in Klassen, Amdur and Doull, *Casarett and Doull's Toxicology*, Macmillan, N.Y. (1986), incorporated herein by reference. With respect to the CYTb5, several other models of the role of this protein in P450 expression have been proposed besides its role as an electron carrier.

While several chemical routes to the synthesis of long-chain α, ω-dicarboxylic acids as 9-octadecenedioic acid are available, such methods are complex and usually result in mixtures containing shorter chain lengths. As a result, extensive purification steps are necessary. As an alternative to chemical syntheses, long chain α,ω-dicarboxylic acids such as 9-octadecenedioic acid can be made via fermentation methods such as microbial transformation of the corresponding hydrocarbons such as alkanes or alkenes, fatty acids or esters thereof. One method for producing substantially pure α,ω-dicarboxylic acids in substantially quantitative yield is described in U.S. Pat. No. 5,254,466, the entire contents of which are incorporated herein by reference. This method comprises culturing a *C. tropicalis* strain wherein both copies of the chromosomal POX5 and each of the POX4A and POX4B genes are disrupted in a culture medium containing a nitrogen source, an organic substrate and a cosubstrate.

The POX4 and POX5 gene disruptions effectively block the β-oxidation pathway at its first reaction (which is catalyzed by acyl-CoA oxidase) in a *C. tropicalis* host strain. The POX4A and POX5 genes encode distinct subunits of long chain acyl-CoA oxidase, which are the peroxisomal polypeptides (PXPs) designated PXP-4 and PXP-5, respectively. The disruption of one or more of these genes results in a partial or complete inactivation of the β-oxidation pathway thus allowing enhanced yields of dicarboxylic acid by redirecting the substrate toward the α-oxidation pathway and also prevents reutilization of the dicarboxylic acid products through the β-oxidation pathway.

Another method for producing substantially pure α,ω-dicarboxylic acids in substantial yield is described in U.S. application Ser. No. 09/302,620, now U.S. Pat. No. 6,331,420, and international Application No.PCT/US99/20797, the entire contents of each being incorporated herein by reference. This method includes increasing the CYP and CPR (NCP) enzymes by amplification of the CYP and CPR gene copy number in *C. tropicalis* strain, and culturing the genetically modified strain in media containing an organic substrate.

Gene(s) involved in the bioconversion of various feed stocks, e.g., HOSFFA (high oleic sunflower oil, i.e., fatty acid mixtures containing oleic acid commercially available from Cognis Corp. as Edenor® and Emersol®), have native promoters that control their transcriptional regulation. These promoters are sometimes inadequate to achieve the level of transcription needed to make a gene(s) product, e.g., CPR or CYTb5, that is involved in a given process.

Accordingly, there exists a need for improved processes for increasing dicarboxylic acid production in yeast.

SUMMARY OF THE INVENTION

In one aspect, the present invention involves improved processes and compositions for increasing dicarboxylic acid production in a microorganism such as yeast. In one embodiment, dicarboxylic acid production is increased by isolating a weak promoter of a gene involved in dicarboxylic acid production and replacing the weak promoter with a strong promoter from a yeast gene having a high level of expression. The substitution of a strong promoter operably linked to a target gene involved in dicarboxylic acid production increases the level of transcription of that target gene.

In another aspect, a nucleic acid sequence is provided which includes a CYP52A2A gene promoter operably linked to the open reading frame of a gene encoding a heterologous protein. Such nucleic acid sequence may be utilized to transform a host cell, to obtain increased expression of a target protein.

In another aspect, expression vectors are provided which include any one of the aforementioned nucleic acid constructs. In yet another aspect, a host cell transformed with one of the aforementioned expression vectors is provided.

In another aspect, a process for transforming a host cell is provided which includes isolating a CYP52A2A promoter; isolating a target gene; operably linking CYP52A2A promoter to the open reading frame target gene to create a fusion gene; inserting the fusion gene into an expression vector; and transforming the host cell with the expression vector.

DESCRIPTION OF THE DRAWINGS

FIGS. 1A–1B depict the nucleotide sequence of the CYP52A2A gene of *C. tropicalis* 20336 (SEQ ID NO:1).

FIGS. 2A–2B depict the nucleotide sequence of the CPRA gene of *C. tropicalis* 20336 (SEQ ID NO:2).

FIGS. 3A–3B depict the nucleotide sequence of the CPRB gene of *C. tropicalis* 20336 (SEQ ID NO:3).

FIGS. 4A–4C depict the nucleotide sequence along with amino acid sequences corresponding to certain delineated nucleic acid sequences of the CYTb5 gene of *C. tropicalis* 20336 (SEQ ID NOS:4 and 5).

FIGS. 5A–5D depict the nucleotide sequence along with amino acid sequences corresponding to certain delineated nucleic acid sequences of the CYP52A2A/CPRB fusion gene (SEQ ID NO:10).

FIG. 8 depicts the nucleotide sequence (SEQ ID NO:23) along with the amino acid sequences (SEQ ID NO:24) corresponding to certain delineated nucleic acid sequences of the URA3A gene.

FIG. 11 depicts the nucleotide sequence of the CYP52A2A gene promoter/CYP52A5A ORF fusion gene (SEQ ID NO:31).

DETAILED DESCRIPTION OF THE INVENTION

Figure 6A:
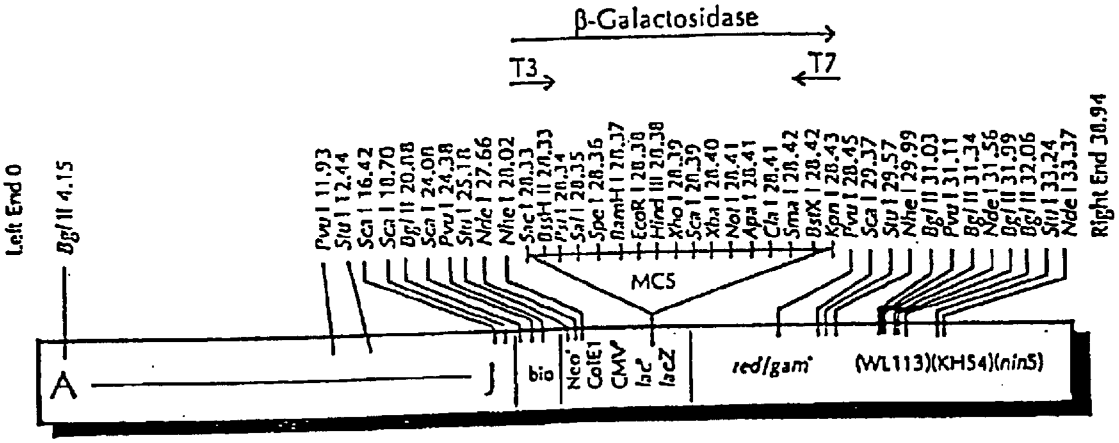
FIG. 6A is a schematic depiction of the λ ZAP Express™ vector.

Increasing dicarboxylic acid production in yeast in accordance with the present invention is based on isolating a promoter from a yeast gene having a desired level of expression and operably linking the promoter to a target gene involved in dicarboxylic acid production. Accordingly, promoter substitution using highly inducible heterologous promoters operably linked to the open reading frame (ORF) of a target gene involved in dicarboxylic acid production in yeast increases the yield of dicarboxylic acids as a result of increased transcription. Furthermore, promoters of gene(s) that are induced at various defined times during the bioconversion in response to certain stimuli (e.g., stress, substrate, cell death) may be utilized for promoter substitution of the target gene(s) thereby leading to increased dicarboxylic acid production at defined times during the bioprocess.

The CYP52A2A gene of *C. tropicalis* 20336 (SEQ ID NO.1) (See FIG. 1), as described in aforementioned U.S. application Ser. No. 09/302,620, now U.S. Pat. No. 6,331,420, and International Application No. PCT/US99/20797 is one gene from a family of genes involved in the metabolism of oleic acid to produce oleic dicarboxylic acid. The level of transcriptional induction of this gene in an oleic acid fermentation is many fold (>25) above other members of the same gene family. CPR genes (also referred to herein as NCP genes), e.g., CPRA (SEQ ID NO.2) and CPRB (SEQ. ID. NO.3) of *C. tropicalis* 20336 (cytochrome P450 reductase, FIGS. 2 and 3, respectively) are other genes involved in the process of producing dicarboxylic acid. However, the level of transcriptional induction of such CPR genes in a corresponding fermentation is only three-fold above background which defines a rate limiting factor in the production of dicarboxylic acids.

Any gene involved in fatty acid bioconversion which transcribes at a rate lower than CYP52A2A may be upregulated by the substitution of its native promoter with the CYP52A2A promoter. In a preferred embodiment, the promoter of the CPR gene is substituted with the promoter of the CYP52A2A or other CYP gene(s), thereby increasing the transcriptional induction of the CPR gene. As an example, the CYP promoter is derived from the CYP52A2A gene of *C. tropicalis* 20336. The complete promoter of the CYP gene or a portion thereof containing all of the essential functional sites for the promoter region is operably linked to the open reading frame of a CPR gene, such as the CPRB gene from *C. tropicalis* 20336. This in turn results in the increased transcription and production of the CPR protein and a corresponding increase in the conversion of a fatty acid, e.g., oleic acid, to its corresponding dicarboxylic acid. The term "operably linked" refers to the association of nucleic acid sequences so that the function of one is affected by the other. A promoter is operably linked with an open reading frame when it is capable of affecting the expression of the open reading frame (ORF) (i.e., the ORF is under the transcriptional control of the promoter). Notwithstanding the presence of other sequences between the promoter and ORF, it should be understood that a promoter may still be considered operably linked to the ORF. In another preferred embodiment the promoter of the CYTb5 gene is replaced by the promoter of the CYP52A2A or other CYP gene(s) in essentially the same manner described herein, resulting in increased production of the CYTb5 protein and an increase in the conversion of fatty acids to their corresponding dicarboxylic acids.

In one embodiment of the present invention, the desired promoter region is isolated using conventional techniques known to those skilled in the art. The CYP gene is cut at a convenient location downstream of the promoter terminus using an appropriate restriction enzyme to effect scission. The structural CYP gene region is then removed, to leave essentially a DNA sequence containing the promoter region. For the upstream cutting, a site is selected sufficiently far upstream to include in the retained portion all of the necessary functional sites for the promoter region, and then cut using an appropriate restriction enzyme. It should be understood that in all embodiments described herein the promoter may be included on a nucleic acid fragment that is larger than the actual promoter region and that the entire fragment, including additional nucleic acid sequence can be utilized for fusion to a target gene.

Next, a promoter/target gene open reading frame nucleotide fusion construct is prepared. The promoter is operably linked to a heterologous target gene, i.e., to the open reading frame of a gene other than the CYP52A2A gene to create a nucleotide fusion construct for integration into a host cell. Procedures for fusing promoters to target genes such that they are operably linked and yield the desired DNA construct are well known in the art. Restriction enzymes, ligating enzymes and polymerases are conventional tools commonly utilized by those skilled in the art to create fusion constructs. In a preferred embodiment, polymerase chain reaction (PCR) primers are constructed to amplify the promoter of the CYP52A2A gene using PCR. The correct sequence is verified by conventional techniques known to those skilled in the art. The open reading frame (ORF) and 3' untranslated region (UTR) of the target gene, e.g., CPR or CYTb5, are also amplified by PCR and verified by sequencing. These two sequences are then fused together by PCR using the two PCR products and the original primers of the initial PCRs that are not homologous at the fusion junction. The product contains the CYP52A2A promoter, the target gene ORF and 3' UTR and is confirmed by sequence analysis.

The promoter/target gene ORF fusion constructs are then utilized to create a DNA integration vector for transformation into any suitable host cells. For example, suitable yeast host cells for use in accordance with the present invention include, but are not limited to, Yarrowia, Bebaromyces, Saccharomyces, Schizosaccharomyces, and Pichia and more preferably those of the Candida genus. Preferred species of Candida are *tropicalis, maltosa, apicola, paratropicalis, albicans, cloacae, guillermondii, intermedia, lipolytica, parapsilosis* and *zeylenoides.*

Particularly preferred hosts include *C. tropicalis* strains that have been genetically modified so that one or more of the chromosomal POX4A, POX4B and both POX5 genes have been disrupted as described, e.g., in U.S. Pat. Nos. 5,254,466 and 5,620,878, each incorporated herein by reference. Such disruption blocks the β-oxidation pathway. Examples of β-oxidation blocked strains of *C. tropicalis* include H41, H41B, H51, H45, H43, H53, H534, H534B, H435 and H5343 (ATCC 20962) as described in aforementioned U.S. Pat. No. 5,254,466.

The DNA constructs described herein may be cloned and expressed in suitable expression vectors. Examples include, but are not limited to vectors such as plasmids, phagemids, phages or cosmids, yeast episomal plasmids, yeast artificial chromosomes, and yeast replicative plasmids. Host cells may also be transformed by introducing into a cell a linear DNA vector(s) containing the desired gene sequence. Such linear DNA may be advantageous when it is desirable to avoid introduction of non-native (foreign) DNA into the cell. For example, DNA consisting of a desired target gene(s) flanked by DNA sequences which are native to the cell can be introduced into the cell by methods such as, but not limited to electroporation, lithium acetate transformation, and spheroplasting. Flanking DNA sequences can include selectable markers and/or other tools for genetic engineering. Yeast cells may be transformed with any of the expression vectors described herein. The term "expression vector" is used broadly herein and is intended to encompass any medium which includes nucleic acid and which can be used to transform a target cell. Expression vector thus encompasses all the examples of vectors listed herein including, e.g., integration vectors.

In a preferred embodiment the DNA construct is used to transform a yeast cell, e.g., a Candida sp., to obtain increased expression therein of a protein, e.g., a CPR protein, the DNA construct comprising an inducible CYP promoter DNA for promoter transcription in yeast operably linked to DNA coding for the CPR protein to enable expression thereof in the yeast cell, the CYP promoter DNA being foreign or heterologous to the DNA coding for the protein. Once created, a yeast host cell containing the CYP52A2A promoter/target gene ORF chimera is generated.

In another preferred embodiment, the DNA fusion construct is used to transform a yeast cell, e.g., a Candida sp., to obtain increased expression therein of a CYTb5 protein, the DNA construct comprising an inducible CYP promoter DNA for promoter transcription in yeast operably linked to DNA coding for the CYTb5 protein to enable expression thereof in the yeast cell, the CYP promoter DNA being foreign or heterologous to the DNA coding for the CYTb5 protein. As an example, the complete CYP52A2A promoter or a portion thereof derived from the CYP52A2A gene of *C. tropicalis* 20336 containing all of the essential functional sites for the promoter region is fused to the open reading frame of a CYTb5 gene such as the CYTb5 gene from *C. tropicalis* 20336 (FIG. 4 depicts the nucleic acid sequence (SEQ. ID. NO. 4) and amino acid sequence (SEQ. ID. NO. 5) corresponding to certain delineated nucleic acid sequences).

The strength of the promoter may be measured using techniques well known to those skilled in the art. In a preferred embodiment, promoter strength may be measured using quantitative competitive reverse transcription polymerase chain reaction (QC-RT-PCR) to measure CPR and CYTb5 gene expression in yeast e.g., Candida cells isolated from fermentors. Enzymatic assays and antibodies specific for both CPR and CYTb5 proteins may be used when appropriate to verify that increased promoter strength is reflected by increased synthesis of the corresponding protein. Diacid productivity is thus improved by selective integration, amplification, and over expression of CPR and CYTb5 genes in a yeast production host, e.g., *C. tropicalis, C. maltosa*, Pichia, etc.

The yeast cells transformed with one of the aforementioned vectors, may be cultured in media containing an organic substrate, to provide improved production of dicarboxylic acid(s). Culturing the yeast, i.e., fermenting the yeast, may be accomplished by procedures well known in the art as described, e.g., in aforesaid U.S. Pat. No. 5,254,466.

A suitable organic substrate herein may be any organic compound that is biooxidizable to a mono- or polycarboxylic acid. Such a compound may be any saturated or unsaturated aliphatic compound or any carboxylic or heterocyclic aromatic compound having at least one terminal methyl group, a terminal carboxyl group and/or a terminal functional group which is oxidizable to a carboxyl group by biooxidation. A terminal functional group which is a derivative of a carboxyl group may be present in the substrate molecule and may be converted to a carboxyl group by a reaction other than biooxidation. For example, if the terminal group is an ester that neither the wild-type *C. tropicalis* nor the genetic modifications described herein will allow hydrolysis of the ester functionality to a carboxyl group, then a lipase can be added during the fermentation step to liberate free fatty acids. Suitable organic substrates include, but are not limited to, saturated fatty acids, unsaturated fatty acids, alkanes, alkenes, alkynes and combinations thereof.

Alkanes are a type of saturated organic substrate which are particularly useful herein. The alkanes can be linear or cyclic, branched or straight chain, substituted or unsubstituted. Particularly preferred alkanes are those having from about 4 to about 25 carbon atoms, examples of which include, but are not limited to, butane, hexane, octane, nonane, dodecane, tridecane, tetradecane, hexadecane, octadecane and the like.

Examples of unsaturated organic substrates which may be used herein include, but are not limited to, internal olefins such as 2-pentene, 2-hexene, 3-hexene, 9-octadecene and the like; unsaturated carboxylic acids such as 2-hexenoic acid and esters thereof, oleic acid and esters thereof including triglyceryl esters having a relatively high oleic acid content, erucic acid and esters thereof including triglyceryl esters having a relatively high erucic acid content, ricinoleic acid and esters thereof including triglyceryl esters having a relatively high ricinoleic acid content, linoleic acid and esters thereof including triglyceryl esters having a relatively high linoleic acid content; unsaturated alcohols such as 3-hexen-1-ol, 9-octadecen-1-ol and the like; unsaturated aldehydes such as 3-hexen-1-al, 9-octadecen-1-al and the like. In addition to the above, an organic substrate which may be used herein include alicyclic compounds having at least one internal carbon-carbon double bond and at least one terminal methyl group, a terminal carboxyl group and or a terminal functional group which is oxidizable to a carboxyl group by biooxidation. Examples of such compounds include, but are not limited to, 3,6-dimethyl, 1,4-cyclohexadiene, 3-methylcyclohexene, 3-methyl-1,4-cyclohexadiene and the like.

Examples of the aromatic compounds that may be used herein include but are not limited to, arenes such as o-, m-, p-xylene; o-, m-, p-methyl benzoic acid; dimethyl pyridine, sterols and the like. The organic substrate can also contain other functional groups that are biooxidizable to carboxyl groups such as an aldehyde or alcohol group. The organic substrate can also contain other functional groups that are not biooxidizable to carboxyl groups and do not interfere with the biooxidation such as halogens, ethers, and the like.

Examples of saturated fatty acids which may be applied to yeast cells incorporating the aforementioned fusion constructs according to the present invention include caproic, enanthic, caprylic, pelargonic, capric, undecylic, lauric, myristic, pentadecanoic, palmitic, margaric, stearic, arachidic, behenic acids and combinations thereof. Examples of unsaturated fatty acids which may be applied to genetically modified yeast cells include palmitoleic, oleic, erucic, linoleic, linolenic acids and combinations thereof. Alkanes and fractions of alkanes may be applied which include chain links from C12 to C24 in any combination. An example of a preferred fatty acid mixture is HOSFFA (high oleic sunflower oil, i.e., fatty acid mixture containing approximately 80% oleic acid commercially available from Cognis Corp. as Edenor®).

The following examples are meant to illustrate but not to limit the invention.

EXAMPLE I

Construction of CYP52A2A/CPRB Fusion Gene

PCR primers were designed to the promoter region in CYP52A2A constructs. An approximately 496 bp nucleotide segment containing the CYP52A2A promoter (−496 bp from the start codon of the CYP52A2A gene; see positions 9–504 of FIG. 5A) was amplified using the CYP2A#1 and CYP2A fus primers set forth below. The ORF (open reading frame) of CPR B and its 3'UTR were amplified using CPR fus and CPRB#2. These two PCR products were fused together by PCR using the CYP2A#1 and CPRB#2 primers to generate a construct containing approximately 500 bp of 3'UTR. In all PCR reactions, Platinum Pfx (Stratagene, LaJolla, Calif.), was used. The nucleotide sequences of the aforementioned primers are shown in Table 1 below.

TABLE 1

| | | |
|---|---|---|
| CYP2A#1 | 3659-72M | CCTTAATTAAATGCACGAAGCGGAGATAAAAG (SEQ. ID. NO. 6) |
| CYP2A fus | 106-10A | GTCTAAAGCCATGGTCGTGAT (SEQ. ID. NO. 7) |
| CPR fus | 106-10B | AACATGGCTTTAGACAAGTTAG (SEQ. ID. NO. 8) |
| CPRB#2 | 106-87B | CCTTAATTAATGTCGTTGATAATGACGTTGCG (SEQ. ID. NO. 9) |

The sequence of the resulting construct was verified before use (see FIG. 5 which depicts the nucleic acid sequence (SEQ. ID. NO. 10) and amino acid sequence (SEQ. ID. NO. 11) corresponding to certain delineated nucleic acid sequences). The generated fragment contained three base substitutions in the promoter and ORF regions of the respective genes which were different from the parent sequences, however there were no changes in amino acid composition. There was a "T" to "A" substitution at position 483 in the CYP52A2A promoter region, a "T" to "C" substitution at position 573 and a "C" to "T" substitution at position 2013 of the CPRB ORF. In addition, there is some evidence that, in *C. tropicalis*, codon CTG is not translated as leucine in accordance with the "universal genetic code", but as serine. See, e.g., Ueda et al., Biochemie (1994) 76, 1217–1222. However, this proposition has not been conclusively proven. Accordingly, since the CTG codon at position 652–654 of FIG. 5A may be translated as either a leucine or a serine, the fiftieth amino acid shown in FIG. 5A is designated "X" where "X" may be leucine or serine. This construct was incorporated into an integration vector, pURA in RED B, as a PacI sensitive fragment to generate the new vector, pURA in CPR B/2A-NCP and then transformed into *C. tropicalis.*

The aforementioned procedures for cloning of the CYP52A2A and CPRB genes, preparing the integration vector, pURAin REDB, and transforming cells with the vector are described in aforementioned U.S. application Ser. No. 09/302,620 now U.S. Pat. No. 6,331,420, and International Application No. PCT/US99/20797, and are also included below.

EXAMPLE II

Quantitative Competitive Reverse Transcription Polymerase Chain Reaction (QC-RT-PCR) Protocol QC-RT-PCR is a technique used to quantitate the amount of a specific RNA in a RNA sample. This technique employs the synthesis of a specific DNA molecule that is complementary to an RNA molecule in the original sample by reverse transcription and its subsequent amplification by polymerase chain reaction. By the addition of various amounts of a competitor RNA molecule to the sample, one can determine the concentration of the RNA molecule of interest (e.g., the mRNA transcripts of the CPR or CYTb5 gene). The levels of specific mRNA transcripts are assayed over time in response to the addition of fatty acid or alkane substrates to the growth medium of fermentation grown *C. tropicalis* cultures for the identification and characterization of the genes involved in the oxidation of these substrates.

A. Primer Design

The first requirement for QC-RT-PCR is the design of the primer pairs to be used in the reverse transcription and subsequent PCR reactions. These primers need to be unique and specific to the gene of interest. Primers used to measure the expression of the CYTb5 gene of *C. tropicalis* 20336 using the QC-RT-PCR protocol are listed in Table 2.

TABLE 2

Primers used to measure *C. tropicalis* CYTB5 gene expression in the QC-RT-PCR reactions.

| Primer Name | Direction | Target | Sequence | |
|---|---|---|---|---|
| 3740-179A | F | CYTb5 | CACACCACCCACGACGACTTGTG | (SEQ. ID. NO. 12) |
| 3740-179C | B | CYTb5 | CTTCCGTGCTGAACGACTGCG | (SEQ. ID. NO. 13) |

F = Forward
B = Backward

B. Design and Synthesis of the Competitor DNA Template

The competitor RNA is synthesized in vitro from a competitor DNA template that has the T7 polymerase promoter and preferably carries a small deletion of e.g., about 10 to 25 nucleotides relative to the native target RNA sequence. The DNA template for the in-vitro synthesis of the competitor RNA is synthesized using PCR primers that are between 42 and 46 nucleotides in length. In this example, the primer pairs for the synthesis of the CYTb5 competitor DNA are shown in Table 3.

TABLE 3

Forward and Reverse primers used to synthesize the competitor RNA template for the QC-RT-PCR measurement of CYTb5 gene expression.

| | | |
|---|---|---|
| Forward Primer | Forward Competitor primer - 3740-179B | TAATACGACTCACTATAG GGAGGCACACCACCCACG ACGACTTGTG (SEQ. ID. NO. 14) |
| Reverse Primer | Reverse Competitor primer - 3740-179D | CTTCCGTGCTGAACGACT GCGAATCTTAGCGCCCTT CAAGTT (SEQ. ID. NO. 15) |

The forward primer is used with the corresponding reverse primer to synthesize the competitor DNA template. The primer pairs are combined in a standard Taq Gold polymerase PCR reaction (Perkin-Elmer/Applied Biosystems, Foster City, Calif.) according to the manufacturer's recommended instructions. The PCR reaction mix contains a final concentration of 250 nM of each primer and 10 ng of *C. tropicalis* chromosomal DNA for template. The reaction mixture is placed in a thermocycler for 25 to 35 cycles using the highest annealing temperature possible during the PCR reactions to assure a homogeneous PCR product (in this case 62° C.). The PCR products are either gel purified or filter purified to remove un-incorporated nucleotides and primers. The competitor template DNA is then quantified using the ($A_{260/280}$) method.

C. Synthesis of the Competitor RNA

Competitor template DNA is transcribed In-Vitro to make the competitor RNA using the Megascript T7 kit from Ambion Biosciences (Ambion Inc., Austin, Tex.). 250 nanograms (ng) of competitor DNA template and the in-vitro transcription reagents were mixed and the reaction mixture was incubated for 4 hrs at 37° C. The resulting RNA preparations were then checked by gel electrophoresis for the conditions giving the highest yields and quality of competitor RNA. This step may require optimization according to the manufacturer's specifications. The DNA template was then removed using the DNase I restriction endonuclease. The RNA competitor was then quantified by the ($A_{260/280}$) method. Serial dilutions of the RNA (1 ng/ml to 1 femtogram (fg)/ml) were made for use in the QC-RT-PCR reactions and the original stocks were stored at −70° C.

D. QC-RT-PCR Reactions

QC-RT-PCR reactions were performed using rTth Polymerase Kit (Perkin-Elmer/Applied Biosystems, Foster City, Calif.) according to the manufacturer's recommended instructions. The reverse transcription reaction was performed in a 10 $\mu$l volume with a final concentration of 200 mM for each dNTP, 1.25 units rTth polymerase, 1.0 mM $MnCl_2$, 1× of the 10× buffer supplied with the enzyme from the manufacturer, 100 ng of total RNA isolated from a fermentor grown culture of *C. tropicalis* and 1.25 mM of the appropriate reverse primer. To quantitate CYTb5 expression in *C. tropicalis* an appropriate reverse primer is 3740-179C (See Table 2). Several reaction mixes were prepared for each RNA sample characterized. To quantitate CYTb5 expression a series of 8 to 12 of the previously described QC-RT-PCR reaction mixes were aliquoted to different reaction tubes. 1 ml of a serial dilution containing from 100 pg to 100 fg CYTb5 competitor RNA per ml was added to each tube to bring the final reaction mixtures up to the final volume of 10 $\mu$l. The QC-RT-PCR reaction mixtures were mixed and incubated at 70° C. for 15 min according to the manufacturer's recommended times for reverse transcription to occur. At the completion of the 15 minute incubation, the sample temperature was reduced to 4° C. to stop the reaction and 40 $\mu$l of the PCR reaction mix added to the reaction to bring the total volume up to 50 $\mu$l. The PCR reaction mix consisted of an aqueous solution containing 0.3125 mM of the forward primer 3740-179A (see Table 2), 3.125 mM $MgCl_2$ and 1× chelating buffer supplied with the enzyme from Perkin-Elmer. The reaction mixtures were placed in a Perkin-Elmer GeneAmp PCR System 2400 thermocycler (Perkin-Elmer/Applied Biosystems, Foster City, Calif.) and the following PCR cycle was performed: 94° C. for 1 minute followed by 94° C. for 10 seconds followed by 58° C. for 40 seconds for 17 to 22 cycles. The PCR reaction was completed with a final incubation at 58° C. for 2 minutes followed by 4° C. In some reactions where no detectable PCR products were produced the samples were returned to the thermocycler for additional cycles, and this process was repeated until enough PCR products were produced to quantify using HPLC. The number of cycles necessary to produce enough PCR product is a function of the amount of the target mRNA in the 100 ng of total cellular RNA. In cultures where the CYTb5 gene is highly expressed there is sufficient CYTb5 mRNA message present and less PCR cycles ($\leqq$17) are required to produce a quantifiable amount of PCR product. The lower the concentrations of the target mRNA present the more PCR cycles are required to produce a detectable amount of product.

E. HPLC Quantification

Upon completion of the QC-RT-PCR reactions the samples were analyzed and quantitated by HPLC and by agarose gel electrophoresis. Five to fifteen microliters of the QC-RT-PCR reaction mix was injected into a Waters Bio-Compatible 625 HPLC equipped with a Waters 484 tunable detector (Waters Corp., Milford, Mass.). The detector was set to measure a wave length of 254 nm. The HPLC contained a Sarasep brand DNASep™ column (Sarasep, Inc., San Jose, Calif.) which is placed within the oven and the temperature set for 52° C. The column was installed according to the manufacturer's recommendation of having 30 cm. of heated PEEK tubing installed between the injector and the column. The system was configured with a Sarasep brand Guard column positioned before the injector. In addition, there was a 0.22 mm filter disk just before the column, within the oven. Two buffers were used to create an elution gradient to resolve and quantitate the PCR products from the QC-RT-PCR reactions. Buffer-A consists of 0.1 M tri-ethyl ammonium acetate (TEAA) and 5% acetonitrile (volume to volume). Buffer-B consists of 0.1 M TEAA and 25% acetonitrile (volume to volume). The QC-RT-PCR samples were injected into the HPLC and the linear gradient of 75% buffer-A/25% buffer-B to 45% buffer-A/55% B is run over 6 min at a flow rate of 0.85 ml per minute. The QC-RT-PCR product of the competitor RNA being smaller was eluted from the HPLC column before the larger QC-RT-PCR product from the CYTb5 mRNA(U). The amount of the QC-RT-PCR products was plotted and quantitated with an attached Waters Corporation 745 data module. The log ratios of the amount of CYTb5 mRNA QC-RT-PCR product (U) to competitor QC-RT-PCR product (C), as measured by peak areas, was plotted and the amount of competitor RNA required to equal the amount of CYTb5 mRNA product determined.

EXAMPLE III

Purification of Genomic DNA from *Candida tropicalis* ATCC 20336

A. Construction of Genomic Library 50 ml of YEPD broth (see Appendix) was inoculated with a single colony of *C. tropicalis* 20336 from YEPD agar plate and grown overnight at 30° C. 5 ml of the overnight culture was inoculated into 100 ml of fresh YEPD broth and incubated at 30° C. for 4 to 5 hrs. with shaking. Cells were harvested by centrifugation, washed twice with sterile distilled water and resuspended in 4 ml of spheroplasting buffer (1 M Sorbitol, 50 mM EDTA, 14 mM mercaptoethanol) and incubated for 30 minutes at 37° C. with gentle shaking. 0.5 ml of 2 mg/ml zymolyase (ICN Pharmaceuticals, Inc., Irvine, Calif.) was added and incubated at 37° C. with gentle shaking for 30 to 60 minutes. Spheroplast formation was monitored by SDS lysis. Spheroplasts were harvested by brief centriguation (4,000 rpm, 3 min) and washed once with the spheroplast buffer without mercaptoethanol. Harvested spheroplasts were then suspended in 4 ml of lysis buffer (0.2 M Tris/pH 8.0, 50 mM EDTA, 1% SDS) containing 100 mg/ml Rnase (Qiagen Inc., Chatsworth, Calif.) and incubated at 37° C. for 30 to 60 min.

Proteins were denatured and extracted twice with an equal volume of chloroform/isoamyl alcohol (24:1) by gently mixing the two phases by hand inversions. The two phases were separated by centrifugation at 10,000 rpm for 10 minutes and the aqueous phase containing the high-molecular weight DNA was recovered. NaCl was added to the aqueous layer to a final concentration of 0.2 M and the DNA was precipitated by adding 2 vol of ethanol. Precipitated DNA was spooled with a clean glass rod and resuspended in TE buffer (10 mM Tris/pH 8.0, 1 mM EDTA) and allowed to dissolve overnight at 4° C. To the dissolved DNA, RNase free of any DNase activity (Qiagen Inc., Chatsworth, Calif.) was added to a final concentration of 50 mg/ml and incubated at 37° C. for 30 minutes. Then protease (Qiagen Inc., Chatsworth, Calif.) was added to a final concentration of 100 mg/ml and incubated at 55 to 60° C. for 30 minutes. The solution was extracted once with an equal volume of phenol/chloroform/isoamyl alcohol (25:24:1) and once with equal volume of chloroform/isoamyl alcohol (24:1). 0.1 vol of 3 M sodium acetate and 2 volumes of ice cold ethanol (200 proof) was added to the aqueous phase, and the high molecular weight DNA was spooled with a glass rod and dissolved in 1 to 2 ml of TE buffer.

B. Genomic DNA Preparation for PCR Amplification of CYTb5 Gene

Five 5 ml of YEPD medium was inoculated with a single colony and grown at 30° C. overnight. The culture was centrifuged for 5 min at 1200×g. The supernatant was removed by aspiration and 0.5 ml of a sorbitol solution (0.9 M sorbitol, 0.1 M Tris-Cl/pH 8.0, 0.1 M EDTA) was added to the pellet. The pellet was resuspended by vortexing and 1 ml of 2-mercaptoethanol and 50 ml of a 10 mg/ml zymolyase solution were added to the mixture. The tube was incubated at 37° C. for 1 hr on a rotary shaker (200 rpm). The tube was then centrifuged for 5 min at 1200×g and the supernatant was removed by aspiration. The protoplast pellet was resuspended in 0.5 ml 1×TE (10 mM Tris-Cl/pH 8.0, 1 mM EDTA) and transferred to a 1.5 ml microcentrifuge tube. The protoplasts were lysed by the addition of 50 ml 10% SDS followed by incubation at 65° C. for 20 minutes. Next, 200 ml of 5M potassium acetate was added and after mixing, the tube was incubated on ice for at least 30 minutes. Cellular debris was removed by centrifugation at 13,000×g for 5 minutes. The supernatant was carefully removed and transferred to a new microfuge tube. The DNA was precipitated by the addition of 1 ml 100% (200 proof) ethanol followed by centrifugation for 5 min at 13,000×g. The DNA pellet was washed with 1 ml 70% ethanol followed by centrifugation for 5 min at 13,000×g. After partially drying the DNA under a vacuum, it was resuspended in 200 ml of 1×TE. The DNA concentration was determined by ratio of the absorbance at 260 nm/280 nm ($A_{260/280}$).

EXAMPLE IV

Construction of *Candida tropicalis* 20336 Genomic Library

A genomic library was constructed using λ ZAP Express™ vector (Stratagene, La Jolla, Calif.) (FIG. 6A). Genomic DNA was partially digested with Sau3A1 and fragments in the range of 6 to 12 kb were purified from an agarose gel after electrophoresis of the digested DNA. These DNA fragments were then ligated to BamHI digested λ ZAP Express™ vector arms according to the manufacturer's protocol. Three ligations were set up to obtain approximately $9.8\times10^5$ independent clones. The library was pooled and amplified according to manufacturer instructions to obtain high-titre (>10 plaque forming units/ml) stock for long-term storage. The titre of packaged phage library was ascertained after infection of *E. coli* XL1Blue-MRF' cells. *E. coli* XL1Blue-MRF' cells were grown overnight either in LB medium or NZCYM (See Appendix) containing 10 mM $MgSO_4$ and 0.2% maltose at 37° C. of 30° C., respectively with shaking. Cells were then centrifuged and resuspended in 0.5 to 1 volume of 10 mM $MgSO_4$. 200 ml of this *E. coli* culture was mixed with several dilutions of packaged phage library and incubated at 37° C. for 15 min. To this mixture 2.5 ml of LB top agarose or NZCYM top agarose (maintained at 60° C.) (see Appendix) was added and placed on LB agar or NCZYM agar (see Appendix) present in 82 mm petri dishes. Phage were allowed to propagate overnight at 37° C. to obtain discrete plaques and the phage titre was determined.

EXAMPLE V

Screening of Genomic Library

Figure 6B:
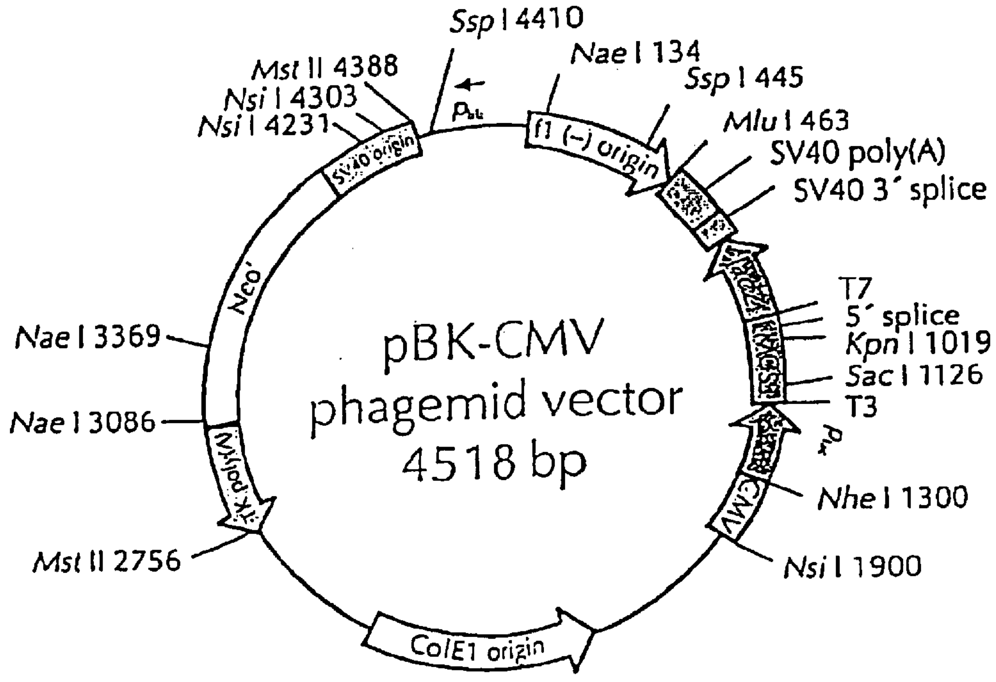
FIG. 6B is a map of the pBK-CMV phagemid vector.

The λ ZAP Express™ vector is a phagemid vector that can be propagated either as phage or plasmid DNA (after conversion of phage to plasmid). Therefore, the genomic library constructed in this vector can be screened either by plaque hybridization (screening of lambda form of library) or by colony hybridization (screening plasmid form of library after phage to plasmid conversion). The mechanism of excision of plasmid pBK-CMV (FIG. 6B) from phage λ ZAP Express™ (Stratagene, LaJolla, Calif.) requires the assistance of a helper phage such as ExAssist™ (Stratagene) and an *E. coli* strain such as XLOR (Stratagene). The plasmid pBK-CMV can replicate autonomously in *E. coli.*

A. Screening Genomic Libraries (Plaque Form)

1) λ Library Plating

*E. coli* XL1Blue-MRF' cells were grown overnight in LB medium (25 ml) containing 10 mM $MgSO_4$ and 0.2% maltose at 37° C., 250 rpm. Cells were then centrifuged (2,200×g for 10 min) and resuspended in 0.5 volumes of 10 mM $MgSO_4$. 500 ml of this *E. coli* culture was mixed with a phage suspension containing 25,000 amplified lambda phage particles and incubated at 37° C. for 15 min. To this mixture 6.5 ml of NZCYM top agarose (maintained at 60° C.) (see Appendix) was added and plated on 80–100 ml NCZYM agar (see Appendix) present in a 150 mm petridish. Phage were allowed to propagate overnight at 37° C. to obtain discrete plaques. After overnight growth plates were stored in a refrigerator for 1–2 hrs before plaque lifts were performed.

2) Plaque Lift and DNA Hybridizations

Magna Lift™ nylon membranes (Micron Separations, Inc., Westborough, Mass.) were placed on the agar surface in complete contact with plaques, and transfer of plaques to nylon membranes was allowed to proceed for 5 min at RT. After plaque transfer the membrane was placed on 2 sheets of Whatman 3M™ (Whatman, Hillsboro, Oreg.) filter paper saturated with a 0.5 N NaOH, 1.0 M NaCl solution and left for 10 min at RT to denature DNA. Excess denaturing solution was removed by blotting briefly on dry Whatman 3M paper™. Membranes were then transferred to 2 sheets of Whatman 3M™ paper saturated with 0.5 M Tris-HCl (pH 8.0), 1.5 M NaCl and left for 5 min to neutralize. Membranes were then briefly washed in 200–500 ml of 2×SSC, dried by air and baked for 30–40 min at 80° C. The membranes were then probed with labeled DNA.

Membranes were prewashed with a 200–500 ml solution of 5×SSC, 0.5% SDS, 1 mM EDTA (pH 8.0) for 1–2 hr at 42° C. with shaking (60 rpm) to get rid of bacterial debris from the membranes. The membranes were prehybridized for 1–2 hrs at 42° C. with (in a volume equivalent to 0.125–0.25 ml/$cm^2$ of membrane) ECL Gold™ buffer (Amersham) containing 0.5 M NaCl and 5% blocking reagent. DNA fragments used as probes were purified from agarose gel using a QIAEXII™ gel extraction kit (Qiagen Inc., Chatsworth, Calif.) according to manufacturer's protocol and labeled using an Amersham ECL™ direct nucleic acid labeling kit (Amersham). Labeled DNA (5–10 ng/ml hybridization solution) was added to the prehybridized membranes and the hybridization was allowed to proceed overnight. The following day, membranes were washed with shaking (60 rpm) twice at 42° C. for 20 min each time in (in a volume equivalent to 2 ml/$cm^2$ of membrane) a buffer containing either 0.1 (high stringency) or 0.5 (low stringency)×SSC, 0.4% SDS and 360 g/l urea. This was followed by two 5 min washes at room temperature in (in a volume equivalent to 2 ml/$cm^2$ of membrane) 2×SSC. Hybridization signals were generated using the ECL™ nucleic acid detection reagent and detected using Hyperfilm ECL™ (Amersham).

Agar plugs which contained plaques corresponding to positive signals on the X-ray film were taken from the master plates using the broad-end of Pasteur pipet. Plaques were selected by aligning the plates with the x-ray film. At this stage, multiple plaques were generally taken. Phage particles were eluted from the agar plugs by soaking in 1 ml SM buffer (Sambrook et al., supra) overnight. The phage eluate was then diluted and plated with freshly grown *E. coli* XL1Blue-MRF' cells to obtain 100–500 plaques per 85 mm NCZYM agar plate. Plaques were transferred to Magna Lift nylon membranes as before and probed again using the same probe. Single well-isolated plaques corresponding to signals on X-ray film were picked by removing agar plugs and eluting the phage by soaking overnight in 0.5 ml SM buffer.

B. Conversion of λ Clones to Plasmid Form

The lambda clones isolated were converted to plasmid form for further analysis. Conversion from the plaque to the plasmid form was accomplished by infecting the plaques into *E. coli* strain BM25.8. The *E. coli* strain was grown overnight at 31° C., 250 rpm in LB broth containing 10 mM $MgSO_4$ and 0.2% maltose until the $OD_{600}$ reached 1.1–1.4. Ten milliliters of the overnight culture was removed and mixed with 100 ml of 1 M $MgCl_2$. A 200 ml volume of cells was removed, mixed with 150 ml of eluted phage suspension and incubated at 31° C. for 30 min. LB broth (400 ml) was added to the tube and incubation was continued at 31° C. for 1 hr with shaking, 250 rpm. 1–10 ml of the infected cell suspension was plated on LB agar containing 100 mg/ml ampicillin (Sigma Chemical Company, St. Louis, Mo.). Well-isolated colonies were picked and grown overnight in 5 ml LB broth containing 100 mg/ml ampicillin at 37° C., 250 rpm. Plasmid DNA was isolated from these cultures and analyzed. To convert the λ ZAP Express™ vector to plasmid form *E. coli* strains XL1Blue-MRF' and XLOR were used. The conversion was performed according to the manufacturer's (Stratagene) protocols for single-plaque excision.

EXAMPLE VI

Figure 7:
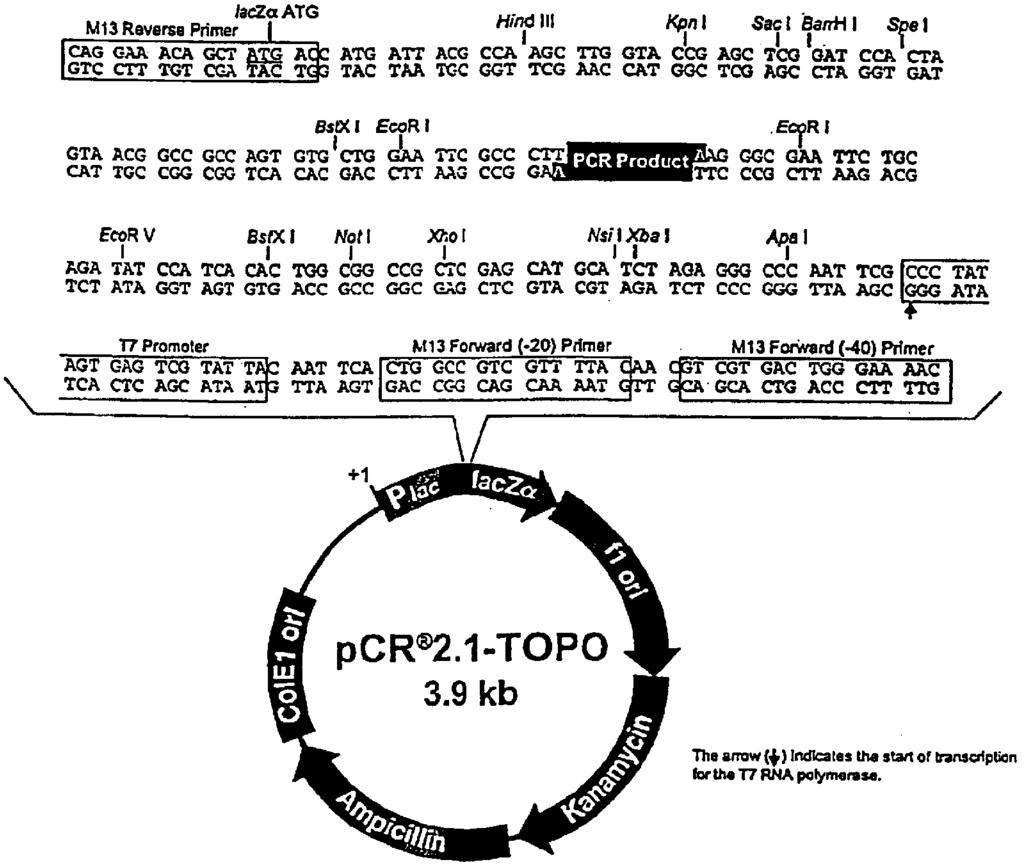
FIG. 7 is schematic representation plasmid pCR2.1™ available from Invitrogen. Nucleic acid sequences for selected restriction sites and other features are depicted (SEQ ID NO:33 and complementary strand SEQ ID NO:34).

Cloning and Characterization of *C. tropicalis* 20336 Cytochrome b5 (CYTb5) Gene The CYTb5 gene was isolated from a *Candida tropicalis* ATCC 20336 genomic library constructed as described in Example IV using a PCR fragment as a probe. The PCR fragment probe for CYTb5 was generated after PCR amplification of *Saccharomyces cerevisiae* genomic DNA with oligonucleotide primers that were designed to amplify a region using the available CYTb5 gene of *S. cerevisiae* from the National Center for Biotechnology Information. A forward primer 3698-66A, 5' ATAAGAATGCGGCCGCTGAACGAGAACCACATCCAGGAG 3' (SEQ. ID. NO. 16) and a reverse primer 3698-66B 5' CCTTAATTAAGGATAACCACATCCATACGTCGC 3' (SEQ. ID. NO. 17) were made based on the *S. cerevisiae* CYTb5 sequence. These primers were used in pairwise combinations in a PCR reaction with Taq DNA polymerase (Perkin-Elmer Cetus, Foster City, Calif.) according to the manufacturer's recommended instructions. A PCR product of approximately 1036 bp was obtained. This product was purified from agarose gel using Qiaquick (Qiagene, Chatsworth, Calif.) and ligated to the pCR2.1™ vector (FIG. 7, Invitrogen, LaJolla, Calif.) according to the recommendations of the manufacturer. This PCR fragment was used as a probe in isolating the *C. tropicalis* 20336 Cytb5 homolog. The genomic library (see Examples IV & V)was screened using this CYTb5 probe and a clone that contained a full length CYTb5 gene was obtained. The clone contained a gene having regulatory and protein coding regions (FIG. 4). An open reading frame of 387 nucleotides encodes a CYTb5 protein of 129 amino acids (FIG. 4).

EXAMPLE VII

Construction of CYP52A2A/CYTb5 Fusion Gene

In a manner similar to Example I above, the 496bp nucleotide segment containing the CYP52A2A promoter is fused to the open reading frame of CYTb5 to create a CYP52A2A promoter/CYTb5 ORF fusion product. The CYP52A2A promoter region is amplified using the CYP2A#1 and CYP2A/b5 fus (TGTGTCGGTCATGGTCGTGATGTG SEQ. ID. NO. 18) primers. The ORF of CYTb5 and its 3'UTR are amplified using b5/2A fus (CACATCACGACCATGACCGACACA SEQ. ID. NO. 19) and b5#2 (CCCTTAATTAAGGGGGGATGGAAGTGGCCG SEQ. ID NO. 20) primers. These two PCR products are fused together by PCR using the CYP52A#1 and b5#2 primers. The resulting construct is verified before use and then incorporated into an integration vector, pURA in RED B, as a PacI sensitive fragment to generate a new vector and then transformed into *C. tropicalis.*

EXAMPLE VIII

Integration of CYP52A2A/CYTb5 and CYP52A2A/CPRB Fusion Genes into the Genome of *Candida tropicalis*

In order to integrate selected genes into the chromosome of *C. tropicalis* there has to be a target DNA sequence, which may or may not be an intact gene, into which the genes can be inserted. There must also be a method to select for the integration event. In some cases the target DNA sequence and the selectable marker are the same and, if so, then there must also be a method to regain use of the target gene as a selectable marker following the integration event. In *C. tropicalis* and its descendants, one gene which fits these criteria is URA3A, encoding orotidine-5'-phosphate decarboxylase. Using it as a target for integration, $ura^-$ variants of *C. tropicalis* can be transformed in such a way as to regenerate a $URA^+$ genotype via homologous recombination. Depending upon the design of the integration vector, one or more genes can be integrated into the genome at the same time. Using a split URA3A gene, homologous integration would yield at least one copy of the gene(s) of interest which are inserted between the split portions of the URA3A gene. Moreover, because of the high sequence similarity between URA3A and URA3B genes, integration of the construct can occur at both the URA3A and URA3B loci. Subsequently, an oligonucleotide designed with a deletion in a portion of the URA gene based on the identical sequence across both the URA3A and URA3B genes, can be utilized to yield *C. tropicalis* transformants which are once again $ura^-$ but which still carry one or more newly integrated genes of choice. $Ura^-$ variants of *C. tropicalis* can also be isolated via other methods such as classical mutagenesis or by spontaneous mutation. Using well established protocols, selection of $ura^-$ strains can be facilitated by the use of 5-fluoroorotic acid (5-FOA) as described, e.g., in Boeke et al., *Mol. Gen. Genet.* 197:345–346 (1984), incorporated herein by reference. The utility of this approach for the manipulation of *C. tropicalis* has been well documented as described, e.g., in Picataggio et al., *Mol. and Cell. Biol.* 11:4333–4339 (1991); Rohrer et al., *Appl. Microbiol. Biotechnol.* 36:650–654 (1992); Picataggio et al., *Bio/Technology* 10:894–898 (1992); U.S. Pat. No. 5,648,247; U.S. Pat. No. 5,620,878; U.S. Pat. No. 5,204,252; U.S. Pat. No. 5,254,466, all of which are incorporated herein by reference.

A. Construction of a URA Integration Vector, pURAin

Figure 9:
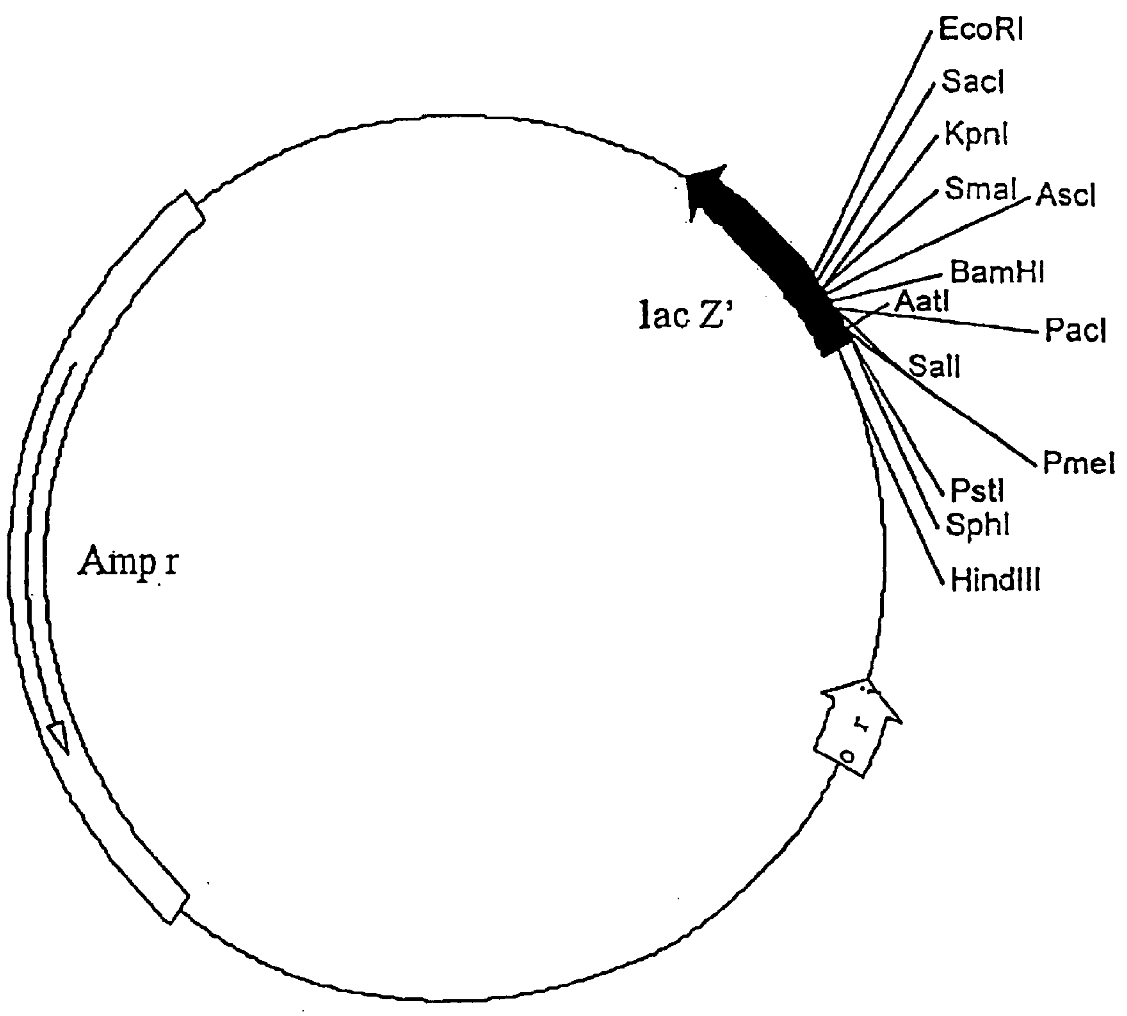
FIG. 9 is a schematic depiction of plasmid pNEB193.
Figure 10:
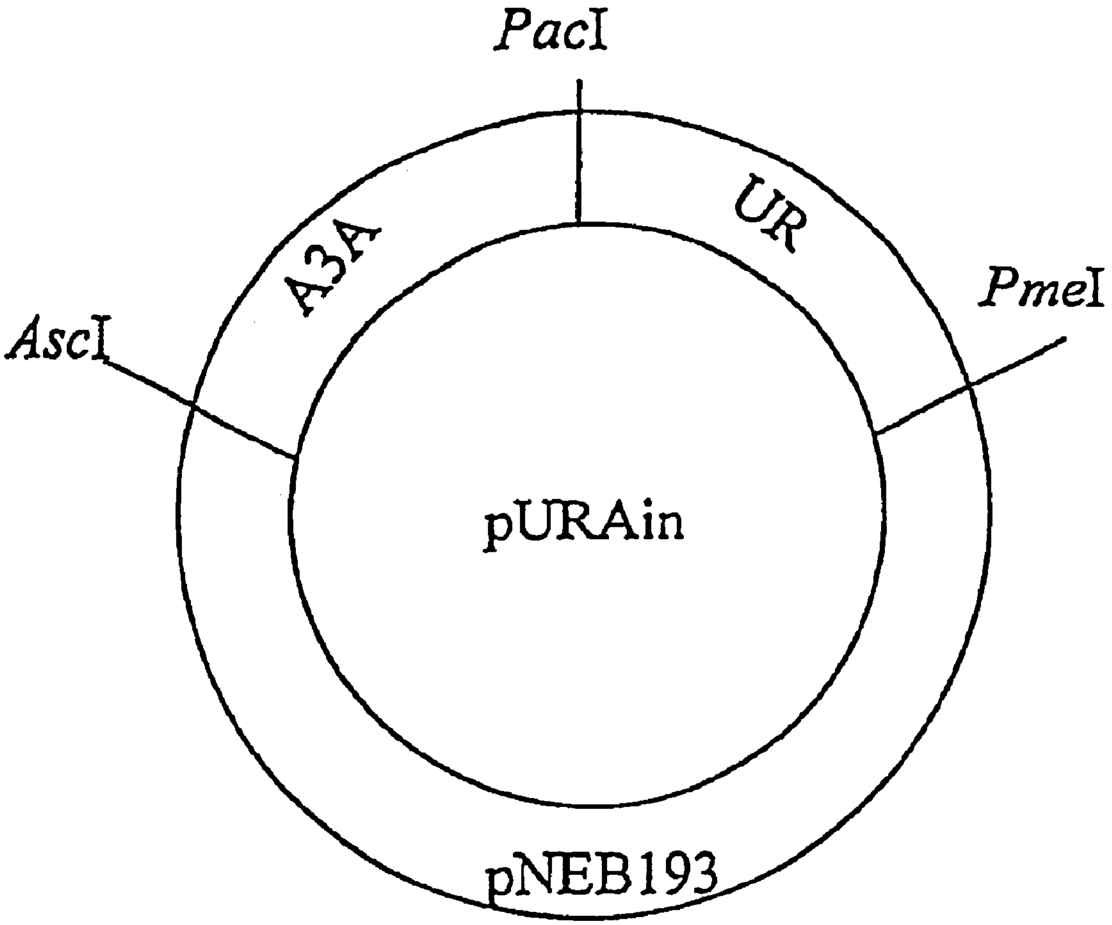
FIG. 10 is a schematic depiction of the pURAin integration vector.

Primers were designed and synthesized based on the 1712 bp sequence of the URA3A gene of *C. tropicalis* 20336. URA3A Primer Set #1a, AGGCGCGCCGGAGTCCAAAAAGACCAACCTCTG, and (SEQ. ID. NO. 21) #1b, CCTTAATTAATACGTGGATACCTTCAAGCAAGTG, (SEQ. ID. NO. 22) was used in PCR with *C. tropicalis* 20336 genomic DNA to amplify URA3A sequences between nucleotide 733 and 1688 as shown in FIG. 8 which depicts the nucleic acid sequence (SEQ. ID. NO. 23) and amino acid sequence (SEQ. ID. NO. 24) corresponding to certain delineated nucleic acid sequences. The primers were designed to introduce unique 5' AscI and 3' PacI restriction sites into the resulting amplified URA3A fragment. AscI and PacI sites were chosen because these sites are not present within CYTb5 or CPRB gene. URA3A Primer Set #2 was used in PCR with *C. tropicalis* 20336 genomic DNA as a template, to amplify URA3A sequences between nucleotide 9 and 758 as shown in FIG. 8. URA3A Primer set #2a, CCTTAATTAAGC TCACGAGTTTTGGGATTTTCGAG (SEQ. ID. NO. 25) and #2b GGGTTTAAACCGCAGAGGTTGGTCTTTTTGGACTC (SEQ. ID. NO. 26) were designed to introduce unique 5' PacI and 3' PmeI restriction sites into the resulting amplified URA3A fragment. The PmeI site is also not present within CYTb5 and CPRB genes. PCR fragments of the URA3A gene were purified, restricted with AscI, PacI and PmeI restriction enzymes and ligated to a gel purified, QiaexII cleaned AscI-PmeI digest of plasmid pNEB193 (FIG. 9) purchased from New England Biolabs (Beverly, Mass.). The ligation was performed with an equimolar number of DNA termini at 16° C. for 16 hr using T4 DNA ligase (New England Biolabs). Ligations were transformed into *E. coli* XL1-Blue cells (Stratagene, LaJolla, Calif.) according to manufacturer's recommendations. White colonies were isolated, grown, plasmid DNA isolated and digested with AscI-PmeI to confirm insertion of the modified URA3A into pNEB 193. The resulting base integration vector was designated pURAin (FIG. 10 SEQ. ID. NO. 27).

B. Construction of pURAin RED B

The next step was to clone the CPRB fusion gene into the pURAin integration vector. In a preferred aspect of the present invention, no foreign DNA other than that specifically provided by synthetic restriction site sequences was incorporated into the DNA which was cloned into the genome of *C. tropicalis*, i.e., with the exception of restriction site DNA only native *C. tropicalis* DNA sequences are incorporated into the genome. pURAin is digested with PacI, QiaexII cleaned, and dephosphorylated with Shrimp Alkaline Phosphatase (SAP) (United States Biochemical, Cleveland, Ohio) according to the manufacturer's recommendations. Approximately 500 ng of PacI linearized pURAin was dephosphorylated for 1 hr at 37° C. using SAP at a concentration of 0.2 Units of enzyme per 1 pmol of DNA termini. The reaction was stopped by heat inactivation at 65° C. for 20 min.

Prior to its use, the CPRB PacI fragment derived using the primers described above was sequenced and compared to CPRB to confirm that PCR did not introduce DNA base pair changes that would result in an amino acid change. Following confirmation, CPRB was ligated to plasmid pURAin which has also been digested with PacI. PacI digested pURAin was dephosphorylated, and ligated to the CPR Expand Hi-Fi PCR product as described previously. The ligation mixture was transformed into *E. coli* XL1 Blue MRF' (Stratagene) and several resistant colonies were selected and screened for correct constructs which contain vector sequence, the inverted URA3A gene, and the amplified CPRB gene (FIG. 3) of 20336. AscI-PmeI digestion confirmed a successful construct. This vector was called pURAin RED B.

C. Construction of Vectors Containing the CYP52A2A/CPRB and CYP52A2A/CYTb5 Fusion Genes The previously constructed integration vector pURA in RED B was chosen as the starting vector. This vector was partially digested with PacI and the linearized fragment was gel-isolated. The active PacI was destroyed by treatment with T4 DNA polymerase and the vector was re-ligated. Subsequent isolation and complete digestion of this new plasmid yielded a vector containing only one active PacI site. This fragment was gel-isolated, dephosphorylated and ligated to the CYP52A2A/CPRB PacI fragment. Alternatively, this fragment is gel-isolated, dephosphorylated and ligated to the CYP52A2A/CYTb5 PacI fragment.

D. Confirmation of Integration of the CYP52A2A/CPRB Fusion Gene.

Based on the vector construct containing the CYP52A2A/CPRB fusion gene used to transform *Candida tropicalis*, a scheme to detect integration was devised. Genomic DNA from transformants was digested with PacI which is an enzyme that cuts and liberates the fusion gene but does not cut within the CYP52A2A and CPRB genes. Digestion of genomic DNA where an integration has occurred at the URA3A or URA3B loci is expected to result in a 3.04 Kb fragment. Southern hybridizations of these digests with fragments of the CPRB gene was used to screen for these integration events. Intensity of the band signal from the Southern using PacI digestion is used as a measure of the number of integration events, (i.e., the more copies of the CYP52A2A/CPRB fusion gene which are present, the stronger the hybridization signal).

*C. tropicalis* URA prototrophs were grown at 30° C., 170 rpm, in 10 ml SC-uracil media for preparation of genomic DNA. Genomic DNA was isolated by the method described previously. Genomic DNA was digested with PacI. A 0.95% agarose gel was used to prepare a Southern hybridization blot. The DNA from the gel was transferred to a Magna-Charge nylon filter membrane (MSI Technologies, Westboro, Mass.) according to the alkaline transfer method of Sambrook et al., supra. For the Southern hybridization, a 3.3 Kb CPRB DNA fragment was used as a hybridization probe. 300 ng of CPRB DNA was labeled using an ECL Direct labeling and detection system (Amersham) and the Southern was processed according to the ECL kit specifications. The blot was processed in a volume of 30 ml of hybridization fluid corresponding to 0.125 ml/cm$^2$. Following a prehybridization at 42° C. for 1 hr, 300 ng of CPRB probe was added and the hybridization continued for 16 hr at 42° C. Following hybridization, the blots are washed two times for 20 min each at 42° C. in primary wash containing urea. Two 5 min secondary washes at RT was conducted, followed by detection according to directions. The blots were exposed for 16 hr as recommended.

Integration was confirmed by the detection of a PacI 3.04 Kb fragment from the genomic DNA of the transformants but not with the *C. tropicalis* 20336 control. This strain was designated HDC25.

EXAMPLE IX

Fusion of the CYP52 Promoters to the ORFs of CPR and CYP52

Based on QC-RT-PCR analysis, it was determined that the CYP52A2A promoter is the strongest induced promoter of the CYP52 family in ATCC 20336. The following promoter/ORF combinations were produced: CYP52A2A promoter/CPR ORF (HDC25) and the CYP52A2A promoter/CYP52A5A ORF (HDC28).

A. Construction of CYP52A2A/CYP52A5A Fusion Gene

PCR primers were designed such that the same promoter region used in previous CYP52A2A constructs described herein was conserved. 496 bp of the CYP52A2A promoter was amplified using the CYP2A#1 (SEQ. ID. NO.: 6) and CYP2A/5A RC fus (SEQ. ID. NO. 28) primers. The ORF of CYP52A5A and its 3'UTR was amplified using CYP2A/5A fus (SEQ. ID. NO.: 29) and CYP5A#2 (SEQ. ID. NO.: 30) primers. These two PCR products were fused together by PCR using CYP2A#1 and CYP5A#2 to generate a construct containing approximately 687 bp of 3'UTR. In all PCR reactions, Platinum Pfx (Stratagene, LaJolla, Calif.), was used. The nucleotide sequences of the aforementioned primers are shown in Table 1 and Table 4.

In order to minimize sequencing, a 1632 bp AatII/MluI fragment from the genomic library plasmid, pPa13 (CYP52A5A), was isolated and used to replace the corresponding fragment of the CYP52A2A promoter/CYP52A5A ORF PCR product. The sequence (SEQ. ID. NO. 31) of the resulting construct was verified before use. (See FIG. 11). This construct was incorporated into an integration vector, pURA in, as a PacI sensitive fragment to generate the new vector, pURAin 2A-5A and then transformed into *C. tropicalis*. This construct was successfully used to generate strains HDC 28-1, -2, -3 and -4. The amino acid sequence of the CYP52A5A protein is set forth in SEQ. ID. NO. 32.

TABLE 4

| | | |
|---|---|---|
| CYP2A/5A RC fus | 218-200B | GGAGTTGTTCAATCATGGTCGTGA TGTGTGTA (SEQ. ID. NO. 28) |
| CYP2A/5A fus | | TACACACATCACGACCATGATTGA ACAACTCC (SEQ. ID. NO. 29) |
| CYP5A#2 | 3659-72L | CCTTAATTAAGGCAGACAACAACT TGGCAAAGTC (SEQ. ID. NO. 30) |

B. Transformat Analysis

Following the isolation of genomic DNA from the transformants, the DNA was digested with PacI. The PacI digests were processed according to the standard Southern method and probed with a 3.3 Kb CYP52A5A fragment. Only those strains receiving the integration construct yielded the anticipated 2.7 Kb band upon Southern hybridization.

C. Strain Comparisons

When comparing strain HDC28-1 to strain H5343 (base strain), it was demonstrated that HDC28-1 has the ability to produce more oleic dicarboxylic acid from HOSFFA than the compared strain. The table lists the increase in oleic dicarboxylic acid production over time as compared to H5343.

| Conversion Time (hr) | Total product (g/Kg) H5343 | Total product (g/Kg) HDC28-1 | % improvement over H5343 |
|---|---|---|---|
| 16 | 8.8 | 16.9 | 92 |
| 25 | 15.4 | 29.2 | 89.6 |
| 41 | 25.9 | 42.8 | 65.2 |
| 48 | 24.9 | 49.2 | 97.6 |
| 64 | 24.9 | 63.7 | 155.8 |
| 73 | 38.7 | 67.5 | 74.4 |

When comparing strain HDC25 to the strain H5343 (base strain), it was demonstrated that HDC25 has an ability to produce more oleic dicarboxylic acid from HOSFFA than the compared strain. The table lists the increase in oleic dicarboxylic acid production over time as compared to H5343.

| Conversion Time | Total product (g/Kg) | | % improvement |
|---|---|---|---|
| (hr) | H5343 | HDC25 | over H5343 |
| 17 | 11.4 | 12.8 | 12.3 |
| 27 | 20.9 | 22.5 | 7.7 |
| 41 | 31.3 | 33.9 | 8.3 |
| 68 | 38 | 51.8 | 36.3 |

It will be understood that various modifications may be made to the embodiments and examples described herein. Therefore, the above description should not be construed as limiting, but merely as exemplifications of preferred embodiments. For example, transformation of host cells can be accomplished using biolistic gene transfer techniques. Although reference has been made herein to production of dicarboxylic acids, it is intended that the present disclosure is applicable to polycarboxylic acids as well. Those with skill in the art will envision other modifications of the various embodiments and examples which are still considered to be within the scope of the claims appended hereto.

APPENDIX

| Media Composition | |
|---|---|
| LB Broth | |
| Bacto Tryptone | 10 g |
| Bacto Yeast Extract | 5 g |
| Sodium Chloride | 10 g |
| Distilled Water | 1,000 ml |
| LB Agar | |
| Bacto Tryptone | 10 g |
| Bacto Yeast Extract | 5 g |
| Sodium Chloride | 10 g |
| Agar | 15 g |
| Distiled Water | 1,000 ml |
| LB Top Agarose | |
| Bacto Tryptone | 10 g |
| Bacto Yeast Extract | 5 g |
| Sodium Chloride | 10 g |
| Agarose | 7 g |
| Distiled Water | 1,000 ml |
| NZCYM Broth | |
| Bacto Casein Digest | 10 g |
| Bacto Casamino Acids | 1 g |
| Bacto Yeast Extract | 5 g |
| Sodium Chloride | 5 g |
| Magnesium Sulfate (anhydrous) | 0.98 g |
| Distilled Water | 1,000 ml |
| NZCYM Agar | |
| Bacto Casein Digest | 10 g |
| Bacto Casamino Acids | 1 g |
| Bacto Yeast Extract | 5 g |
| Sodium Chloride | 5 g |
| Magnesium Sulfate (anhydrous) | 0.98 g |
| Distilled Water | 1,000 ml |
| NZCYM Top Agarose | |
| Bacto Casein Digest | 10 g |
| Bacto Casamino Acids | 1 g |
| Bacto Yeast Extract | 5 g |
| Sodium Chloride | 5 g |

APPENDIX-continued

| Media Composition | |
|---|---|
| Magnesium Sulfate (anhydrous) | 0.98 g |
| Distilled Water | 1,000 ml |
| YEPD Broth | |
| Bacto Yeast Extract | 10 g |
| Bacto Peptone | 20 g |
| Glucose | 20 g |
| Distilled Water | 1,000 ml |
| YEPD Agar* | |
| Bacto Yeast Extract | 10 g |
| Bacto Peptone | 20 g |
| Glucose | 20 g |
| Distilled Water | 1,000 ml |
| YNB | |
| Yeast extract | 3 g/L |
| Maltose | 3 g/L |
| Peptone | 5 g/L |
| Dextrose | 10 g/L |
| DCA2 medium | 5 g/l |
| Peptone | 3.0 |
| Yeast Extract | 6.0 |
| Sodium Acetate | 3.0 |
| Yeast Nitrogen Base (Difco) | 6.7 |
| Glucose (anhydrous) | 50.0 |
| Potassium Phosphate (dibasic, trihydrate) | 7.2 |
| Potassium Phosphate (monobasic, anhydrous) | 9.3 |
| DCA3 medium | g/l |
| 0.3 M Phosphate buffer, containing, pH | 7.5 |
| Glycerol | 50 |
| Yeast Nitrogen base (Difco) | 6.7 |
| SC - uracil* | |
| Bacto-yeast nitrogen base without amino acids | 6.7 g |
| Glucose | 20 g |
| Bacto-agar | 20 g |
| Drop-out mix | 2 g |
| Distilled water | 1,000 ml |
| Drop-out mix | |
| Adenine | 0.5 g |
| Alanine | 2 g |
| Ariginine | 2 g |
| Asparagine | 2 g |
| Aspartic acid | 2 g |
| Cysteine | 2 g |
| Glutamine | 2 g |
| Glutamic acid | 2 g |
| Glycine | 2 g |
| Histidine | 2 g |
| Inositol | 2 |
| Isoleucine | 2 g |
| Leucine | 10 g |
| Lysine | 2 g |
| Methionine | 2 g |
| para-Aminobenzoic acid | 0.2 g |
| Phenylalanine | 2 g |
| Proline | 2 g |
| Serine | 2 g |
| Threonine | 2 g |
| Tryptophan | 2 g |
| Tyrosine | 2 g |
| Valine | 2 g |

*See Kaiser et al., Methods in Yeast Genetics, Cold Spring Harbor Laboratory Press, U.S.A. (1994), incorporated herein by reference.

What is claimed is:

1. A method of converting a fatty acid to its corresponding dicarboxylic acid which comprises isolating a yeast CYP52A2A gene promoter, wherein the yeast CYP52A2A gene promoter consists of about 495 contiguous nucleotides located upstream from nucleotide 1199 of SEQ ID NO:1, or about 495 contiguous nucleotides located upstream from nucleotide 505 of SEQ ID NO:10;

isolating a target gene involved in dicarboxylic acid production;

operably linking the yeast CYP52A2A gene promoter to the open reading frame (ORF) of the target gene involved in dicarboxylic acid production to create a fusion gene;

inserting the fusion gene into an expression vector;

transforming a yeast host cell with the expression vector; and culturing the transformed yeast host cell in a media containing an organic substrate that is biooxidizable to a mono- or polycarboxylic acid.

2. A method of increasing conversion of a fatty acid to its corresponding dicarboxylic acid which comprises isolating a yeast CYP52A2A gene promoter, wherein the yeast CYP52A2A gene promoter consists of about 495 contiguous nucleotides located upstream from nucleotide 1199 of SEQ ID NO:1, or about 495 contiguous nucleotides located upstream from nucleotide 505 of SEQ ID NO:10;

isolating at least one of a CPR gene, a CYTb5 gene, or a CYP52A2A gene;

operably linking the CYP52A2A gene promoter to the open reading frame (ORF) of at least one of a CPR gene, a CYTb5 gene or a CYP52A5A gene to create a fusion gene;

inserting the fusion gene into an expression vector;

transforming a yeast host cell with the expression vector; and culturing the transformed host cell in a media containing an organic substrate that is biooxidizable to a mono- or polycarboxylic acid.

3. The method of claim 1 or 2 wherein the organic substrate is a saturated fatty acid, an unsaturated fatty acid, an alkane, an alkene, an alkyne, or a combination thereof.

4. The method of claim 1 or 2 wherein the yeast host cell is from at least one of Candida, Yarrowia, Bebaromyces, Saccharomyces, Schizosaccharomyces, or Pichia.

5. The method of claim 4 wherein the yeast host cell is from at least one of *Candida tropicalis, C. maltosa, C. apicola, C. paratropicalis, C. albicans, C. cloacae, C.*

*guillermondii, C. intermedia, C. lipolytica, C. parapsilosis,* or *C. zeylenoides.*

6. The method of claim 5 wherein the yeast host cell is from *C. tropicalis.*

7. The method of claim 6 wherein the yeast host cell is from a β-oxidation blocked strain of *C. tropicalis.*

* * * * *